United States Patent
Morriello et al.

(10) Patent No.: US 10,647,727 B2
(45) Date of Patent: May 12, 2020

(54) SUBSTITUTED PYRAZOLO/IMIDAZOLO BICYCLIC COMPOUNDS AS PDE2 INHIBITORS

(71) Applicants: Merck Sharp & Dohme Corp., Rahway, NJ (US); Gregori J. Morriello, Randolph, NJ (US); Michael P. Dwyer, Scotch Plains, NJ (US); Lehua Chang, Ramsey, NJ (US); Yili Chen, Hillsborough, NJ (US); Ming Wang, Belle Mead, NJ (US); Ashley Forster, Harleysville, PA (US); Richard Berger, Harleysville, NJ (US); Kausik K. Nanda, Norristown, PA (US); Jamie L. Bunda, Douglasville, PA (US); William D. Shipe, Chalfont, PA (US)

(72) Inventors: Gregori J. Morriello, Randolph, NJ (US); Lehua Chang, Ramsey, NJ (US); Ashley Forster, Harleysville, PA (US); Richard Berger, Harleysville, NJ (US); Kausik K. Nanda, Norristown, PA (US); William D. Shipe, Chalfont, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/579,115

(22) PCT Filed: Jun. 20, 2016

(86) PCT No.: PCT/US2016/038292
§ 371 (c)(1),
(2) Date: Dec. 1, 2017

(87) PCT Pub. No.: WO2016/209749
PCT Pub. Date: Dec. 29, 2016

(65) Prior Publication Data
US 2018/0162874 A1    Jun. 14, 2018

Related U.S. Application Data

(60) Provisional application No. 62/184,700, filed on Jun. 25, 2015.

(51) Int. Cl.
C07D 487/04    (2006.01)
C07D 498/04    (2006.01)
(Continued)

(52) U.S. Cl.
CPC .......... *C07D 498/04* (2013.01); *A61P 25/06* (2018.01); *A61P 25/16* (2018.01); *A61P 25/18* (2018.01);
(Continued)

(58) Field of Classification Search
CPC .................................................. C07D 487/04
See application file for complete search history.

(56) References Cited

U.S. PATENT DOCUMENTS 4,904,666 A * 2/1990 Friebe ............... C07D 487/04
                                                        514/262.1
6,573,263 B2    6/2003 Niewohner et al.
(Continued)

FOREIGN PATENT DOCUMENTS

EP    1097706 A1    5/2001
EP    1097707 A1    5/2001
(Continued)

OTHER PUBLICATIONS

Chemical Abstracts Registry No. 1360304-30-8, indexed in the Registry file on STN CAS Online on Mar. 7, 2012 (Year: 2012).*
(Continued)

*Primary Examiner* — Laura L Stockton
(74) *Attorney, Agent, or Firm* — Dianne Pecoraro; John C. Todaro

(57) ABSTRACT

The present invention is directed to pyrimidine carboxamide compounds of formula I which are useful as therapeutic agents for the treatment of central nervous system disorders associated with phosphodiesterase 2 (PDE2). The present invention also relates to the use of such compounds for treating neurological and psychiatric disorders, such as schizophrenia, psychosis, Parkinson's disease, Parkinson's disease dementia (PDD), or Huntington's disease, and those associated with striatal hypofunction or basal ganglia dysfunction.

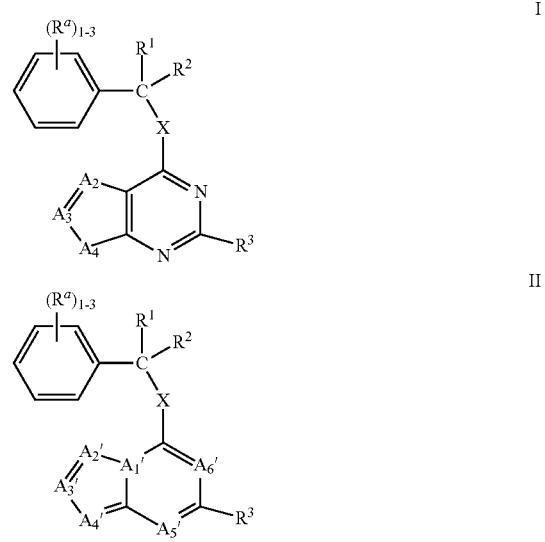

12 Claims, No Drawings

(51) Int. Cl.
C07D 473/34 (2006.01)
A61P 25/06 (2006.01)
A61P 25/28 (2006.01)
A61P 25/18 (2006.01)
A61P 25/16 (2006.01)

(52) U.S. Cl.
CPC ............ A61P 25/28 (2018.01); C07D 473/34 (2013.01); C07D 487/04 (2013.01)

(56) References Cited

U.S. PATENT DOCUMENTS

| | | |
|---|---|---|
| 7,144,913 B2 | 12/2006 | Wang et al. |
| 7,419,969 B2 | 9/2008 | Naidu et al. |
| 8,598,155 B2 | 12/2013 | Helal et al. |
| 8,680,116 B2 | 3/2014 | DeLeon et al. |
| 2007/0135457 A1 | 6/2007 | Beyer et al. |
| 2007/0281917 A1 | 12/2007 | Naidu et al. |
| 2009/0253677 A1 | 10/2009 | Beaulieu et al. |
| 2012/0214791 A1 | 8/2012 | Helal et al. |
| 2014/0303112 A1 | 10/2014 | Chen et al. |

FOREIGN PATENT DOCUMENTS

| | | |
|---|---|---|
| EP | 1671962 A1 | 6/2006 |
| EP | 1956009 A1 | 8/2008 |
| EP | 1671616 B1 | 2/2012 |
| WO | WO2003035076 | 5/2003 |
| WO | WO2003035077 A1 | 5/2003 |
| WO | WO2005041957 | 10/2004 |
| WO | WO2004096128 | 11/2004 |
| WO | WO2005061497 | 7/2005 |
| WO | WO2006021553 A1 | 3/2006 |
| WO | WO2006024640 | 3/2006 |
| WO | WO200672615 | 7/2006 |
| WO | WO2005067546 A3 | 12/2006 |
| WO | WO2007058646 | 5/2007 |
| WO | WO2009016498 | 2/2009 |
| WO | WO2009034386 A1 | 3/2009 |
| WO | WO2009043320 A3 | 5/2009 |
| WO | WO2009117540 | 9/2009 |
| WO | WO2010136493 | 12/2010 |
| WO | WO2012114222 | 8/2012 |
| WO | WO2013034758 | 9/2012 |
| WO | WO2013034761 | 9/2012 |
| WO | WO2012151567 | 11/2012 |
| WO | WO2012168817 | 12/2012 |
| WO | WO201300924 | 1/2013 |
| WO | WO2013034755 | 3/2013 |
| WO | WO2013098373 | 7/2013 |
| WO | 2013161913 | 10/2013 |
| WO | WO2014010732 | 1/2014 |
| WO | WO2014019979 | 2/2014 |
| WO | WO2014083327 A1 | 6/2014 |
| WO | WO2014124458 A1 | 8/2014 |
| WO | WO2014139983 | 9/2014 |
| WO | WO2015012328 | 1/2015 |
| WO | WO2016192083 A1 | 12/2016 |
| WO | WO2017000276 A1 | 1/2017 |
| WO | WO2017000277 A1 | 1/2017 |
| WO | WO2005063723 | 7/2017 |

OTHER PUBLICATIONS

PubChem CID 16627006—National Center for Biotechnology Information. PubChem Compound Database; CID=16627006, https://pubchem.ncbi. nlm.nih.gov/compound/16627006 (accessed Jul. 6, 2018), create date Jul. 31, 2007 (Year: 2007).*
PubChem CID 39840575—National Center for Biotechnology Information. PubChem Compound Database; CID=39840575, https://pubchem.ncbi. nlm.nih.gov/compound/39840575 (accessed Jul. 6, 2018), create date May 29, 2009 (Year: 2009).*
Noell et al., Journal of Organic Chemistry, 1958, 23, pp. 1547-1550 (Year: 1958).*
Cheng et al., Journal of Organic Chemistry, 1958, 23, pp. 852-861 (Year: 1958).*
PubChem CID 25997445, National Center for Biotechnology Information. PubChem Compound Database; CID=25997445, https://pubchem.ncbi.nlm.nih.gov/compound/25997445 (accessed Jan. 11, 2019), create date May 28, 2009. (Year: 2009).*
PubChem CID 47283100, National Center for Biotechnology Information. PubChem Compound Database; CID=47283100, https://pubchem.ncbi.nlm.nih.gov/compound/47283100 (accessed Jan. 11, 2019), create date Nov. 26, 2010. (Year: 2010).*
PubChem CID 53502189, National Center for Biotechnology Information. PubChem Compound Database; CID=53502189, https://pubchem.ncbi.nlm.nih.gov/compound/53502189 (accessed Jan. 11, 2019), create date Dec. 3, 2011. (Year: 2011).*
PubChem CID 71886393, National Center for Biotechnology Information. PubChem Compound Database; CID=71886393, https://pubchem.ncbi.nlm.nih.gov/compound/71886393 (accessed Jan. 11, 2019), create date Nov. 29, 2013. (Year: 2013).*
PubChem CID 81907047, National Center for Biotechnology Information. PubChem Compound Database; CID=81907047, https://pubchem.ncbi.nlm.nih.gov/compound/81907047 (accessed Jan. 11, 2019), create date Oct. 20, 2014. (Year: 2014).*
PubChem CID 53526277, National Center for Biotechnology Information. PubChem Compound Database; CID=53526277, https://pubchem.ncbi.nlm.nih.gov/compound/53526277 (accessed Jan. 11, 2019), create date Dec. 3, 2011. (Year: 2011).*
Chemical Abstracts Registry No. 1360062-41-4, indexed in the Registry file on STN CAS Online on Mar. 7, 2012. (Year: 2012).*
PubChem CID 81909566—National Center for Biotechnology Information. PubChem Database. JSSLIZNSHOUQJT-UHFFFAOYSA-N, CID=81909566, https://pubchem.ncbi.nlm.nih.gov/compound/81909566 (accessed on May 9, 2019), create date Oct. 20, 2014. (Year: 2014).*
PubChem CID 56904898 {National Center for Biotechnology Information. PubChem Database. SFDYUJMEYJVHHK-UHFFFAOYSA-N, CID=56904898, https://pubchem.ncbi.nlm.nih.gov/compound/56904898 (accessed on May 9, 2019), create date Mar. 30, 2012. (Year: 2012).*
Ahlstrom et al., Inactivation of Atrial Natriuretic Factor-Stimulated, Biochemical Pharmacology, 2000, 1133-1139, 59.
Arulomozhi et al., Migraine: Current Therapeutic Targets and Future Avenues, Current Vascular Pharmacology, 2006, 117-128, 4.
Beavo et al., Cyclic GMP as Substrate and Regulator of Cyclic Nucleotide Phosphodiesterases (PDEs), Rev. Physio Biochem Pharm, 1999, 67-104, 135.
Bernard et al., PDE2 is a Novel Target for Attenuating Tumor Formation in a Mouse Model of UVB-Induced Skin Carcinogenesis, Plos One, 2014, 1-8, 9.
Boess et al., Inhibition of phosphodiesterase 2 increases neuronal cGMP, synaptic plasticity and memory, Neuropharmacology, 2004, 1081-92, 47.
Boyd et al., 2-Substituted -4,5-Dihydroxypyrimidine-6-Carboxamide Antiviral Targeted Libraries, J. Comb. Chem, 2009, 1100-1104, 11.
Brandon et al., Potential CNS Applications for, Annual Reports in Medicinal Chemistry, 2007, 3-11, 42.
Bubb et al., Inhibition of Phosphodiesterase 2 Augments cGMP and, Circulation, 2014, 496-507, 268.
Cote et al., Comparative Involvement of Cyclic Nucleotide, Endocrinology, 1999, 3594-3601, 140.
Demaria et al., Highlights of the Year in JACC 2013, j. aMER. cOLL. cARD, 2014, 570-602, 63, (6).
Dickinson et al., Activation of cGMP-stimulated phosphodiesterase by nitroprusside limits, Biochem J., 1997, 371-377, 323.
Ding et al., Protective effects of phosphodiesterase 2 inhibitor on depression- and -Anxiety-Like Behaviors: Involvement of antioxidant and anti-apotoic Mechanisms, Behaviorual Brain Research, 2014, 150-158, 268.

(56) References Cited

OTHER PUBLICATIONS

Domek-Lopacinska et al., The Effect of Selective Inhibition of Cyclic GMP Hydrolyzing Phosphodiesterases 2 and 5 on Learning and Memory Processes and Nitric Oxide Synthase Activity, Brain Research, 2008, 68-77, 1216.
Ducrot et al., CoMFA and CoMSIA 3D-Quantitative Structure-Activity Relationship Model on Benzodiaepine Derivatives, Inhibitors of Phosphodiesterase IV, J. of Computer Aided Molecular Designs, 2001, 767-785, 15.
Duran et al., The NO cascade, eNOS Location, and Microvascular Permeability, Cardiovascular Research, 2010, 254-261, 87.
Favot et al., VEGF-Induced HUVEC Migration and Proliferation, Schattauer GmbH Stuttgart, 2003, 334-343, 90.
Gergega et al., Systematic Effect of Benzo-Annelation on Oxo-Hydroxy Tautomerism of Heterocyclic, J. Phys. Chem A., 2007, 4934-4943, 111.
Giuliano et al., Correction to Tautomerism in 4-Hydroxypyrimidine, S-Methyl-2-thiouracil, and 2-Thiouracil, The Journal of Physical Chemistry A, 2011, 8178-8179, 115.
Giuliano et al., Tautomerism in 4-Hydroxypyrimidine, S-Methyl-2-thiouracil, and 2-Thiouracil, J. Phys. Chem. A, 2010, 12725-12730, 114.
Haynes et al., Erythro-9-(2-Hydroxy-3-Nonyl) Adenine Inhibits Cyclic-3',5' Guanosine Monophosphate—Stimulated Phosphodiesterase to Reverse Hypoxic Pulmonary Vasoconstriction in the Perfused Rat Lung, The J. of Pharmacology, 1996, 752-757, 276.
Herring et al., No-cGMP Pathway Increases the Hyperpolarisation-Activated Current ,I, and Heart Rate During Adrenergic Stimulation, Cardiovascular Research, 2001, 446-453, 52.
Hiramoto et al., Role of Phosphodiesterase 2 in Growth and Invasion of HUman Maligant Melanoma, Cellular Signaling, 2014, 1807-1817, 26.
Huang et al., A Fluroescence Polarization Assay for Cyclic Nucleotide Phosphodiesterases, J. of Biomolecular Screening, 2002, pp. 215-222, 7.
Jorgensen et al., Selective Inhibitors of PDE2, PDE9, and PDE10: Modulators of Activity of the Central Nervous System, Annual Reports in Medicinal Chemistry, 2013, pp. 37-55, 48.
Keravis et al., Cyclic Nucleotide Hydrolysis in Bovine Aortic Endothelial Cells in Culture: Differential Regulation in Cobblestone and Spindle Phenotypes, J. Vasc. Res, 2000, 235-249, 37.
Kheifets et al., Structure and Amide—Amide Tautomerism of 4-Hydroxypyrimidines. Determination of the Tautomeric Composition by 13C NMR Spectroscopy, Russ. J. of Organic Chemistry, 2000, 1373-1387, 36, 9.
Lieberman et al., Effectiveness of Antipsychotic Drugs in Patients with Chronic Schizophrenia, New England J. of Medicine, Sep. 22, 2005, pp. 1209-1223, 353, US.
Lopez et al., Solution and solid state (CPMAS) NMR Studies of the Tautomerism of Six-Membered Heterocyclic Compounds Related to 2-Pyridones, Spectroscopy, 2000, pp. 121-126, 14.
Masood et al., Anxiolytic Effects of Phosphodiesterase-2 Inhibitors Associated with Increased cGMP Signaling, J. of Pharmacology, 2009, 690-699, 331.
Masood et al., Reversal of Oxidative Stress-Induced Anxiety by Inhibition of Phosphodiesterase-2 in Mice, J. of Pharmacology and Experimental Therapeutics, 2008, 369-379, 326.
Michie et al., Rapid Regulation of PDE-2 and PDE-4 Cyclic AMP Phosphodiesterase Activity Folloiwng Ligation of the T Cell Antigen Receptor on Thymocytes: Analysis Using theSelctive Inhibitors Erythro-9-(2-Hydroxy-3Nonyl)-Adenine (EHNA) and Rolipram, Cell Signal, 1996, 97-110, 8.
Morita et al., Characterization of Phosphodiesterase 2A in Human Malignant Melanoma PMP Cells, Oncology Reports, 2013, 1275-1284, 29.
Netherton et al., Vascular Endothelial Cell Cyclic Nucleotide phosphodiesterases and Regulated Cell Migration: IMplications in Angiogenesis, Molecular Pharmacology, 2005, 263-272, 67.
P. C. Tfelt-Hansen et al., One Hundred Years of Migraine Research: Major Clinical and, Headache, 2011, 752-778, 51.
Pace et al., Dihydroxypyrimidine-4-Carboxamides as Novel Poten and Selective HIV Integrase Inhibitors, J. Med Chem., 2007, 2225-2239, 50.
Petrocchi et al., From dihydroxypyrimidine carboxylic acids to carboxamide, Bioorganic & Medicinal Chemistry Letters, 2007, 350-353, 17.
Plummer et al., Discovery of Poten, Selective, Bioavailable Phosphodiesterase 2 (PDE2) Inhibitors Active in an Osteoarthritis Pain Model, Part I: Transformation of Selective Pyrazolodiazepinone Phosphodiesterase 4 (PDE4) Inhibitors into Selective PDE2 Inhibitors, Biorganic & Medicinal Chemistry Letters, 2013, 3438-3442, 23.
Plummer et al., Discovery of potent selective bioavailable phosphodiesterase, Bioorganic & Medicinal Chemistry Letters, 2013, 3443-3447, 23.
Pubchem-CID-242418849, Create Date: Feb. 29, 2008, (Feb. 29, 2008), p. 3, Fig.
Pubchem-CID-56912451, Create Date: Mar. 30, 2012 (Mar. 30, 2012).
Pubchem-CID-81908853, Create Date: Oct. 20, 2014 (Oct. 20, 2014), p. 3, Fig.
Pubchem-CID70727560, Create Date: Mar. 4, 2013 (Mar. 4, 2013), p. 3, Fig.
Reierson et al., Repeated antidepressant therapy increases cyclic GMP signaling, Neurosci Letter, 2009, 149-153, 466 (3).
Rivet-Bastide et al., cGMP-stimulated Cyclic Nucleotide Phosphodiesterase Regulates the Basal, J. Clin. Invest, 1997, 2710-2718, 99.
Sadhu et al., Differential Expression of the Cyclic GMP-Stimulated Phosphodiesterase PDE2A in HUman Venous and Capillary Endothelial Cells, J. of Histochemistry & Cytochemistry, 1999, 895-905, 47.
Sanchez et al., Gas-Phase Tautomeric Equilibrium of 4-Hydroxypyrimidine, J. Am. Chem Soc., 2007, 6287-6290, 129.
Savai et al., Targeting Cancer with Phosphodiesterase Inhibitors, Expert Opinion, 2010, 117-131, 19.
Surapisitchat et al., Differential Regulation of Endothelial Cell Permeability by cGMP via Phosphodiesterases 2 and 3, Circulation Research, 2007, 811-818, 101.
Suvrana et al., Hydrolysis of N-Methyl-D-aspartate Receptor-Stimulated cAMP, J. of Pharmacology, 2002, 249-256, 302.
Van Staveren et al., The effects of phosphodiesterase inhibition on cyclic GMP and cyclic, Brain Research, 2001, 275-286, 888.
Vandecasteele, Cyclic GMP regulation of the L-type Ca2+ channel current, J. of Physiology, 2001, 329-340, 533.
Velardez et al., Role of Phosphodiesterase and Protein Kinase G on Nitric Oxide-Induced Inhibition of Prolactin Relase from the Rat Anterior Pituitary, Europe J. of Endocrinology, 2000, 279-284, 143.
Wakabayashi et al., Involvement of Phosphodiesterase Isozymes in Osteoblastic, J. of Bone and Mineral Research, 2002, 249-253, 17.
Gentles, R et al, Preliminary SAR studies on non-apamin-displacing 4-(aminomethylaryl)pyrrazolopyrimidine K"C" a channel blockers, Bioorganic & Medicinal Chemistry Letters, Pergamon, 2008, 5694-5697, 18 (20).
Novinson, T et al, Synthesis and antifungal properties of certain 7-alkylaminopyrazolo(1,5-a)pyrimidines, Journal of Medicinal Chemistry, American Chemical Society, 1977, 296-299, 20 (2).
Sutcliffe, E et al, Potential Purine Antagonists. XXXII. The Synthesis and Antitumor Activity of Certain Compounds Related to 4-Aminopyrazolo[3,4-d]pyrimidine, Journal of Medicinal and Pharmaceutical Chemistry, 1962, 588-607, 5 (3).
Veronika, S et al, Discovery of the first inhibitors of bacterial enzymed-aspartate ligase from Enterococcus faecium (Aslfm), European Journal of Medicinal Chemistry, 2013, 208-220, 67.

\* cited by examiner

SUBSTITUTED PYRAZOLO/IMIDAZOLO BICYCLIC COMPOUNDS AS PDE2 INHIBITORS

CROSS REFERENCE TO RELATED APPLICATIONS

This application is the National Stage of International Application No. PCT/US2016/38292 filed on Jun. 20, 2016, which claims the benefit under U.S. Ser. No. 62/184,700, filed on Jun. 25, 2015.

FIELD OF THE INVENTION

The invention relates generally to compounds which act as inhibitors of the phosphodiesterase (PDE) 2 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side effects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic receptors associated with cyclic adenosine monophosphate (cAMP). These ubiquitous secondary messengers are responsible for altering the function of many intracellular proteins. Cyclic AMP is thought to regulate the activity of cAMP-dependent protein kinase (PKA), which in turn phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these secondary messengers, known as 3',5'-cyclic nucleotide specific phosphodiesterases (PDEs). The PDE superfamily includes twenty-one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45%, suggests that it may be possible to develop selective inhibitors for each of these families.

PDE2 is highly expressed in the brain, but is also found in many other tissues as well, and therefore has a broad array of function and utility (J. A. Beavo, et al., Rev. Physio. Biochem. Pharm., 135, 67 (1999)). Amongst others, PDE2 has been shown to have therapeutic potential in neuronal development, learning, and memory (W. C. G. van Staveren, et al., Brain Res., 888, 275 (2001) and J. O'Donnell, et al., J. Pharm. Exp. Ther., 302, 249 (2002)); prolactin and aldosterone secretion (M. O. Velardez, et al., Eur. J. Endo., 143, 279 (2000) and N. Gallo-Payet, et al., Endo., 140, 3594 (1999)); bone cell differentiation, growth, and bone resorption (C. Allardt-Lamberg, et al., Biochem. Pharm., 59, 1133 (2000) and S. Wakabayashi, et al., J. Bone, Miner. Res., 17, 249 (2002); immunological response (M. D. Houslay, et al., Cell. Signal., 8, 97 (1996); vascular angiogenesis (T. Keravis, et al., J. Vasc. Res., 37, 235 (2000); inflammatory cell transit (S. L. Wolda, et al., J. Histochem. Cytochem., 47, 895 (1999); cardiac contraction (R. Fischmeister, et al., J. Clin. Invest., 99, 2710 (1997), P. Donzeau-Gouge, et al., J. Physiol., 533, 329 (2001), and D. J. Paterson, et Al., Card. Res., 52, 446 (2001)); platelet aggregation (R. J. Haslam, et Al., Biochem. J., 323, 371 (1997); female sexual arousal disorder (C. P. Wayman, et al., EP Patent Publications EP10977707 and EP1097706; osteoarthritis pain (M. Plummer et, al., Bioorganic & Medicinal Chemistry Letters, 23(11), 3438-3442 and 3443-3447(2013)); malignant melanoma (H. Morita, et al., Oncology Reports, 29, 1275-1284, 2013; Hiramoto, et al., Cell. Signal., 26(9), 1807-1817, 2014; and J. J. Bernard, et al., PloS ONE 9(10): e109862, 2014); heart failure (A. N. DeMaria, et al., J. Amer. Coll. Card. 63 (6), 570-602, 2014); pulmonary hypertension (K. J, Bubb, et al., Circulation, 130, 496-508, 2014); depression and anxiety (L. Ding, et al., Behav. Brain Res. 268, 150-158, 2014); and hypoxic pulmonary vasoconstriction (J. Haynes, et al., J. Pharm. Exp. Ther., 276, 752 (1996)). See also 2-Substituted-4,5-dihydroxypyrimidine-6-carboxamide Antiviral Targeted Libraries, Vincent Boyd et al., Journal of Combinatorial Chemistry (2009), 11(6), 1100-1104; From Dihydroxypyrimidine Carboxylic Acids to Carboxamide HIV-1 Integrase Inhibitors: SAR Around the Amide Moiety, Alessia Petrocchi et al., Bioorganic & Medicinal Chemistry Letters (2007), 17(2), 350-353; Dihydroxypyrimidine-4-carboxamides as Novel Potent and Selective HIV Integrase Inhibitors, Paola Pare et al., Journal of Medicinal Chemistry (2007), 50(9), 2225-2239; US2007135457, WO2012151567, US20090253677, US20070281917, WO2004096128, WO2003035077, WO2003035076, WO2007058646, WO2009117540, and U.S. Pat. No. 7,419, 969.

Inhibition of PDE2 (e.g., PDE2A) has been shown to enhance cognitive function across multiple preclinical models of cognitive performance that reflect improvements in recognition memory, social interactions and working memory, which are all deficient in schizophrenia (Boess et al., *Inhibition of Phosphodiesterase 2 Increases Neuronal cGMP, Synaptic Plasticity and Memory Performance*, Neuropharmacology, 47(7): 1081-92, 2004). PDE2A inhibition was also shown to improve cognitive deficits that develop in aging and Alzheimer's disease (Domek-Lopacinska and Strosznajder, *The Effect of Selective Inhibition of Cyclic GMP Hydrolyzing Phosphodiesterases 2 and 5 on Learning and Memory Processes and Nitric Oxide Synthetase Activity in Brain During Aging*, Brain Research, 1216:68-77, 2008). The role of PDE2 inhibition in cognitive disorders was also shown in Brandon et al., *Potential CNS Applications for Phosphodiesterase Enzyme Inhibitors*, Annual Reports in Medicinal Chemistry 42: 4-5, 2007 (compound BAY 60-7550 was reported to have significant potency at other PDE isoforms, had high clearance and limited brain penetration). See also Jorgenson, et al, Annual Reports in Medicinal Chemistry 48: 37-55, 2013. "Selective Inhibitors of PDE2, PDE9, and PDE10: Modulators of Activity of the Central Nervous System".

PDE2 inhibitors have also been shown to have efficacy in preclinical models of anxiety and depression (Masood et al., Anxiolytic Effects of Phosphodiesterase-2 Inhibitors Associated with Increased cGMP Signaling, JPET 331(2):690-699, 2009; Masood et al., Reversal of Oxidative Stress-Induced Anxiety by Inhibition of Phosphodiesterase-2 in Mice, JPET 326(2):369-379, 2008; Reierson et al., Repeated Antidepressant Therapy Increases Cyclic GMP Signaling in Rat Hippocampus, Neurosci. Lett., 466(3):149-53, 2009). See also Ducrot et al., CoMFA and CoMSIA 3D-quantitative structure-activity relationship model on benzodiazepine derivatives, inhibitors of phosphodiesterase IV, J Computer-Aided Molecular Design, 15: 767785, 2001; US20120214791; WO2012168817; WO2013034755; WO2013034758; WO2013034761; WO2005041957; WO2005061497; WO2006024640; WO2013161913; WO2010136493; WO 2013098373; WO 2009016498; U.S. Pat. Nos. 6,573,263, 8,598,155, and 8,680,116; WO2015012328; WO2014139983; WO2014019979; WO2014010732; WO2013000924; WO2012114222; WO2006072615; WO2005063723; M. Plummer et al., Bioorg Med Chem Lett 23(11), 3438, 2013; and M. Plummer et al., Bioorg Med Chem Lett 23(11), 3443, 2013.

An increase in vascular permeability has been shown to be attributable to increased activity of PDE2. PDE2 and PDE3 in the endothelium can act as a sensor or switch to detect normal versus pathological concentrations of cGMP and thus regulate endothelial permeability accordingly with potential relevance to migraine. See Surapisitchat et al, *Differential Regulation of Endothelial Cell Permeability by cGMP via Phosphodiesterase 2 and 3*, Circulation Research, 2007; 101, pgs.: 811-818 and Duran et al., *The NO Cascade, eNOS Location and Microvascular Permeability*, Cardiovascular Res. (2010) 87, 254-261. Cerebral vasodilation is considered a major cause of migraine. See P. C. Tfelt-Hansen and P. J. Koehler, *One hundred years of migraine research: major clinical and scientific observations from 1910 to 2010*, Headache, 2011. 51(5), 752-578 and D. K. Arulmozhi et al., *Migraine: current therapeutic targets and future avenues*, Current Vascular Pharmacology, 2006, 4(2), 117-128. Therefore, PDE2 inhibition may have utility as a treatment or prophylactic for migraine.

The need for new and improved PDE2 modulators believed to be useful for treating PDE2 conditions, diseases or disorders associated with PDE2 such as Alzheimer's disease, cognitive impairment associated with schizophrenia, depression, migraines, and the like continues to exist. Inhibitors of PDE2 are not only believed to be useful in treating schizophrenia but also a wide variety of conditions or disorders that would benefit from increasing levels of cAMP and/or cGMP within neurons, including a variety neurological, psychotic, anxiety and/or movement disorders. Accordingly, agents that inhibit PDE2 and PDE2A would be desirable as therapeutics for neurological and psychiatric disorders.

SUMMARY OF THE INVENTION

The present invention is directed to substituted pyrazolo and imidazolo bicyclic compounds which may be useful as therapeutic agents for the treatment of central nervous system and/or peripheral disorders associated with phosphodiesterase 2 (PDE2). The present invention also relates to the use of such compounds for treating neurological and psychiatric disorders, such as schizophrenia, psychosis, Alzheimer's, cognitive impairment, anxiety, depression, migraines, or Huntington's disease, Parkinson's disease, Parkinson's disease dementia (PDD), and other diseases associated with striatal hypofunction or basal ganglia dysfunction.

DETAILED DESCRIPTION OF THE INVENTION

The present invention is directed to substituted pyrazolo and imidazolo bicyclic compounds of formula I and II:

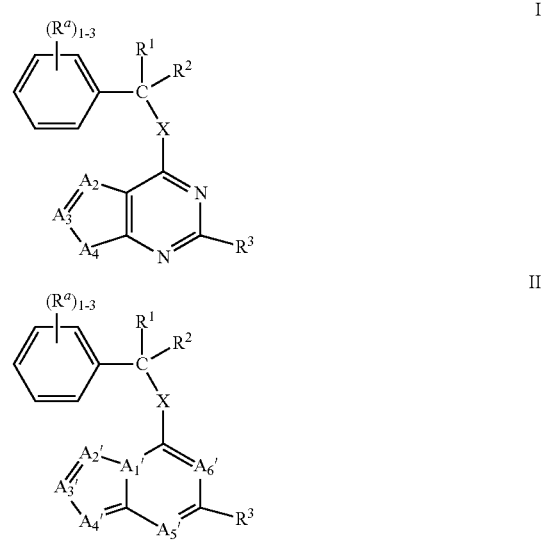

or a pharmaceutically acceptable salt thereof, wherein:
X represents NR, or O;
R is selected from the group consisting of H and $C_{1-6}$alkyl,
$A_2$, $A_3$, and $A_4$, are represented respectively as follows:
 1) $A_2$=N, $A_3$=CH, $A_4$=$NR^4$;
 2) $A_2$=CH, $A_3$=N, $A_4$=$NR^4$;
$A_{1'}$, $A_{2'}$, $A_{3'}$, $A_{4'}$, $A_{5'}$, and $A_{6'}$ are represented respectively as follows:
 1) $A_{1'}$=N, $A_{2'}$=N, $A_{3'}$=$CR^4$, $A_{4'}$=$CR^4$, $A_{5'}$=N, $A_{6'}$=CH;
 2) $A_{1'}$=N, $A_{2'}$=CH, $A_{3'}$=CH, $A_{4'}$=N, $A_{5'}$=N, $A_{6'}$=CH;
 3) $A_{1'}$=N, $A_{2'}$=CH, $A_{3'}$=CH, $A_{4'}$=N, $A_{5'}$=CH, $A_{6'}$=N;
 4) $A_{1'}$=N, $A_{2'}$=CH, $A_{3'}$=N, $A_{4'}$=N, $A_{5'}$=N, $A_{6'}$=CH;
$R^1$ and $R^2$ are independently selected from the group consisting of H and $C_{1-6}$alkyl, said alkyl optionally substituted with 1 to 3 groups of $R^a$;
or $R^1$ and $R^2$ can combine with the carbon to which they are attached to form a $C_{3-10}$cycloalkyl or $C_{3-10}$heterocycloalkyl, said cycloalkyl and heterocycloalkyl optionally substituted with 1 to 3 groups of $R^a$;
$R^3$ represents H, halo, $C_{1-6}$alkyl, $C_{1-4}$haloalkyl, $(CH_2)_nOR$, $C_{3-10}$cycloalkyl, $NR_2$, said alkyl and cycloalkyl optionally substituted with 1 to 3 groups of $R^a$;
$R^4$ is selected from the group consisting of hydrogen, $(CH_2)_nOR$, $C_{1-6}$alkyl, $(CH_2)_nC_{1-4}$haloalkyl, CN, and $NR_2$, said alkyl optionally substituted with one to three groups of $R^a$;
$R^a$ is selected from the group consisting of halo, CN, $C_{1-6}$alkyl, $(CH_2)_nOR$, $(O)_pC_{1-4}$haloalkyl, $NR_2$, $SCF_3$, $SF_5$, $C_{3-10}$cycloalkyl, $C_{6-10}$aryl, and $C_{4-10}$heterocyclyl;
n represents 0, 1, 2, 3, or 4;
p represents 0 or 1.

An embodiment of the invention of formulas I and II is realized when X is NR. A subembodiment of this aspect of the invention of formulas I and II is realized when X is NH. Another subembodiment of this aspect of the invention of formulas I and II is realized when X is $NCH_3$. Another subembodiment of this aspect of the invention of formulas I and II is realized when X is $NCH_2CH_3$.

Another embodiment of the invention of formulas I and II is realized when X is O.

Another embodiment of the invention of formulas I and II is realized when $R^4$ is hydrogen.

Another embodiment of the invention of formulas I and II is realized when $R^4$ is optionally substituted $C_{1-6}$alkyl. A subembodiment of this aspect of the invention of formulas I and II is realized when $R^4$ is $CH_3$, $(CH_2)_nOH$, $CH(CH_3)_2$, $CH_2C(CH_3)_2OH$, or $CH_2CH_3$.

Another embodiment of the invention of formulas I and II is realized when $R^4$ is $(CH_2)_nC_{1-4}$haloalkyl. A subembodiment of this aspect of the invention is realized when $R^4$ is selected from the group consisting of $(CH_2)_nCHF_2$, $(CH_2)_nCH_2F$, and $(CH_2)_nCF_3$.

Another embodiment of the invention of formulas I and II is realized when $R^4$ is $NR_2$. A subembodiment of this aspect of the invention is realized when $R^4$ is selected from the group consisting of $NH_2$, $N(CH_3)_2$, and $NHCH_3$.

Another embodiment of the invention of formulas I and II is realized when $R^4$ is CN.

Another embodiment of the invention of formula I is realized when $A_2$, $A_3$, and $A_4$, are represented respectively as follows: $A_2=N$, $A_3=CH$, $A_4=NR^4$. A subembodiment of this aspect of the invention of formula I is realized when $R^4$ is selected from the group consisting of H, $CH_3$, $CH(CH_3)_2$, $C(CH_3)_2OH$, $C(CH_3)_3$, $CH_2CH_3$, $CH_2CH(CH_3)OH$, $CH(CH_3)OH$, $(CH_2)_nOH$, $CHF_2$, $CH_2F$, $CH_2CF_3$, $CF_3$, $NH_2$, and CN. Another subembodiment of this aspect of the invention is realized when $R^4$ is selected from the group consisting of H and $CH_3$.

Another embodiment of the invention of formula I is realized when $A_2$, $A_3$, and $A_4$, are represented respectively as follows: $A_2=CH$, $A_3=N$, $A_4=NR^4$. A subembodiment of this aspect of the invention of formula I is realized when $R^4$ is selected from the group consisting of H, $CH_3$, $CH(CH_3)_2$, $C(CH_3)_2OH$, $C(CH_3)_3$, $CH_2CH_3$, $CH_2CH(CH_3)OH$, $CH(CH_3)OH$, $(CH_2)_nOH$, $CHF_2$, $CH_2F$, $CH_2CF_3$, $CF_3$, $NH_2$, and CN. Another subembodiment of this aspect of the invention is realized when $R^4$ is selected from the group consisting of H and $CH_3$.

Another embodiment of the invention of formula II is realized when $A_{1'}$, $A_{2'}$, $A_{3'}$, $A_{4'}$, $A_{5'}$, and $A_{6'}$ are represented respectively as follows: $A_{1'}=N$, $A_{2'}=N$, $A_{3'}=CR^4$, $A_{4'}=CR^4$, $A_{5'}=N$, $A_{6'}=CH$. A subembodiment of this aspect of the invention of formula II is realized when $R^4$ is selected from the group consisting of H, $CH_3$, $CH(CH_3)_2$, $C(CH_3)_2OH$, $C(CH_3)_3$, $CH_2CH_3$, $CH_2CH(CH_3)OH$, $CH(CH_3)OH$, $(CH_2)_n$ OH, $CHF_2$, $CH_2F$, $CH_2CF_3$, $CF_3$, $NH_2$, and CN.

Another subembodiment of this aspect of the invention is realized when $R^4$ is selected from the group consisting of H and $CH_3$.

Another embodiment of the invention of formula II is realized when $A_{1'}$, $A_{2'}$, $A_{3'}$, $A_{4'}$, $A_{5'}$, and $A_{6'}$ are represented respectively as follows: $A_{1'}=N$, $A_{2'}=CH$, $A_{3'}=CH$, $A_{4'}=N$, $A_{5'}=N$, $A_{6'}=CH$. A subembodiment of this aspect of the invention of formula II is realized when $R^4$ is selected from the group consisting of H, $CH_3$, $CH(CH_3)_2$, $C(CH_3)_2OH$, $C(CH_3)_3$, $CH_2CH_3$, $CH_2CH(CH_3)OH$, $CH(CH_3)OH$, $(CH_2)_n$ OH, $CHF_2$, $CH_2F$, $CH_2CF_3$, $CF_3$, $NH_2$, and CN. Another subembodiment of this aspect of the invention is realized when $R^4$ is selected from the group consisting of H and $CH_3$.

Another embodiment of the invention of formula II is realized when $A_{1'}$, $A_{2'}$, $A_{3'}$, $A_{4'}$, $A_{5'}$, and $A_{6'}$ are represented respectively as follows: $A_{1'}=N$, $A_{2'}=CH$, $A_{3'}=CH$, $A_{4'}=N$, $A_{5'}=CH$, $A_{6'}=N$. A subembodiment of this aspect of the invention of formula II is realized when $R^4$ is selected from the group consisting of H, $CH_3$, $CH(CH_3)_2$, $C(CH_3)_2OH$, $C(CH_3)_3$, $CH_2CH_3$, $CH_2CH(CH_3)OH$, $CH(CH_3)OH$, $(CH_2)_n$ OH, $CHF_2$, $CH_2F$, $CH_2CF_3$, $CF_3$, $NH_2$, and CN. Another subembodiment of this aspect of the invention is realized when $R^4$ is selected from the group consisting of H and $CH_3$.

Another embodiment of the invention of formula II is realized when $A_{1'}$, $A_{2'}$, $A_{3'}$, $A_{4'}$, $A_{5'}$, and $A_{6'}$ are represented respectively as follows: $A_{1'}=N$, $A_{2'}=CH$, $A_{3'}=N$, $A_{4'}=N$, $A_{5'}=N$, $A_{6'}=CH$. A subembodiment of this aspect of the invention of formula II is realized when $R^4$ is selected from the group consisting of H, $CH_3$, $CH(CH_3)_2$, $C(CH_3)_2OH$, $C(CH_3)_3$, $CH_2CH_3$, $CH_2CH(CH_3)OH$, $CH(CH_3)OH$, $(CH_2)_n$ OH, $CHF_2$, $CH_2F$, $CH_2CF_3$, $CF_3$, $NH_2$, and CN. Another subembodiment of this aspect of the invention is realized when $R^4$ is selected from the group consisting of H and $CH_3$.

Yet another embodiment of the invention of formulas I and II is realized when $R^1$ and $R^2$ are selected from the group consisting of H, $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, $OCH_2CH_3$, and $(CH_2)_nOCH_3$. A subembodiment of this aspect of the invention of formulas I and II is realized when one of $R^1$ and $R^2$ is hydrogen. Another subembodiment of this aspect of the invention of formulas I and II is realized when both of $R^1$ and $R^2$ are hydrogen. Another subembodiment of the invention of formulas I and II is realized when one $R^1$ and $R^2$ is hydrogen and the other is selected from the group consisting of $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, $OCH_2CH_3$, and $(CH_2)_nOCH_3$. Still another subembodiment of the invention of formulas I and II is realized when one $R^1$ and $R^2$ is hydrogen and the other is selected from the group consisting of $CH_3$, $CH(CH_3)_2$, $C(CH_3)_2OH$, $C(CH_3)_3$, $(CH_2)_nOH$, and $(CH_2)_nOCH_3$. Still another subembodiment of the invention of formulas I and II is realized when one $R^1$ and $R^2$ is hydrogen and the other is $CH_3$.

Yet another embodiment of the invention of formulas I and II is realized when $R^1$ and $R^2$ combine with the carbon to which they are attached to form optionally substituted $C_{3-10}$cycloalkyl or $C_{3-10}$heterocycloalkyl. In particular embodiments $R^1$ and $R^2$ are attached to form cyclopropyl, cyclobutyl, cyclopentyl, cyclohexyl, or oxetanyl. A subembodiment of this aspect of the invention of formulas I and II is realized when $R^1$ and $R^2$ combine with the carbon to which they are attached to form optionally substituted cyclopropyl or cyclobutyl.

Another embodiment of the invention of formulas I and II is realized when $R^3$ is selected from the group consisting of H, halo, OH, $(CH_2)_nCH_3$, $CH(CH_3)_2$, $C(CH_3)_3$, $(CH_2)_nOCH_3$, $CH_2F$, $CHF_2$, $(CH_2)_nCF_3$, CN, and optionally substituted cyclopropyl. A subembodiment of this aspect of the invention is realized when $R^3$ is selected from the group consisting of $CH_3$, $CH(CH_3)_2$, $C(CH_3)_3$, $(CH_2)_nOCH_3$, $CH_2F$, $CHF_2$, and $CF_3$. Still another subembodiment of this aspect of the invention is realized when $R^3$ is selected from the group consisting of $CH_3$, and $CF_3$.

Another embodiment of the invention of formulas I and II is realized when $R^a$ is selected from H, OH, halo, $(CH_2)_nCH_3$, $CH(CH_3)_2$, $C(CH_3)_3$, $(CH_2)_nOCH_3$, $CH_2F$, $CHF_2$, $(CH_2)_nCF_3$, $OCHF_2$, $OCF_3$, $SCF_3$, $SF_5$, $CH_2NH_2$, $(CH_2)_nN(CH_3)_2$, phenyl, cyclobutyl, and cyclopropyl.

Another embodiment of the invention of formulas I and II is realized when n is 0. Another embodiment of the invention of formula I is realized when n is 1. Another embodiment of the invention formulas I and II is realized when n is 2. Another embodiment of the invention of formula I is realized when n is 3. Still another embodiment of the invention of formulas I and II is realized when n of $R^a$ is 0-1, 0-2, or 0-3.

Another embodiment of the invention is realized when it is represented by structural formula Ia:

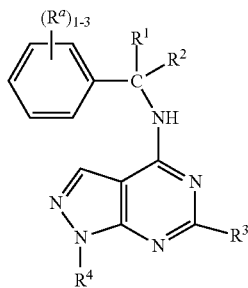

Ia or a pharmaceutically acceptable salt thereof wherein $R^1$, $R^2$, $R^3$ and $R^a$ are as originally described. An embodiment of the invention of formula Ia is realized when $R^a$ is selected from halo, $(CH_2)_nCF_3$, $OCF_3$, $C(CH_3)_3$, $OC(CH_3)_3$, $CHF_2$, $SOCH_3$, $SF_5$, $SCF_3$, $OCHF_2$, and $CH(CH_3)_2$, $R^4$ is selected from the group consisting of H, $(CH_2)_nOH$, $CH(CH_3)_2$, $CH_3$, and $CH_2CF_3$, $R^3$ is selected from the group consisting of H, halo, OH, $(CH_2)_nCH_3$, $CH(CH_3)_2$, $C(CH_3)_3$, $(CH_2)_nOCH_3$, $CH_2F$, $CHF_2$, $(CH_2)_nCF_3$, CN, and optionally substituted cyclopropyl, and $R^1$ and $R^2$ are selected from the group consisting of H, $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, $OCH_2CH_3$, and $(CH_2)_nOCH_3$.

A subembodiment of this aspect of the invention of formula Ia is realized when $R^a$ is selected from the group consisting of halo, $(CH_2)_nCF_3$, and $OCF_3$, $R^3$ is selected from the group consisting of H, halo, OH, $(CH_2)_nCH_3$, $CH(CH_3)_2$, $C(CH_3)_3$, $(CH_2)_nOCH_3$, $CH_2F$, $CHF_2$, $(CH_2)_nCF_3$, CN, and optionally substituted cyclopropyl, $R^4$ is selected from the group consisting of H, and $CH_3$, and one of $R^1$ and $R^2$ is hydrogen and the other is selected from the group consisting of $CH_3$, $CH(CH_3)_2$, $C(CH_3)_2OH$, $C(CH_3)_3$, $(CH_2)_nOH$, and $(CH_2)_nOCH_3$.

A subembodiment of this aspect of the invention of formula Ia is realized when $R^a$ is selected from the group consisting of halo, $(CH_2)nCF_3$, and $OCF_3$, $R^4$ is selected from the group consisting of H, and $CH_3$, and one of $R^1$ and $R^2$ combine with the carbon to which they are attached to form optionally substituted cyclopropyl, cyclobutyl, cyclopentyl, cyclohexyl, or oxetanyl. A subembodiment of this aspect of the invention of formula Ia is realized when $R^1$ and $R^2$ combine with the carbon to which they are attached to form optionally substituted cyclopropyl or cyclobutyl.

Still another embodiment of the invention is realized when it is represented by structural formula IIa:

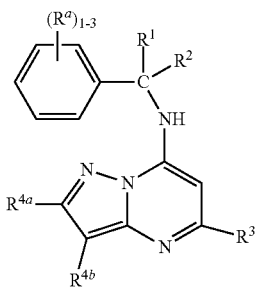

IIa or a pharmaceutically acceptable salt thereof wherein $R^1$, $R^2$, $R^3$ and $R^a$ are as originally described and $R^{4a}$ and $R^{4b}$ both equal $R^4$. An embodiment of the invention of formula IIa is realized when $R^a$ is selected from halo, $(CH_2)_nCF_3$, $OCF_3$, $C(CH_3)_3$, $OC(CH_3)_3$, $CHF_2$, $SOCH3$, $SF5$, $SCF_3$, $OCHF_2$, and $CH(CH_3)_2$, $R^3$ is selected from the group consisting of H, halo, OH, $(CH_2)_nCH_3$, $CH(CH_3)_2$, $C(CH_3)_3$, $(CH_2)_nOCH_3$, $CH_2F$, $CHF_2$, $(CH_2)_nCF_3$, CN, and optionally substituted cyclopropyl, $R^{4a}$ and $R^{4b}$ are selected from the group consisting of H, CN, $(CH_2)_nOH$, $CH_3$, $NH_2$, $N(CH_3)_2$, $NHCH_3$, and $R^1$ and $R^2$ are selected from the group consisting of H, $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, $OCH_2CH_3$, and $(CH_2)_nOCH_3$.

A subembodiment of this aspect of the invention of formula IIa is realized when $R^a$ is selected from the group consisting of halo, $(CH_2)_nCF_3$, and $OCF_3$, $R^3$ is selected from the group consisting of H, halo, OH, $(CH_2)_nCH_3$, $CH(CH_3)_2$, $C(CH_3)_3$, $(CH_2)_nOCH_3$, $CH_2F$, $CHF_2$, $(CH_2)_nCF_3$, CN, and optionally substituted cyclopropyl, one of $R^{4a}$ and $R^{4b}$ is hydrogen and the other is selected from the group consisting of CN, $(CH_2)_nOH$, $CH_3$, and $NH_2$, and one of $R^1$ and $R^2$ is hydrogen and the other is selected from the group consisting of $CH_3$, $CH(CH_3)_2$, $C(CH_3)_2OH$, $C(CH_3)_3$, $(CH_2)_nOH$, and $(CH_2)_nOCH_3$.

A subembodiment of this aspect of the invention of formula IIa is realized when $R^a$ is selected from the group consisting of halo, $(CH_2)nCF3$, and $OCF3$, one of $R^{4a}$ and $R^{4b}$ is hydrogen and the other is selected from the group consisting of CN, $(CH_2)_nOH$, $CH_3$, and $NH_2$, and $R^1$ and $R^2$ combine with the carbon to which they are attached to form optionally substituted cyclopropyl, cyclobutyl, cyclopentyl, cyclohexyl, or oxetanyl. A subembodiment of this aspect of the invention of formula Ia is realized when $R^1$ and $R^2$ combine with the carbon to which they are attached to form optionally substituted cyclopropyl or cyclobutyl.

The invention is also directed to a method for the treatment of central nervous system disorders associated with phosphodiesterase 2 (PDE2) using the compounds of Formula I. More specifically, the present invention relates to the use of such compounds for treating neurological and psychiatric disorders, such as schizophrenia, psychosis, Alzheimer's, cognitive impairment, anxiety, depression, migraines, Parkinson's disease, Parkinson's disease dementia (PDD), or Huntington's disease, and those associated with striatal hypofunction or basal ganglia dysfunction using the compounds of formula I, Ia, II and IIa.

Examples of compounds of the invention can be found throughout the specification.

The invention also encompasses pharmaceutical compositions containing a compound of formula I, Ia, II and IIa, and methods for treatment or prevention of phosphodiesterase mediated diseases using compounds of formula I, Ia, II and IIa.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds and valency is permissible.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein the term "heterocycloakyl" means a cycloalkyl containing heteroatom selected from N, S, O.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydroisobenzofuranyl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl. The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

When a heterocyclyl group as defined herein is substituted, the substituent may be bonded to a ring carbon atom of the hetercyclyl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo. The term "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —$CF_3$.

Where possible, compounds of this invention may exist in several tautomeric forms as be appreciated by any one skilled in the art. Previous researchers have studied similar compounds and found that one of these tautomers can exist as the predominant form depending on structures and conditions. See B. M. Giuliano, et al. J. Phys. Chem. A, 114, 12725-12730, 2010; B. M. Giuliano, et al. J. Phys. Chem. A, 115, 8178-8179, 2011; A. Gerega, et al. J. Phys. Chem. A, 111, 4934-4943, 2007; R. Sanchez, et al., J. Amer. Chem. Soc., 129(19), 6287-6290, 2007; C. Lopez, et al., Spectroscopy 14, 121-126, 2000; and G. M. Kheifets, et al., Russ. J. Org. Chem., 36(9), 1373-1387, 2000. For brevity and simplicity, we have represented the compounds of the present invention using Formula I and Ia and they are intended to represent all possible tautomeric forms for these compounds without regard to what actually is the predominant tautomeric form in existence for a particular compound.

The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates and the like. "Hydrate" is a solvate wherein the solvent molecule is $H_2O$.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of the compound bound to PDE2 enzyme, crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula I, Ia, II and IIa. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically enriched compounds within generic formula I and Ia can be prepared without undue experimentation by conventional techniques well known to those skilled in the art or by processes analogous to those described in the Schemes and Examples herein using appropriate isotopically enriched reagents and/or intermediates.

The term "substantially pure" means that the isolated material is at least 90% pure, and preferably 95% pure, and even more preferably 99% pure as assayed by analytical techniques known in the art.

For purposes of this specification, the following abbreviations have the indicated meanings:

Ac=acetyl
ACN=acetonitrile
AcO=acetate
BOC=t-butyloxycarbonyl
CBZ=carbobenzoxy
CDI=carbonyldiimidazole
DCC=1,3-dicyclohexylcarbodiimide
DCE=1,2-dichloroethane
DI=de-ionized
DIBAL=diisobutyl aluminum hydride
DIPEA or DIEA=N,N-diisoproylethylamine, also known as Hunig's base
DMA=dimethylacetamide
DMAP=4-(dimethylamino)pyridine
DMF=dimethylformamide
DMP=Dess-Martin periodinane
DPPA=Diphenylphosphoryl azide
DPPP=1,3-bis(diphenylphosphino)propane
Dtbbpy=4,4'-di-tert-butyl-2,2'-dipyridyl
EDC or EDCI=1-(3-dimethylaminopropyl)-3-ethylcarbodiimide hydrochloride
EDTA=ethylenediaminetetraacetic acid, tetrasodium salt
EtOAc or EA=ethyl acetate
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluronium hexafluorophosphate
HOAt=1-Hydroxy-7-azabenzotriazole
HOBt=1-hydroxybenzotriazole
HRMS=high resolution mass spectrometry
IBCF=isobutyl chloroformate
KHMDS=potassium hexamethyldisilazane
LC-MS=Liquid chromatography-mass spectrometry
LDA=lithium diisopropylamide
LiHMDS=lithium hexamethyldisilazane
MCPBA=metachloroperbenzoic acid
MMPP=magnesium monoperoxyphthlate hexahydrate
Ms=methanesulfonyl=mesyl
MsO=methanesulfonate=mesylate
MTBE=Methyl t-butyl ether
NBS=N-bromosuccinimide
NMM=4-methylmorpholine
NMP=N-methylpyrrolidinone
NMR=Nuclear magnetic resonance O/N=overnight
PCC=pyridinium chlorochromate
PDC=pyridinium dichromate
Ph=phenyl
PPTS=pyridinium p-toluene sulfonate
pTSA=p-toluene sulfonic acid
$PyH.Br_3$=pyridine hydrobromide perbromide
r.t./RT=room temperature
rac.=racemic T3P=2,4,6-Tripropyl-1,3,5,2,4,6-trioxatriphosphinane 2,4,6-trioxide
TBAF=tetrabutylammonium fluoride
TFA=trifluoroacetic acid
TfO=trifluoromethanesulfonate=triflate
THF=tetrahydrofuran
TLC=thin layer chromatography
TMSCl=trimethylsilyl chloride All patents, patent applications and publications cited herein, whether supra or infra, are hereby incorporated by reference in their entirety and are deemed representative of the prevailing state of the art.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE2 function or activity in a patient such as a mammal in need of such inhibition comprising the administration of an effective amount of the compound. In addition to primates, especially humans, a variety of other mammals can be treated according to the method of the present invention. The subject compounds may be useful in a method of inhibiting PDE2 activity in a patient such as a mammal in need of such inhibition comprising the administration of an effective amount of the compound. The subject compounds also may be useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE2 function in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1 inhibiting the disease state, i.e., arresting the development of the disease state or its clinical symptoms; 2) or relieving the disease state, i.e., causing temporary or permanent regression of the disease state or its clinical symptoms.

The invention is also directed to use of the compounds to prevent the disease state.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention.

Applicants propose that inhibitors of PDE2, including PDE2A, will provide therapeutic benefit to those individuals suffering from psychiatric and cognitive disorders. The unique and exclusive distribution of PDE2A in the medium spiny projection neurons of the striatum, which form the principle site for cortical and dopaminergic input within basal ganglia, suggests that it may be possible and desirable to identify inhibitors of PDE2 to enhance cellular signaling. Without wishing to be bound by any theory, applicants believe that inhibition of PDE2A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Parkinson's disease dementia (PDD), Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

In another embodiment of the compounds of this invention there is provided a method for treating or ameliorating diseases or conditions in neuronal development, learning, and memory, prolactin and aldosterone secretion, bone cell differentiation, growth, and bone resorption, immunological response, vascular angiogenesis, inflammatory cell transit, cardiac contraction, platelet aggregation, female sexual arousal disorder, and hypoxic pulmonary vasoconstriction.

As used herein, the term "'selective PDE2 inhibitor" refers to an organic molecule that effectively inhibits an enzyme from the PDE2 family to a greater extent than enzymes from the PDE 1, and 3-11 families. In one embodiment, a selective PDE2 inhibitor is an organic molecule having a Ki for inhibition of PDE2 that is less than or about one-tenth that for a substance that is an inhibitor for another PDE enzyme. In other words, the organic molecule inhibits PDE2 activity to the same degree at a concentration of about one-tenth or less than the concentration required for any other PDE enzyme. Preferably, a selective PDE2 inhibitor is an organic molecule, having a Ki for inhibition of PDE2 that is less than or about one-hundredth that for a substance that is an inhibitor for another PDE enzyme. In other words, the organic molecule inhibits PDE2 activity to the same degree at a concentration of about one-hundredth or less than the concentration required for any other PDE enzyme. Preferably, a selective PDE2 inhibitor is an organic molecule, having a Ki for inhibition of PDE2 that is less than or about five-hundredth that for a substance that is an inhibitor for another PDE enzyme. In other words, the organic molecule inhibits PDE2 activity to the same degree at a concentration of about five-hundredth or less than the concentration required for any other PDE enzyme. A "selective PDE2 inhibitor" can be identified, for example, by comparing the ability of an organic molecule to inhibit PDE2 activity to its ability to inhibit PDE enzymes from the other PDE families. For example, an organic molecule may be assayed for its ability to inhibit PDE2 activity, as well as PDE1A, PDE1B, PDE1C, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, PDE10 and/or PDE11A.

Phosphodiesterase enzymes including PDE2 have been implicated in a wide range of biological functions. This has suggested a potential role for these enzymes in a variety of disease processes in humans or other species. The compounds of the present invention may have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, *cannabis*, cocaine, hallucinogens, inhalants, opioids, phencyclidine, ketamine and other dissociative anesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Parkinson's disease dementia (PDD), Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-2 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder, mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, Parkinson's disease dementia (PDD), drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, idiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder, learning disorders, pervasive developmental disorders, including autistic disorder, attention disorders including Attention-Deficit/Hyperactivity Disorder, autism, tic disorders including Tourette's disorder, anxiety disorders including phobia and post-traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Angiogenesis is the physiological process through which new blood vessels form, and agents that inhibit this process have been shown to be effective treatments for some cancers. As initiation of angiogenesis involves migration and proliferation of vascular endothelial cells, and agents that elevate cAMP inhibit these processes, PDE2 inhibition may have utility as a treatment for cancer. See Savai, et al, *Targeting cancer with phosphodiesterase inhibitors*, Expert Opin. Investig. Drugs (2010) 19(1):117-131. PDE2 has been shown to be expressed in human vascular endothelial cells (VECs) and inhibition of PDE2 by treatment with selective inhibitors inhibited VEGF promoted migration of VECs. See Netherton and Maurice, *Vascular Endothelial Cell Cyclic Nucleotide Phosphodiesterases and Regulated Cell Migration: Implications in Angiogenesis*, Mol Pharmacol (2005) 67:263-272 and Favot, et al, *VEGF-induced HUVEC migration and proliferation are decreased by PDE2 and PDE4 inhibitors*. Thromb Haemost (2003) 90:334-343. Reduction of PDE2 activity with either small molecule inhibitors or PDE2A siRNA suppressed cell growth and invasion in a human malignant melanoma PMP cell line. See Hiramoto, et al, *Role of phosphodiesterase 2 in growth and invasion of human malignant melanoma cells*, Cellular Signalling (2014), 26:1807-1817. Reduction of PDE2 activity with a small molecule inhibitor attenuated tumor formation in a mouse model of ultraviolet light B-induced tumorigenesis. See Bernard, et al, *PDE2 is a Novel Target for Attenuating Tumor Formation in a Mouse Model of UVB-Induced Skin Carcinogenesis*, PLoS ONE (2014), 9(10):e109862. Thus, in another specific embodiment, compounds of the invention provide methods for treating, preventing, controlling, and/or reducing, attenuating cancers, such as malignant melanomas, skin cancer, and the like.

The subject compounds may be further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, AChEi's such as (Aricept (donepezil) and Exelon (rivastigmine) and NMDA blocker Namenda (memantine), beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg of body weight daily are administered to the patient, e.g., humans and elderly humans. The dosage range will generally be about 0.5 mg to 1.0 g per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods, schemes, and examples for preparing representative compounds of this invention are illustrated below and can be found in further detail in U.S. Pat. No. 7,144,913, which is incorporated by reference herein in its entirety. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. The compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood.

The representative examples of the compounds of the invention are illustrated in the following non-limiting schemes and Examples.

General

Starting materials used were obtained from commercial sources or prepared in other examples, unless otherwisely noted.

The progress of reactions was often monitored by TLC or LC-MS. The LC-MS was recorded using one of the following methods.

Method A: XBridge C18: 4.6×50 mm, 3.5 um, 1.0 uL injection, 1.50 mL/min flow rate, 90-900 amu scan range, 190-400 nm UV range, 10-95% (over 2.2 min) gradient with MeCN and water (5 µM NH$_4$HCO$_3$), hold 1 min; 3.6 minute total run time.

Method B: Supelco Ascentis Express C18, 3×50 mm, 2.7 um column. 2.0 uL injection, 1.25 mL/min flow rate, 170-900 amu scan range, 200-400 nm UV range, 10-99% (over 2.0 min) gradient with MeCN (0.05% TFA) and water (0.05%); 3 minute total run time.

Method C: Supelco Ascentis Express C18, 3×100 mm, 2.7 um column. 2.0 uL injection, 1.00 mL/min flow rate, 170-900 amu scan range, 200-400 nm UV range, 10-99% (over 4.0 min) gradient with MeCN (0.05% TFA) and water (0.05%); 5 minute total run time.

Method D: Waters Acquity UPLC, HSS C18 1.8 um, 2.1×50 mm, MeCN and water with 0.1% trifluoroacetic acid, 1 mL/min flow rate, gradient 5%-100% MeCN over 1.4 min.

Method E: Waters Acquity UPLC, HSS C18 1.8 um, 2.1×50 mm, MeCN and water with 0.1% formic acid, 1 mL/min flow rate, gradient 5%-100% MeCN over 1.4 min.

Method F: Shimadzu: 3.0×50 mm, 2.2 um, 1.0 uL injection, 1.00 mL/min flow rate, 90-900 amu scan range, 190-400 nm UV range, 5-100% (over 2.2 min) gradient with MeCN (0.05% TFA) and water (0.05% TFA), hold 1 min; 3.6 minute total run time.

Method G: Titan C18: 2.1×50 mm, 1.9 um, 1.0 uL injection, 0.80 mL/min flow rate, 90-900 amu scan range, 190-400 nm UV range, 5-100% (over 2.1 min) gradient with MeCN (0.05% TFA) and water (0.05% TFA), hold 0.5 min; 3.0 minute total run time.

Method H: ZORBAX Eclipse Plus C18: 3.0×50 mm, 1.8 um, 1.0 uL injection, 1.00 mL/min flow rate, 90-900 amu scan range, 190-400 nm UV range, 5-100% (over 2.1 min)

gradient with MeCN (0.1% FA) and water (0.1% FA), hold 0.5 min; 3.0 minute total run time.

NMR was recorded at room temperature unless noted otherwise on Varian Inova 400 or 500 MHz spectrometers with the solvent peak used as the reference or on Bruker 300 or 400 MHz spectrometers with the TMS peak used as internal reference.

The methods used for the preparation of the compounds of this invention are illustrated by the following schemes. Unless specified otherwise, all starting materials used are commercially available.

Scheme A

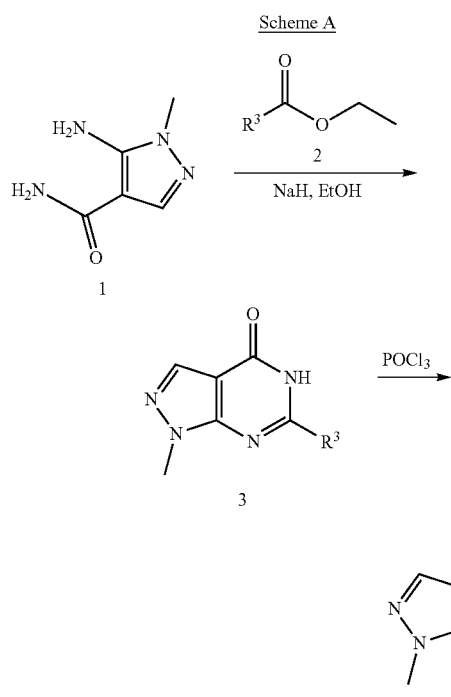

Scheme A illustrates the procedures for the syntheses of 6-substituted-4-chloro-1-methyl-1H-pyrazolo[3,4-d]pyrimidines such as 4. Reaction of 5-amino-1-methyl-1H-pyrazole-4-carboxamide 1 with ester 2 using a base such as NaH in ethanol gives the 6-substituted-1-methyl-1,5-dihydro-4H-pyrazolo[3,4-d]pyrimidin-4-one 3. Chlorination with phosphorous oxychloride affords the corresponding 6-substituted-4-chloro-1-methyl-1H-pyrazolo[3,4-d]pyrimidine 4.

Scheme B

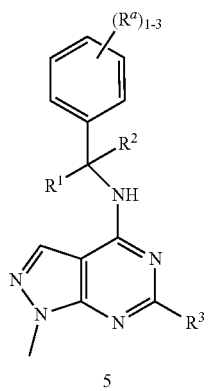

Scheme B outlines the $S_NAr$ displacement of the chloride intermediate 4, from the prior scheme, with various alpha-substituted amines that lead to compounds such as 5.

Scheme C

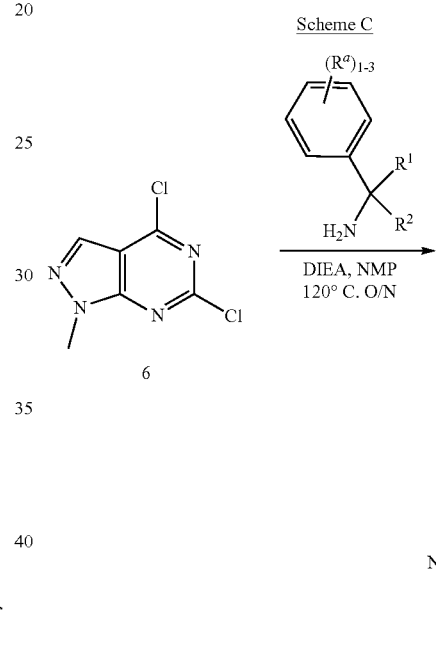

Scheme C illustrates the $S_NAr$ displacement on the commercially available di-chloro pyrazolopyrimidine 6 to afford final PDE2 analogues 7 with $R_3$ as the chloride, which provides a functional handle for further elaboration.

Scheme D

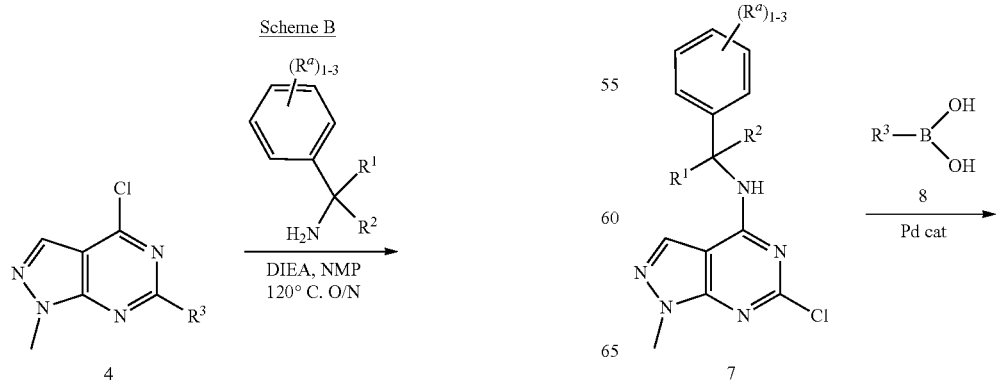

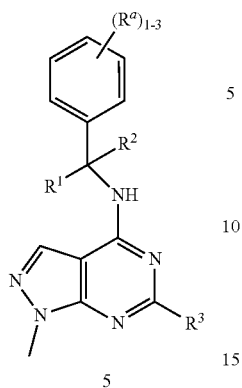

Scheme D outlines palladium catalyzed cross coupling of boronic acids 8 with chloro-intermediate 7 to afford other R³ substituted PDE2 compounds 5. An example of this could be using a boronic acid, such as cyclopropyl boronic acid, to afford R³ as the cyclopropyl substituted compound.

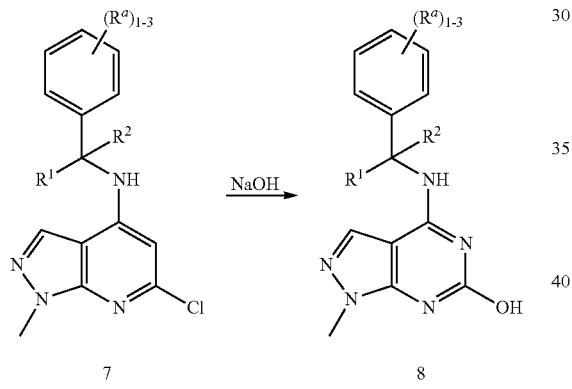

Scheme E demonstrates the displacement of the chloride to afford the hydroxyl compound via treatment with aqueous sodium hydroxide.

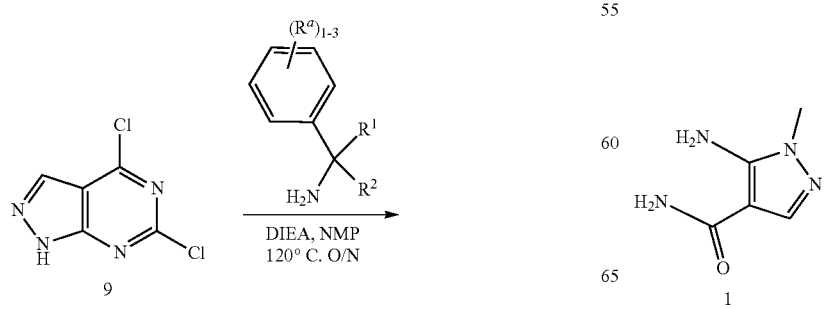

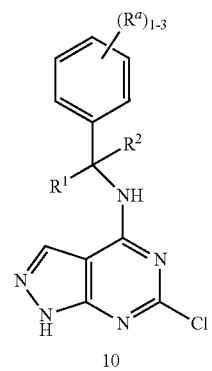

Scheme F illustrates the S$_N$Ar displacement on the commercially available N-unsubstituted di-chloro pyrazolopyrimidine 9 to afford analogues 10.

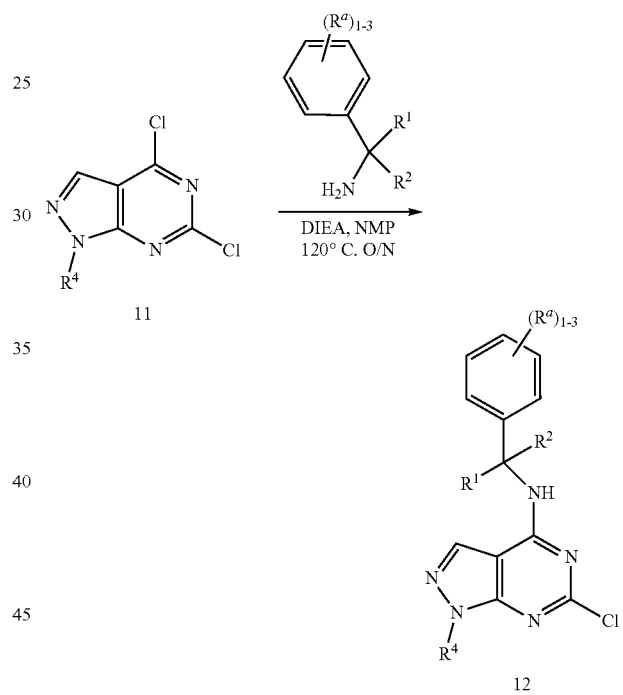

Scheme G demonstrates the S$_N$Ar displacement on the commercially available di-chloro pyrazolopyrimidine intermediates 11, in which R⁴ is other than H or methyl substitution, to afford final PDE2 analogues 12.

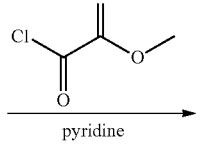

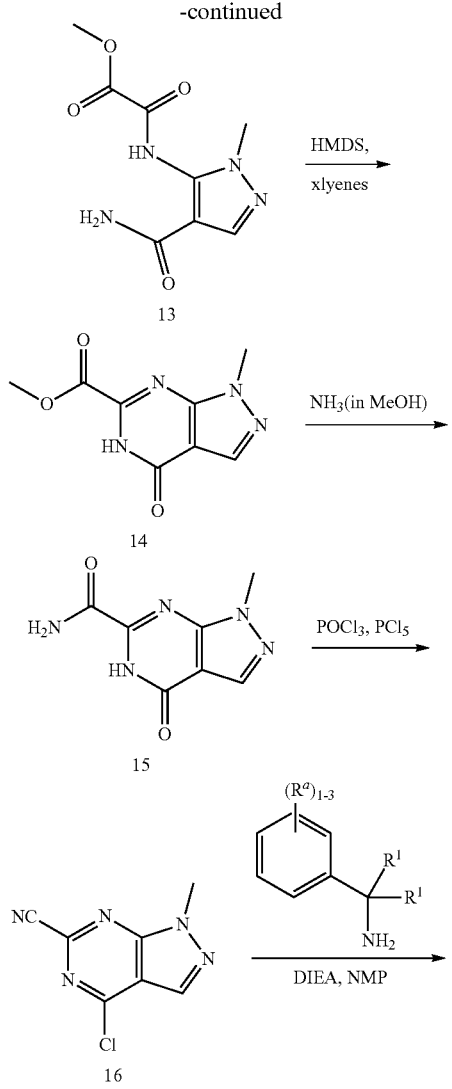

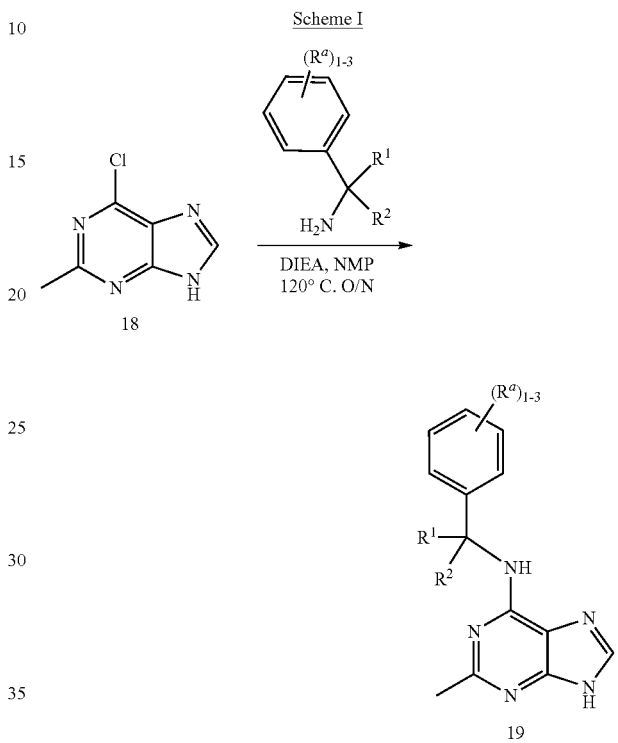

in-situ of the amide to the CN and the pyrimidone to the chloropyrimidine is accomplished by treating compound 15 with PCl₅ and using POCl₃ as solvent. Finally, $S_NAr$ displacement of the chloro-substituted pyrimidine 16 with various substituted benzyl amines affords final PDE2 analogues 17.

Scheme I outlines the $S_NAr$ displacement on the commercially available di-chloro imidazolopyrimidine intermediate 18 to afford final PDE2 analogues 19.

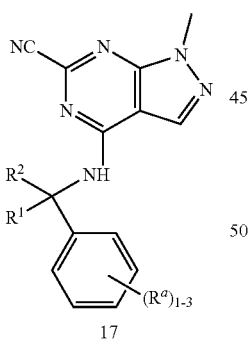

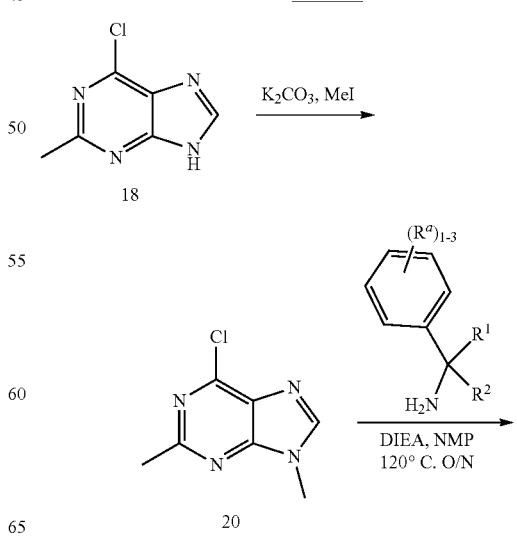

Scheme H illustrates the synthesis of 6-cyanosubstituted ($R_3$=CN) PDE2 final analogues 17. Reaction of 5-amino-1-methyl-1H-pyrazole-4-carboxamide 1 with methyl 2-chloro-2-oxoacetate using a base, such as pyridine, gives the 1H-pyrazole-4-carboxamide intermediate 13. The carboxamide 13 is then treated with hexamethyldisilazane in an appropiate high boiling point solvent, such as xylene, which is heated greater than 120° C. overnight to afford the pyrimidone-ester intermediate 14. The ester intermediate 14 is then converted to the primary amide 15 by heating in a solution of ammonia in methanol. Simultaneous conversion

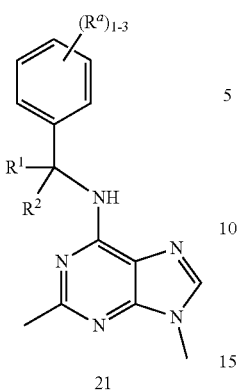

21

Scheme J illustrates the synthetic route to N-methyl imidazolopyrimidine PDE2 analogues 21. The chloro-imidazolopyrimidine 18 is first methylated via alkylation of the imidazole nitrogen with methyl iodide and an appropriate base, such as potassium carbonate, to afford 20. S$_N$Ar displacement, describe in several previous schemes, with substituted benzyl amines of the chloro imidazolopyrimidine 20 affords the final PDE2 analogues 21.

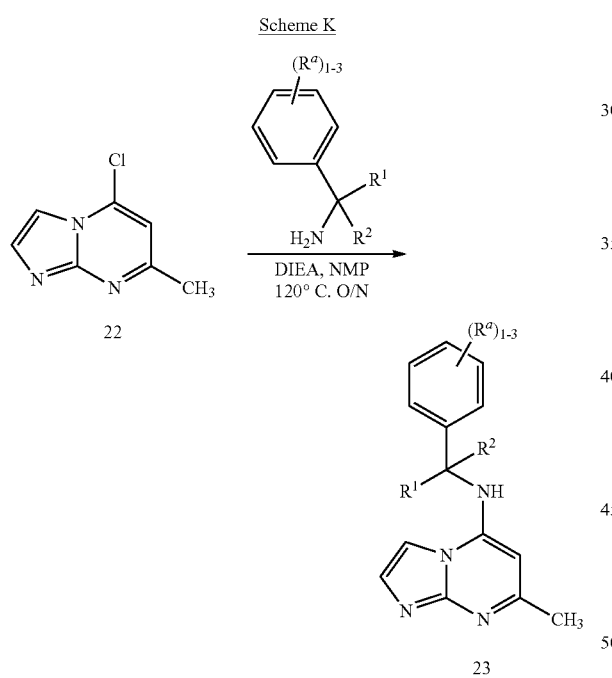

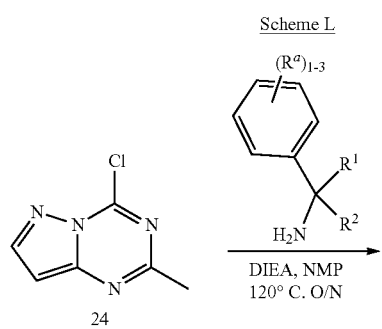

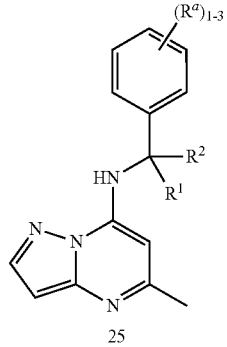

25

Scheme K and L represent another illustration of the standard S$_N$Ar displacement on chloro substituted intermediates, such as 22 and 24, to afford final PDE2 analogues 23 and 25.

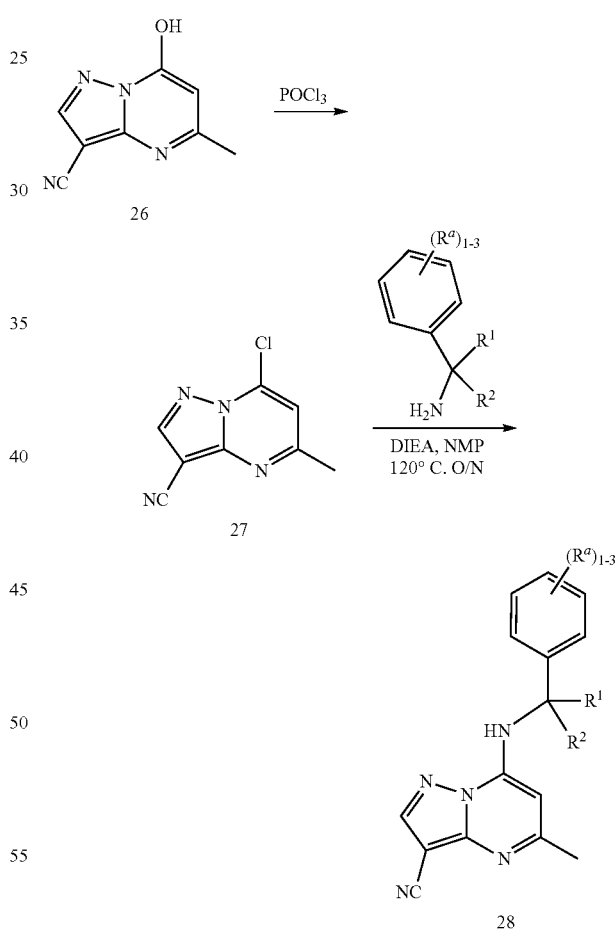

Scheme M outlines the preparation of analogues represent such as compound 28. The commercially available 7-hydroxy-5-methylpyrazolo[1,5-a]pyrimidine-3-carbonitrile 26 is treated with POCl$_3$ which affords the 7-chloro-5-methylpyrazolo[1,5-a]pyrimidine-3-carbonitrile intermediate 27. S$_N$Ar displacement of the chloro-substituted pyrimidine 27 with various substituted benzyl amines affords final PDE2 analogues such as 28.

Scheme N

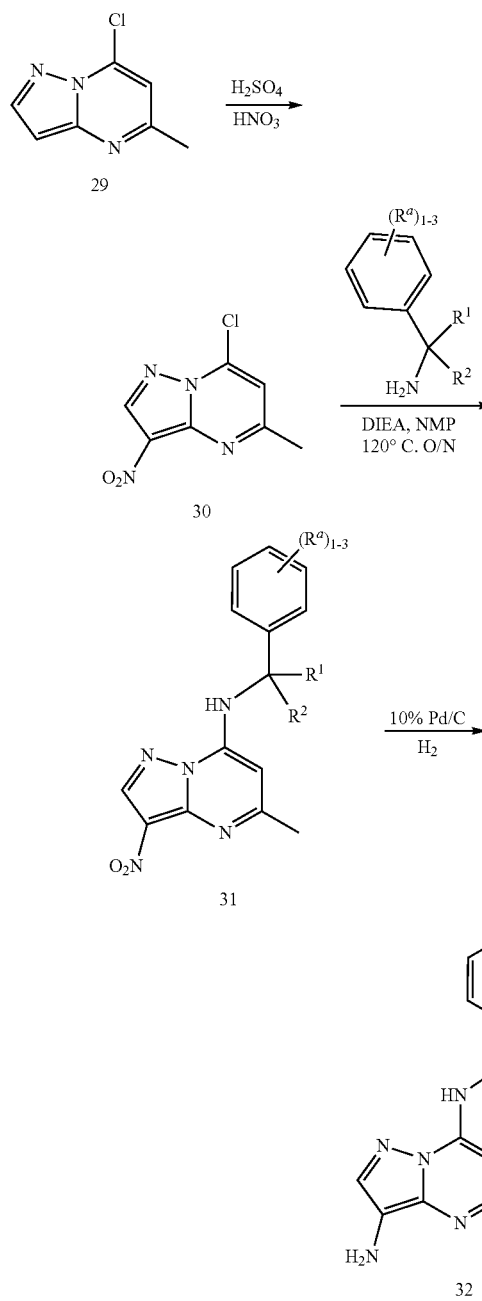

Scheme O

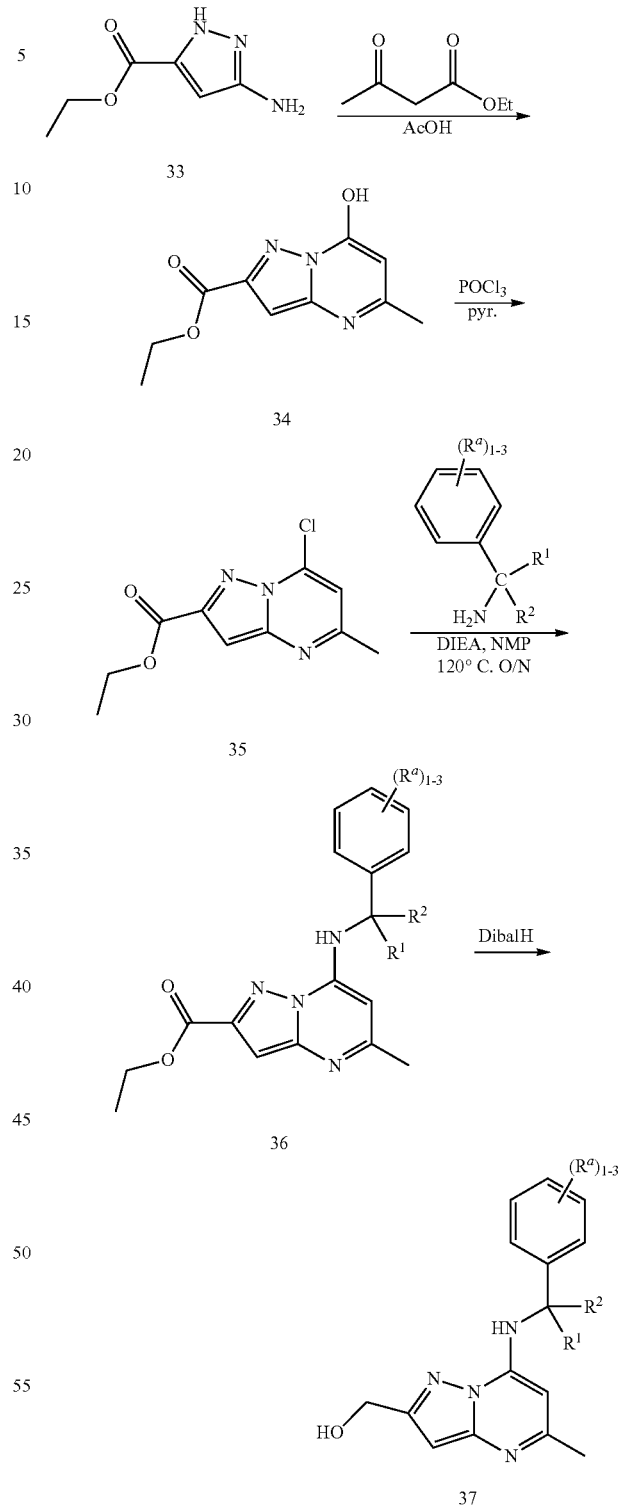

Scheme N illustrates the synthesis of 3-amino-substituted pyrazolopyrimidines as exemplified by compounds such as 32. Commercially available 7-chloro-5-methylpyrazolo[1,5-a]pyrimidine 29 is taken up into a suitable acid, such as concentrated sulfuric acid, and is then treated with fuming nitric acid, via dropwise addition, to form the 3-nitro substituted intermediate 30. $S_NAR$ displacement of the chloro-substituted pyrimidine 30 with various alpha-substituted amines affords compounds 31. Reduction of the nitro group via palladium on carbon in a suitable solvent, such as ethanol, under hydrogen atmosphere affords the final PDE2 analogues 32.

Scheme O illustrates the preparation of 2-hydroxymethyl analogs exemplified in compounds 37. Commercially available ethyl 3-amino-1H-pyrazole-5-carboxylate 33 is taken up in glacial acetic acid and is reacted with ethyl acetoacetate to give ethyl 7-hydroxy-5-methylpyrazolo[1,5-a]pyrimidine-2-carboxylate 34. Intermediate 34 is then treated with POCl₃ which affords the ethyl 7-chloro-5-methylpyrazolo[1,5-a]pyrimidine-2-carboxylate (35). S_NAr displacement of the chloro-substituted pyrimidine 35 with various substituted benzyl amines provides compounds 36. DIBAL-H reduction of the ethyl ester in a suitable solvent, such as THF, under inert atmosphere, such as N2, affords the final target compounds 37.

Scheme P

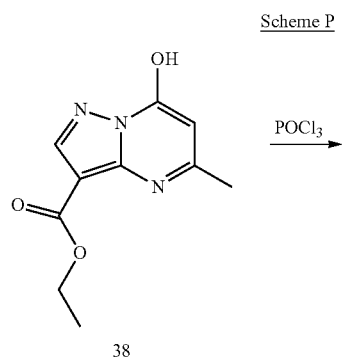

38

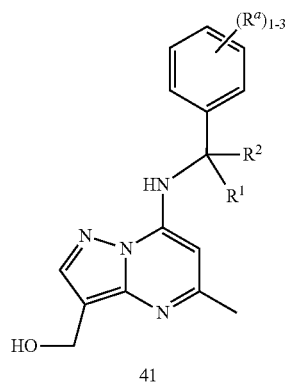

41

Scheme P demonstrates similar procedures as described in Scheme O; however, the starting intermediate is ethyl 7-hydroxy-5-methylpyrazolo[1,5-a]pyrimidine-3-carboxylate 38 and in this scheme the compounds that are synthesized are 3-hydroxymethyl analogs 41.

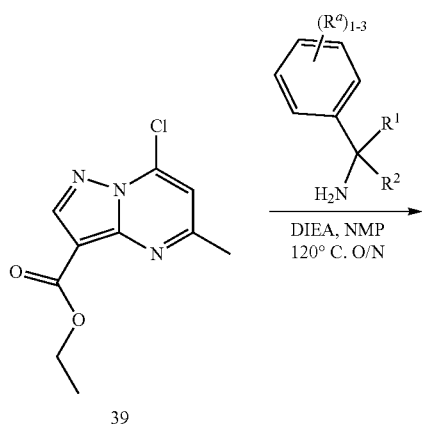

39

Scheme Q

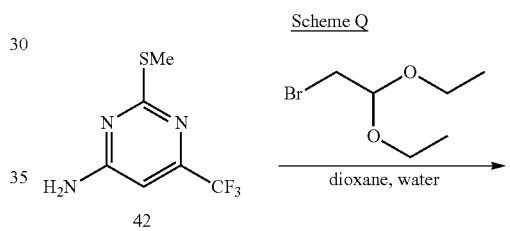

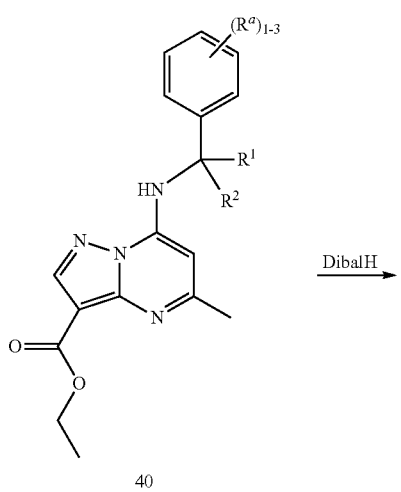

40

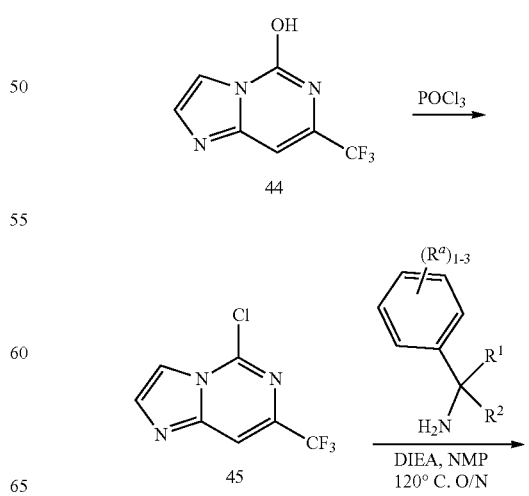

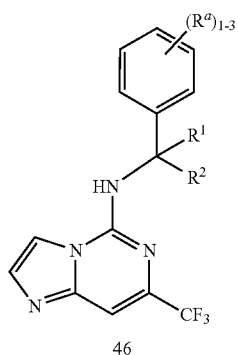

Scheme Q illustrates the synthesis of 7-trifluoromethyl substituted imidazolopyrimidine analogues 46. Commercially available 2-(methylthio)-6-(trifluoromethyl)pyrimidin-4-amine 42 is dissolved in an organic solvent, such as 1,4-dioxane, and mixed with a small amount of water. 2-Bromo-1,1-diethoxyethane is then added to this mixture and heated to afford 43. 5-(Methylthio)-7-(trifluoromethyl)imidazo[1,2-c]pyrimidine 43 is then refluxed in aqueous HCl for 16-24 hours to give compound 44. 7-(Trifluoromethyl)imidazo[1,2-c]pyrimidin-5-ol 44 is then treated with POCl$_3$ and the chloro intermediate 45 is then used for the $S_N Ar$ displacement with various alpha-substituted amines to provide compounds such as 46.

PREPARATORY EXAMPLES

Preparatory Example 1

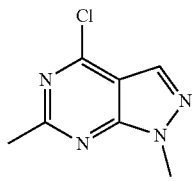

Step 1: 1,6-Dimethyl-1,5-dihydro-4H-pyrazolo[3,4-d]pyrimidin-4-one

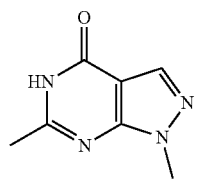

The suspension of 5-amine-1-methyl-1H-pyrazole-4-carboxamide (5 g, 35.70 mmol) in 100 mL of anhydrous 1,4-dioxane was cooled to 0° C., then Hunig's base (6.54 mL, 37.50 mmol) was added followed by dropwise addition of acetyl chloride (2.94 g, 35.70 mmol) over 10 minutes. This mixture was then stirred for 5 minutes at 0° C., and then an additional 10 min after removal of the ice water bath. The mixture was then heated to 70° C. and stirred at that temperature under nitrogen over the weekend. The mixture was then heated to 110° C. and stirred at that temperature for 4 h. Sodium carbonate (7.56 g, 71.40 mmol) was added slowly and the resulting suspension was stirred at 110° C. for 1 h. The mixture was then allowed to cooled down to room temperature and an aliquot was taken which analyzed by LCMS proved to have desired product and no starting material. The solvent was removed in vacuo and the residue was diluted with water and extracted with EtOAc (3×40 mL). The organics were combined, dried over sodium sulfate, filtered, and the filtrate concentrated to dryness under reduced pressure to afford the crude title compound as a solid. LC/MS (m/z): 165.1 (M+H)$^+$. $^1$H NMR (500 MHz, MeOH-d$_4$) δ: 8.02 (s, 1H), 3.95 (s, 3H), 1.64 (s, 3H).

Step 2: 4-Chloro-1,6-dimethyl-1H-pyrazolo[3,4-d]pyrimidine

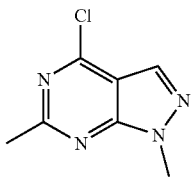

A 250 mL round bottom flask was charged with 1,6-dimethyl-1,5-dihydro-4H-pyrazolo[3,4-d]pyrimidin-4-one (850 mg, 5.18 mmol) and 15 mL of POCl$_3$ was added along with 5 mL of DMF. The resulting mixture was then heated to 95° C. and the heterogeneous mixture turned a translucent brown homogenous solution during heating. This mixture was then stirred at 95° C. for 2 h upon which LCMS proved the reaction was complete. The mixture was allowed to cool down to room temperature and then quenched with 50 mL of ice water. The solution was then extracted with EtOAc (2×100 mL) and the combined EtOAc layers were dried on Na$_2$SO$_4$, filtered, and filtrate was concentrate in vacuo to give crude desired product as a solid. LC/MS (m/z): 183.1 (M+H)$^+$ and 185.1 (M+2+H)$^+$.

Preparatory Example 2

Ethyl 7-chloro-5-methylpyrazolo[1,5-a]pyrimidine-2-carboxylate

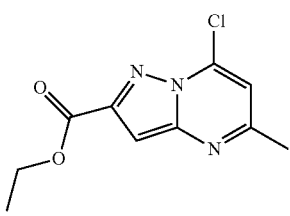 [SMILES: CCOC(=O)c1cc2nc(C)cc(Cl)n2n1]

Step 1: Ethyl 7-hydroxy-5-methylpyrazolo[1,5-a]pyrimidine-2-carboxylate

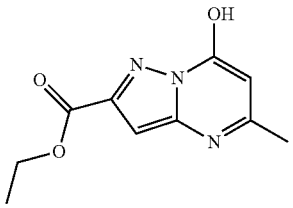 [SMILES: CCOC(=O)c1cc2nc(C)cc(O)n2n1]

To a solution of ethyl 3-amino-1H-pyrazole-5-carboxylate (1.5 g, 9.67 mmol) in glacial acetic acid (10 mL) at RT was added ethyl acetoacetate (1.33 mL, 10.6 mmol) dropwise. The mixture was refluxed at 100° C. for 12 h, cooled to RT, and concentrated under reduced pressure to afford a crude solid. DCM (10 mL) was added to the solid and was stirred at RT vigorously for 15 min. The mixture was filtered and resulting solid was washed with DCM (5 mL) and ether (10 mL). The solid was dried under vacuum to afford the title compound: LC/MS (m/z): 222.1 (M+H)+.

Step 2: Ethyl 7-chloro-5-methylpyrazolo[1,5-a]pyrimidine-2-carboxylate

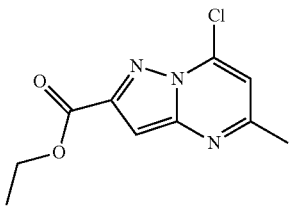

To a solution of ethyl 7-hydroxy-5-methylpyrazolo[1,5-a]pyrimidine-2-carboxylate (1.0 g, 4.52 mmol) in POCl$_3$ (5 mL) under N$_2$ was added pyridine (0.18 mL, 2.26 mmol) dropwise. The mixture was stirred at 85° C. for 1 h and then at 120° C. for 1 h. The mixture was cooled to RT whereupon chloroform (5 mL) was added and the solution was refluxed for 1 h. The mixture was cooled to RT and was poured onto the ice. The solution was extracted with CHCl$_3$ (3×80 mL) and the organic layers were combined. The organic layer was dried over Na$_2$SO$_4$, filtered, and concentrated under reduced pressure. The residue was purified by silica gel column chromatography (0-100% EtOAc in hexanes) to afford the title compound as a solid. LC/MS (m/z): 240.0 (M+H)+.

Preparatory Example 3

Ethyl 7-chloro-5-methylpyrazolo[1,5-a]pyrimidine-3-carboxylate

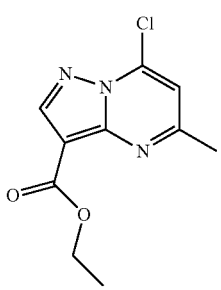 [SMILES: CCOC(=O)c1cnn2c(Cl)cc(C)nc12]

To a solution of ethyl 7-hydroxy-5-methylpyrazolo[1,5-a]pyrimidine-3-carboxylate (500 mg, 2.26 mmol) [CAS #58347-55-0] in POCl$_3$ (2 mL) under N$_2$ was added N,N-dimethylaniline (0.29 mL, 2.26 mmol) dropwise. The mixture was heat to reflux, stirred for 1 h, and was recooled to RT. The mixture was poured onto ice and was extracted with CHCl$_3$ (3×50 mL). The organic layers were combined, dried over Na$_2$SO$_4$, filtered, and concentrated under reduced pressure. The residue was purified by silica gel column chromatography (0-100% EtOAc/ethanol (3:1) in hexanes) to afford the title compound as a white solid. LC/MS (m/z): 240.0 (M+H)+.

Preparatory Example 4

5-Chloro-7-(trifluoromethyl)imidazo[1,2-c]pyrimidine

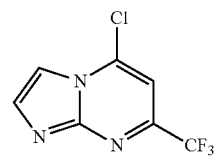 [SMILES: FC(F)(F)c1cc(Cl)n2ccnc2n1]

Step 1: 5-(Methylthio)-7-(trifluoromethyl)imidazo[1,2-c]pyrimidine

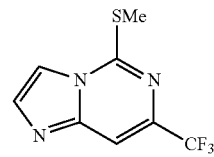

To a solution of 2-(methylthio)-6-(trifluoromethyl)pyrimidin-4-amine (0.900 g, 4.30 mmol) in 1,4-dioxane (8 mL) and water (2 mL) were added 2-bromo-1,1-diethoxyethane (1.19 g, 6.02 mmol). The reaction mixture was stirred at 100° C. for 3 h. The resulting mixture was cooled to room temperature and the solvent was removed under reduced pressure. The residue was purified by column chromatography over silica gel using gradient 1%-10% of MeOH in DCM as eluent. The title compound was obtained as a solid. MS (+ESI) m/z=234.0.

Step 2: 7-(Trifluoromethyl)imidazo[1,2-c]pyrimidin-5-ol

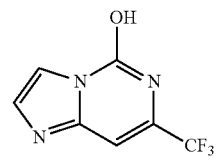

To 5-(methylthio)-7-(trifluoromethyl)imidazo[1,2-c]pyrimidine (0.500 g, 2.14 mmol) was added aqueous HCl (4 N, 6 mL). The reaction mixture was stirred at 100° C. for 24 h.

The resulting mixture was cooled to room temperature and concentrated under reduced pressure to afford the crude title compound as a solid which was used in next step directly without further purification. MS (+ESI) m/z=204.1.

Step 3: 5-Chloro-7-(trifluoromethyl)imidazo[1,2-c]pyrimidine

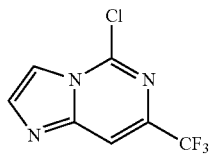

To 7-(trifluoromethyl)imidazo[1,2-c]pyrimidin-5-ol (0.150 g, 0.738 mmol) was added POCl₃ (3 mL). The reaction mixture was stirred at 100° C. for 3 h. The resulting mixture was cooled to room temperature and concentrated under reduced pressure. The residue was quenched by addition of ice-water (50 mL) and extracted with ethyl acetate (3×100 mL). The combined organic layers were washed with brine (100 mL), dried over anhydrous sodium sulfate and filtered. The filtrate was concentrated under reduced pressure. The residue was purified by column chromatography over silica gel using gradient 1%-10% of ethyl acetate in petroleum ether as eluent. The title compound was obtained as a solid. MS (+ESI) m/z=222.1; 224.1 (M+2+H)⁺.

EXAMPLES

Example 1

6-Chloro-1-methyl-N-{1-[4-(trifluoromethyl)phenyl]ethyl}-1H-pyrazolo[3,4-d]pyrimidin-4-amine

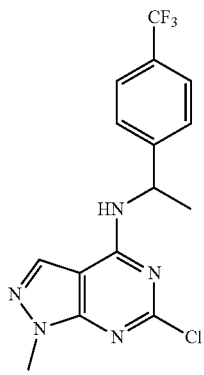

To a solution of commercially available 4,6-dichloro-1-methyl-1H-pyrazolo[3,4-d]pyrimidine (50 mg, 0.246 mmol) and 1-(4-(trifluoromethyl)phenyl)ethanamine (51.2 mg, 0.271 mmol) in THF (2463 µL) was added TEA (51.5 µl) and the resulting mixture stirred at 50° C. for 40 minutes. Desired product was seen after 40 minutes via aliquot analyzed by LCMS and it was observed that about 75% desired product formed. The reaction was allowed to stir at 50° C. overnight to ensure completion. The mixture was cooled to room temperature and the mixture concentrated under reduced pressure. The residue was purified on ISCO normal phase (12 g silica gel gold Redi-Sep column, 0-5% MeOH in DCM) to afford the title compound as a solid. LC-MS (+ESI) m/z=356.1 and 358.0 (M+2+H)⁺. ¹H NMR (500 MHz, MeOH-d₄) δ: 7.68-7.60 (m, 2H), 7.57-7.48 (m, 2H), 5.35 (s, 1H), 4.18-4.09 (m, 1H), 3.96 (s, 3H), 1.65 (s, 3H).

The following compounds in Table 1 were prepared using procedures similar to those described in Example 1 using appropriate starting materials.

TABLE 1

| Example No. | Structure | IUPAC Name | Observed Exact Mass [M + H]⁺ |
|---|---|---|---|
| 2 | 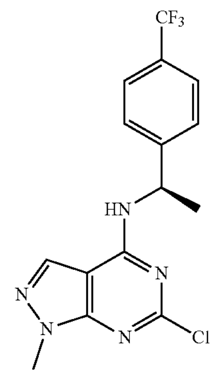 [SMILES: C[C@@H](Nc1nc(Cl)nc2c1cnn2C)c1ccc(C(F)(F)F)cc1] | 6-Chloro-N-{(1R)-1-[4-(trifluoromethyl)phenyl]ethyl}-1H-pyrazolo[3,4-d]pyrimidin-4-amine | 356.2 358.0 (M + 2 + H)⁺ |
| 3 | 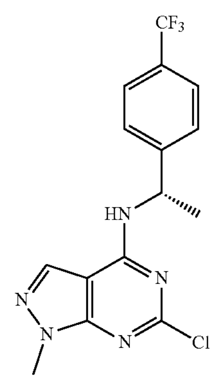 [SMILES: C[C@H](Nc1nc(Cl)nc2c1cnn2C)c1ccc(C(F)(F)F)cc1] | 6-Chloro-N-{(1S)-1-[4-(trifluoromethyl)phenyl]ethyl}-1H-pyrazolo[3,4-d]pyrimidin-4-amine | 356.2 358.1 (M + 2 + H)⁺ |
| 4 | 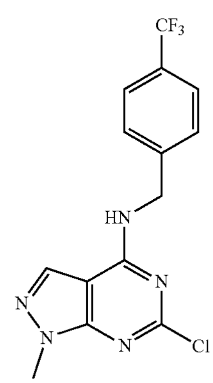 [SMILES: Cn1ncc2c(NCc3ccc(C(F)(F)F)cc3)nc(Cl)nc21] | 6-Chloro-1-methyl-N-[4-(trifluoromethyl)benzyl]-1H-pyrazolo[3,4-d]pyrimidin-4-amine | 342.2 344.2 (M + 2 + H)⁺ |

TABLE 1-continued

| Example No. | Structure | IUPAC Name | Observed Exact Mass [M + H]+ |
|---|---|---|---|
| 5 | 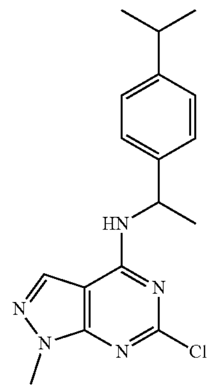 [SMILES: CC(C)c1ccc(C(C)Nc2nc(Cl)nc3c2cnn3C)cc1] | 6-Chloro-1-methyl-N-{1-[4-(1-methylethyl)-phenyl]ethyl}-1H-pyrazolo[3,4-d]pyrimidin-4-amine | 330.4 332.3 (M + 2 + H)+ |
| 6 | 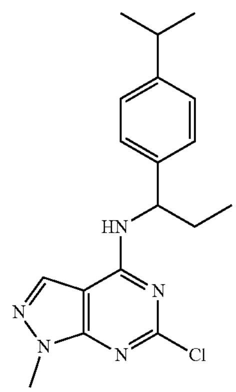 [SMILES: CCC(Nc1nc(Cl)nc2c1cnn2C)c1ccc(C(C)C)cc1] | 6-Chloro-1-methyl-N-{1-[4-(1-methylethyl)-phenyl]propyl}-1H-pyrazolo[3,4-d]pyrimidin-4-amine | 344.3 346.2 (M + 2 + H)+ |
| 7 | 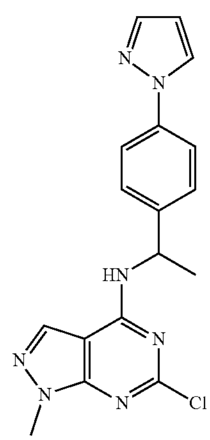 [SMILES: CC(Nc1nc(Cl)nc2c1cnn2C)c1ccc(-n2cccn2)cc1] | 6-Chloro-1-methyl-N-{1-[4-(1H-pyrazol-1-yl)phenyl]ethyl}-1H-pyrazolo[3,4-d]-pyrimidin-4-amine | 354.2 356.1 (M + 2 + H)+ |
| 8 | 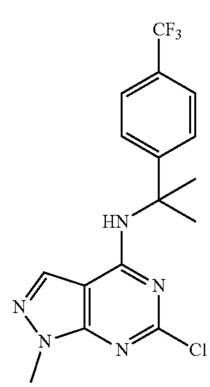 [SMILES: Cn1ncc2c(NC(C)(C)c3ccc(C(F)(F)F)cc3)nc(Cl)nc21] | 6-Chloro-1-methyl-N-{1-methyl-1-[4-(trifluoromethyl)-phenyl]ethyl}-1H-pyrazolo[3,4-d]-pyrimidin-4-amine | 370.4 372.4 (M + 2 + H)+ |

TABLE 1-continued

| Example No. | Structure | IUPAC Name | Observed Exact Mass [M + H]+ |
|---|---|---|---|
| 9 | 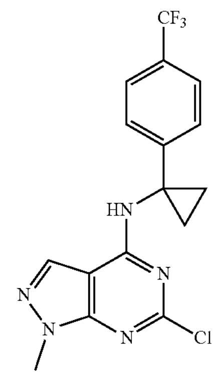 [SMILES: Cn1ncc2c(NC3(c4ccc(C(F)(F)F)cc4)CC3)nc(Cl)nc21] | 6-Chloro-1-methyl-N-{1-[4-(trifluoromethyl)-phenyl]cyclopropyl}-1H-pyrazolo[3,4-d]-pyrimidin-4-amine | 368.1 370.0 (M + 2 + H)+ |

Example 10

6-Chloro-N-{(1R)-[4-(trifluoromethyl)phenyl]ethyl}-1H-pyrazolo[3,4-d]pyrimidin-4-amine To a solution of commercially available 4,6-dichloro-1H-pyrazolo[3,4-d]pyrimidine (40 mg, 0.212 mmol) and (R)-1-[4-(trifluoromethyl)phenyl]ethan-1-amine (40 mg, 0.212 mmol) in THF (1500 µl) was added TEA (44.0 µl, 0.317 mmol) and the resulting mixture stirred at 50° C. overnight to ensure completion. The mixture was cooled to room temperature and the mixture concentrated under reduced pressure. The residue was purified on ISCO normal phase (12 g silica gel gold Redi-Sep column, 0-5% MeOH in DCM) and the fractions containing the product were combined. The solvent was removed under reduced pressure to afford the title compound as a solid. LC-MS (+ESI) m/z=343.1 and 345.0 (M+2+H)+. $^1$H NMR (500 MHz, MeOH-$d_4$) δ: 9.02 (d, J=6.2 Hz, 1H), 8.10 (d, J=6.3 Hz, 1H), 7.68-7.60 (m, 2H), 7.57-7.48 (m, 2H), 5.52-5.45 (m, 1H), 1.65 (s, 3H).

The following compound in Table 2 was prepared using procedures similar to those described in Example 10 using appropriate starting materials.

TABLE 2

| Example No. | Structure | IUPAC Name | Observed Exact Mass [M + H]+ |
|---|---|---|---|
| 11 | 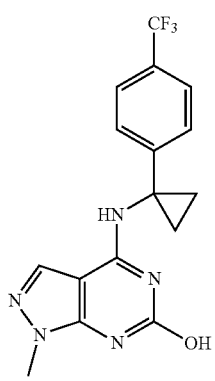 | 6-Chloro-N-{(1S)-[4-(trifluoromethyl)-phenyl]ethyl}-1H-pyrazolo[3,4-d]-pyrimidin-4-amine | 343.1, 345.1 (M + 2 + H)+ |

Example 12

1-Methyl-4-({1-[4-(trifluoromethyl)phenyl]cyclopropyl}amino)-1H-pyrazolo[3,4-d]pyrimidin-6-ol

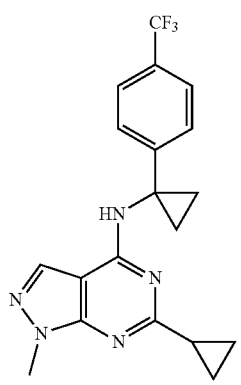 [SMILES: Cn1ncc2c(NC3(c4ccc(C(F)(F)F)cc4)CC3)nc(C3CC3)nc21]

The aryl chloride (Example 9, 30 mg, 0.082 mmol) and 1 M aqueous NaOH (0.41 mL, 5 equiv) were placed in a 0.5-2.0 mL microwave vial in dioxane (0.82 mL) and heated at 150° C. under microwave irradiation for 1 h. LCMS showed ~40% conversion. Heating was resumed at 150° C. under microwave irradiation for 2 h; no reaction progressed. An additional quantity of 1 M aqueous NaOH (0.41 mL, 5 equiv) was then added and heating was resumed at 150° C. under microwave irradiation for 2 h. LCMS showed ~70% conversion to the desired product. The reaction was concentrated under a stream of $N_2$ gas. The crude material was then purified by silica gel flash column chromatography (12 g cartridge), eluting with 0-5% MeOH/$CH_2Cl_2$ over 25 minutes to afford the final product as a solid. LC-MS (+ESI) m/z=350.3.

Example 13

6-Cyclopropyl-1-methyl-N-{1-[4-(trifluoromethyl)phenyl]cyclopropyl}-1H-pyrazolo[3,4-d]pyrimidin-4-amine

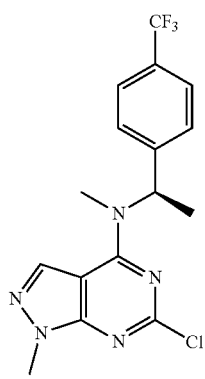 [SMILES: C[C@H](c1ccc(C(F)(F)F)cc1)N(C)c1nc(Cl)nc2c1cnn2C]

A vial was equipped with a magnetic stir bar and charged with the aryl halide (Example 9, 30 mg, 0.082 mmol), cyclopropylboronic acid (14.1 mg, 0.164 mmol), and $K_3PO_4$ (70 mg, 0.328 mmol). The mixture was then suspended in toluene (1 mL) and water (0.05 mL) and the Pd catalyst ($PdCl_2$(dppf), 9.2 mg, 0.012 mmol, 0.15 eq) was added and the resulting mixture was stirred at 100° C. After 2 h, the reaction was allowed to cool to room temperature, diluted with water (5 mL), and extracted with EtOAc (4×5 mL). Combined organic phases were dried over $MgSO_4$, filtered, and concentrated to give 90 mg of a brown oil. The crude material was purified by silica gel flash column chromatography (12 g cartridge), eluting with 0-5% MeOH/$CH_2Cl_2$ over 16 minutes. TLC in 50% EtOAc/hexanes gave an $R_f$ of 0.25 for the desired product, but no apparent separation from the impurity. The material was then purified by reverse phase HPLC. to provide the desired product: LC-MS (+ESI) m/z=374.2. $^1$H NMR (400 MHz, DMSO-$d_6$) δ: 8.05 (s, 1H), 7.62-7.55 (m, 2H), 7.47-7.38 (m, 2H), 2.52 (s, 3H), 1.52-1.43 (m, 2H), 1.21-1.05 (m, 4H), 0.81-0.74 (m, 2H).

Example 14

6-Chloro-N,1-dimethyl-N-{(1R)-1-[4-(trifluoromethyl)phenyl]ethyl}-1H-pyrazolo[3,4-d]pyrimidin-4-amine 4,6-Dichloro-1-methyl-1H-pyrazolo[3,4-d]pyrimidine (20 mg, 0.099 mmol), N-methyl-1-(4-(trifluoromethyl)phenyl)ethanamine (20.02 mg, 0.099 mmol) and TEA (20.60 μL) were stirred in THF (985 μL) at 50° C. for 2.5 h. The mixture was then allowed to cool to room temperature and was concentrated under reduced pressure to remove all solvent. The residue was then purified on ISCO normal phase system (12 g silica gel, gold Redi-Sep column, 30-40% EtOAc in hexanes) to afford the title compound as a solid. LC-MS (+ESI) m/z=370.0 and 372.0 (M+2+H)⁺. ¹H NMR (400 MHz, DMSO-d₆) δ: 8.06 (s, 1H), 7.68-7.62 (m, 2H), 7.57-7.50 (m, 2H), 6.62 (br. s, 1H), 3.95 (s, 3H), 3.05 (s, 3H), 1.67-1.60 (m, 3H).

The following compounds in Table 3 were prepared using procedures similar to those described in Example 14 using appropriate starting materials.

TABLE 3

| Example No. | Structure | IUPAC Name | Observed Exact Mass [M + H]⁺ |
|---|---|---|---|
| 15 | (structure with CF₃) | 6-Chloro-N,1-dimethyl-N-[4-(trifluoromethyl)benzyl]-1H-pyrazolo[3,4-d]pyrimidin-4-amine | 356.2 358.0 (M + 2 + H)⁺ |
| 16 | (structure with CF₃) | 6-Chloro-N-ethyl-1-methyl-N-[4-(trifluoromethyl)benzyl]-1H-pyrazolo[3,4-d]pyrimidin-4-amine | 370.2 372.2 (M + 2 + H)⁺ |

Example 17

6-Chloro-N,1-dimethyl-N-{1-[4-(trifluoromethyl)phenyl]cyclopropyl}-1H-pyrazolo[3,4-d]pyrimidin-4-amine

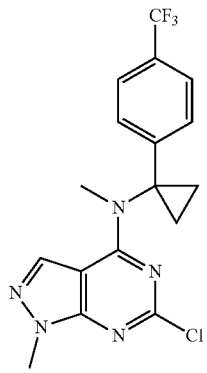 [SMILES: CN(c1nc(Cl)nc2c1cnn2C)C1(c2ccc(C(F)(F)F)cc2)CC1]

6-Chloro-1-methyl-N-(1-(4-(trifluoromethyl)phenyl)cyclopropyl)-1H-pyrazolo[3,4-d]pyrimidin-4-amine (Example 9, 15 mg, 0.041 mmol) was dissolved in DMF (408 μl) and NaH (1.6 mg, 0.041 mmol) was added followed by methyl iodide (2.55 μL, 0.041 mmol). The resulting mixture was then stirred at room temperature for 1 h. Several drops of water were then added slowly to the mixture and the material was then concentrated under reduced pressure. The residue was then purified by reverse phase HPLC (10-90% MeCN in H2O, 0.1% TFA, 12 min gradient) and the fractions containing the product were combined and diluted with aqueous sodium bicarbonate. The solution was extracted with DCM (3×5 mL). The organics were then combined, dried over magnesium sulfate, filtered, and the filtrate was concentrated under reduced pressure to afford the desired product as a solid. LC-MS (+ESI) m/z=382.4 and 384.4 (M+2+H)⁺.

Example 18

6-Chloro-1-(1-methylethyl)-N-{1-[4-(trifluoromethyl)phenyl]ethyl}-1H-pyrazolo[3,4-d]pyrimidin-4-amine

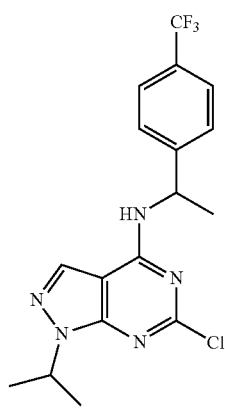 [SMILES: CC(Nc1nc(Cl)nc2c1cnn2C(C)C)c1ccc(C(F)(F)F)cc1]

Step 1: 4,6-Dichloro-1-isopropyl-1H-pyrazolo[3,4-d]pyrimidine

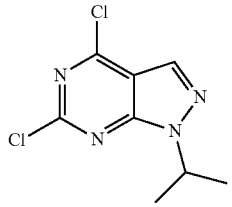

2,4,6-Trichloropyrimidine-5-carbaldehyde (50 mg, 0.236 mmol) was dissolved in dioxane (1 mL) and TEA (33 μL, 0.236 mmol) was added followed by hydrazine (35% wt in water, 14 μL, 0.189 mmol) and the resulting solution was heated in a 1 dram vial on a heating block at 110° C. for 2 hours. The resulting solution was then partitioned between water and EtOAc. The aqueous layer was extracted with 2 mL of EtOAc in the 1 dram vial. The organic layer was pipetted off and concentrated under a stream of nitrogen. This material was then used directly, without further purification, in $S_NAr$ reaction describe in the next step. LC-MS (+ESI) m/z=232.2 (M+H), 234.3 (M+2+H)$^+$, and 236.3 (M+4+H)$^+$.

Step 2: 6-Chloro-1-(1-methylethyl)-N-{1-[4-(trifluoromethyl)phenyl]ethyl}-1H-pyrazolo[3,4-d]pyrimidin-4-amine

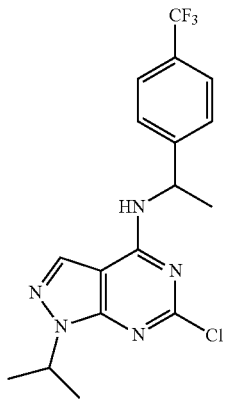 [SMILES: CC(Nc1nc(Cl)nc2c1cnn2C(C)C)c1ccc(C(F)(F)F)cc1]

A solution of 4,6-dichloro-1-isopropyl-1H-pyrazolo[3,4-d]pyrimidine (54 mg, 0.234 mmol) and TEA (100 μL, 0.72 mmol) in 1 mL THF was prepared. 1-[4-(Trifluoromethyl)phenyl]ethan-1-amine (88 mg, 0.468 mmol) was then added to the reaction mixture and it was stirred overnight at 50° C. on a heating block. The next day, the reaction mixture was transferred to a 13×100 mm test tube, and the THF was removed under a stream of nitrogen. The crude residue was then dissolved in DMSO (1 mL) and purified by mass-directed HPLC (2 cm×5 cm C18, acetonitrile-water gradient, 0.05% NH$_4$OH added) to afford the product as a solid. LC-MS (+ESI) m/z=384.4 and 386.3 (M+2+H)$^+$.

Example 19

1-Methyl-6-(trifluoromethyl)-N-(1-(4-(trifluoromethyl)phenyl)cyclopropyl)-1H-pyrazolo[3,4-d]pyrimidin-4-amine

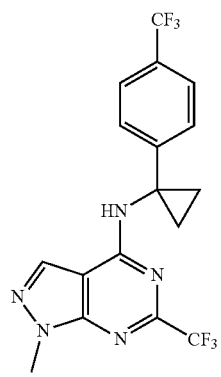

Step 1: 1-Methyl-6-(trifluoromethyl)-1H-pyrazolo[3,4-d]pyrimidin-4(5H)-one

To a solution of 5-amino-1-methyl-1H-pyrazole-4-carboxamide (0.200 g, 1.4 mmol) in ethanol (10 mL) were added ethyl 2,2,2-trifluoroacetate (0.123 g, 8.6 mmol) and sodium hydride (60% suspension in mineral oil, 0.571 g, 14.8 mmol) with stirring at 25° C. The reaction solution was degassed with nitrogen for 3 times and stirred at 90° C. for 16 h. The resulting mixture was cooled to room temperature and concentrated under reduced pressure. The residue was partitioned between aqueous hydrochloride acid (1N, 10 mL) and ethyl acetate (20 mL). The separated aqueous layer was extracted with ethyl acetate (2×15 mL). The combined organic layers were washed with brine (20 mL) and dried over anhydrous sodium sulfate. The solids were filtered out and the filtrate was concentrated under vacuum. The title compound was obtained as a solid and used in next step directly without further purification. MS (+ESI) m/z=219.0.

Step 2: 4-Chloro-1-methyl-6-(trifluoromethyl)-1H-pyrazolo[3,4-d]pyrimidine

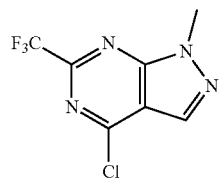

To 1-methyl-6-(trifluoromethyl)-1H-pyrazolo[3,4-d]pyrimidin-4(5H)-one (0.130 g, 0.6 mmol) was added phosphorus oxychloride (1 mL). The reaction mixture was stirred at 105° C. for 2 d and cooled to room temperature and concentrated under reduced pressure. The residue was quenched by ice water (50 mL). The aqueous layer was extracted with ethyl acetate (3×50 mL). The combined organic layers was washed with sat. NaHCO$_3$ (50 mL), brine (50 mL) and dried over anhydrous sodium sulfate. The solids were filtered out. The filtrate was concentrated under reduced pressure. The residue was purified by column chromatography over silica gel using ethyl acetate as eluent to provide the title compound as a solid. MS (+ESI) m/z=237.1; 239.1.

Step 3: 1-Methyl-6-(trifluoromethyl)-N-(1-(4-(trifluoromethyl)phenyl)cyclopropyl)-1H-pyrazolo[3,4-d]pyrimidin-4-amine

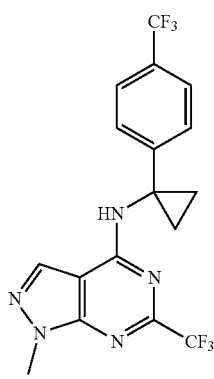 [SMILES: Cn1ncc2c(NC3(c4ccc(C(F)(F)F)cc4)CC3)nc(C(F)(F)F)nc21]

To a solution of 4-chloro-1-methyl-6-(trifluoromethyl)-1H-pyrazolo[3,4-d]pyrimidine (0.100 g, 0.4 mmol) in N-methyl-2-pyrrolidinone was added N,N-diisopropylethylamine (148 μL, 0.8 mmol) and 1-(4-(trifluoromethyl)phenyl)cyclopropanamine (85.0 mg, 0.4 mmol) at room temperature. The resulting solution was stirred at 120° C. for 16 h and then cooled to room temperature. The resulting mixture was diluted with water (50 mL) and extracted with ethyl acetate (3×50 mL). The combined organic layers were washed with water (50 mL), brine (50 mL) and dried over anhydrous sodium sulfate. The solids were filtered out. The filtrate was concentrated under reduced pressure. The residue was purified by Prep-HPLC with the following conditions: Column: X Bridge Phenyl 19×150 mm, 5 um; Mobile Phase A: Water (0.05% NH$_4$HCO$_3$), Mobile Phase B: Acetonitrile; Flow rate: 20 mL/min; Gradient: 35% B to 50% B in 7 min; 254 nm. The fractions containing desired product were combined and concentrated to afford the title compound as a solid. MS (+ESI) m/z=402.2. $^1$H NMR (300 MHz, CD$_3$OD) δ: 8.10 (s, 1H), 7.67-7.40 (m, 2H), 7.40-7.37 (m, 2H), 3.98 (s, 3H), 1.78-1.62 (m, 4H).

Example 20

1,6-Dimethyl-N-{1-[4-(trifluoromethyl)phenyl]cyclopropyl}-1H-pyrazolo[3,4-d]pyrimidin-4-amine

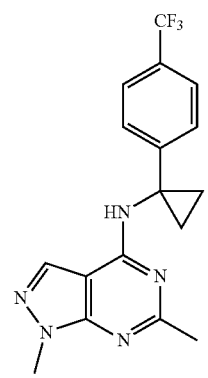 [SMILES: Cc1nc(NC2(c3ccc(C(F)(F)F)cc3)CC2)c2cnn(C)c2n1]

4-Chloro-1,6-dimethyl-1H-pyrazolo[3,4-d]pyrimidine (from Preparatory Example 1, 20 mg, 0.11 mmol), 1-[4-(trifluoromethyl) phenyl]cyclopropanamine hydrochloride (31 mg, 0.13 mmol) and DIEA (0.15 mL, 0.86 mmol) were charged into a 2-5 mL microwave tube and 1 mL of NMP was added. The vial was crimp sealed, placed in an oil bath, and stirred for 18 h at 100° C. The vessel was removed from the oil bath and allowed to cool down to room temperature. The reaction was checked by LCMS which proved that the reaction was complete. The mixture was diluted with 2 mL of water and 2.5 mL of CH$_3$CN, filtered, and the filtrate was purified by Gilson RP-HPLC using gradient solvent 10-75% CH$_3$CN in water (both contain 0.05% TFA), Sunfire prep C18 OBD 19×100 mm column and 12 min method (3 injections) to afford the title compound as a solid. LCMS (+ESI) m/z=348.1. $^1$H NMR (300 MHz, CD$_3$OD) δ: 8.22 (s, 1H), 7.65-7.60 (m, 2H), 7.48-7.37 (m, 2H), 3.92 (s, 3H), 2.65 (s, 3H), 1.72-1.63 (m, 4H).

The following compounds in Table 4 were prepared using procedures similar to those described in Example 20 using appropriate starting materials.

TABLE 4

| Example No. | Structure | IUPAC Name | Observed Exact Mass [M + H]$^+$ |
|---|---|---|---|
| 21 | 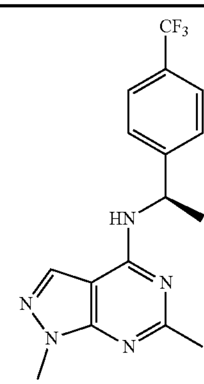 | 1,6-Dimethyl-N-{(1R)-1-[4-(trifluoromethyl)-phenyl]ethyl}-1H-pyrazolo[3,4-d]-pyrimidin-4-amine | 336.2 |

TABLE 4-continued

| Example No. | Structure | IUPAC Name | Observed Exact Mass [M + H]+ |
|---|---|---|---|
| 22 | 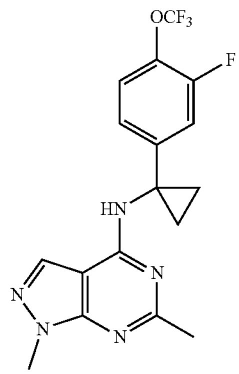 [SMILES: Cc1nc(NC2(c3ccc(OC(F)(F)F)c(F)c3)CC2)c2cnn(C)c2n1] | N-{1-[3-Fluoro-4-(trifluoromethyl)-phenyl]cyclo-propyl}-1,6-dimethyl-1H-pyrazolo[3,4-d]-pyrimidin-4-amine | 382.3 |
| 23 | 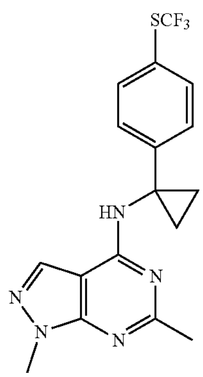 | 1,6-Dimethyl-N-(1-{4-[(trifluoromethyl)-sulfanyl]phenyl}-cyclopropyl)-1H-pyrazolo[3,4-d]-pyrimidin-4-amine | 380.1 |
| 24 | 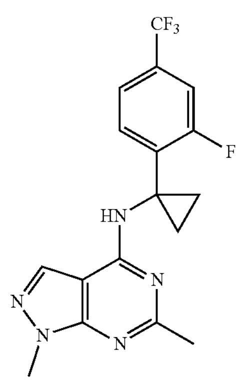 [SMILES: Cc1nc(NC2(c3ccc(C(F)(F)F)cc3F)CC2)c2cnn(C)c2n1] | N-{1-[2-Fluoro-4-(trifluoromethyl)-phenyl]cyclo-propyl}-1,6-dimethyl-1H-pyrazolo[3,4-d]-pyrimidin-4-amine | 366.1 |
| 25 | 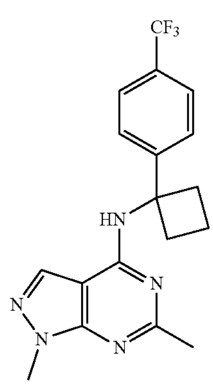 [SMILES: Cc1nc(NC2(c3ccc(C(F)(F)F)cc3)CCC2)c2cnn(C)c2n1] | 1,6-Dimethyl-N-{1-[4-(trifluoro-methyl)phenyl]-cyclobutyl}-1H-pyrazolo[3,4-d]-pyrimidin-4-amine | 362.0 |

Example 26

N,1,6-Trimethyl-N-{1-[4-(trifluoromethyl)phenyl]cyclopropyl}-1H-pyrazolo[3,4-d]pyrimidin-4-amine

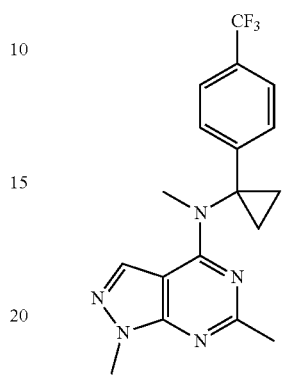

The title compound was prepared using similar procedures as in Example 17 using 1,6-dimethyl-N-{1-[4-(trifluoromethyl)phenyl]cyclopropyl}-1H-pyrazolo[3,4-d]pyrimidin-4-amine (Example 21) as the appropriate starting material. MS (+ESI) m/z=362.1.

Example 27

N,1,6-Trimethyl-N-(1-{4-[(trifluoromethyl)sulfanyl]phenyl}cyclopropyl)-1H-pyrazolo[3,4-d]pyrimidin-4-amine

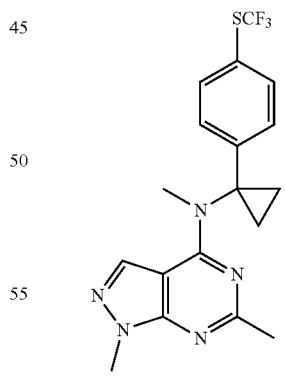

The title compound was prepared using similar procedures as in Example 17 using 1,6-dimethyl-N-(1-{4-[(trifluoromethyl)sulfanyl]phenyl}cyclopropyl)-1H-pyrazolo[3,4-d]pyrimidin-4-amine (Example 24) as the appropriate starting material. MS (+ESI) m/z=380.2.

Example 28

N-{1-[3-Fluoro-4-(trifluoromethyl)phenyl]cyclopropyl}-6-methyl-1-(2,2,2-trifluoroethyl)-1H-pyrazolo[3,4-d]pyrimidin-4-amine

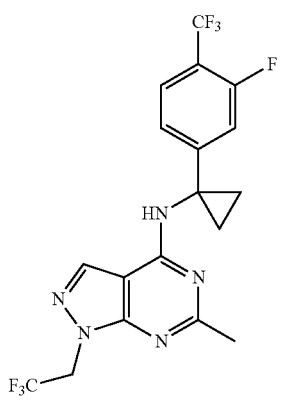 [SMILES: Cc1nc(NC2(c3ccc(C(F)(F)F)c(F)c3)CC2)c2cnn(CC(F)(F)F)c2n1]

Step 1: 6-Methyl-1-(2,2,2-trifluoroethyl)-1,5-dihydro-4H-pyrazolo[3,4-d]pyrimidin-4-one

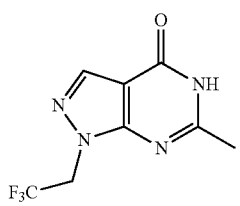 [SMILES: Cc1nc2c(cnn2CC(F)(F)F)c(=O)[nH]1]

The suspension of commercially available 5-amino-1-(2,2,2-trifluoroethyl)-1H-pyrazole-4-carbozamide (400 mg, 1.922 mmol) in 5 mL of anhydrous 1,4-dioxane was cooled to 0° C., then sodium carbonate solid (407 mg, 3.84 mmol) was added followed by dropwise addition of acetyl chloride, (0.15 mL, 2.02 mmol) over 1 min and this resulting mixture was stirred 20 min at 0° C. and then 30 min at rt. The reaction was then heated to 70° C. and stirred at that temperature under nitrogen overnight. LCMS show some of the product as a minor peak, so more acetyl chloride (0.05 mL, 0.67 mmol) was added and the mixture heated to 100° C. and stirred at that temperature over the weekend. The mixture was then cooled to room temperature and the solvent removed under reduced pressure. The residue was taken up in 40% methanol in DCM (5 mL) and solid was filtered off. The filtrate was concentrated to dryness and then taken up again in 40% methanol in DCM (2 mL) and placed on preparative TLC plates (3×1000 μM, silica gel). The plates were developed with 7% methanol in DCM and the bands containing the product removed from the plate. The product was eluted off with 10% methanol in DCM (~150 mL) and the filtrate concentrated to dryness to afford the product as a solid. LCMS (+ESI) m/z=233.0.

Step 2: 4-Chloro-6-methyl-1-(2,2,2-trifluoroethyl)-1H-pyrazolo[3,4-d]pyrimidine

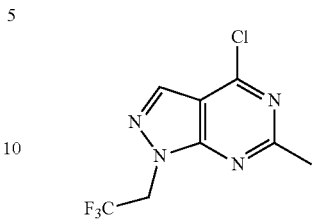

To the reaction flask charged with 6-methyl-1-(2,2,2-trifluoroethyl)-1,5-dihydro-4H-pyrazolo[3,4-d]pyrimidin-4-one (90 mg, 0.388 mmol) was added 1.5 mL of $POCl_3$ and 0.5 mL of DMF. The mixture was then heated to 95° C., and the heterogeneous mixture turned a translucent brown homogenous solution during heating. This mixture was stirred at 95° C. for 2 h; The mixture was cooled down and quenched with 50 mL of ice water, then extracted with EtOAc (2×50 mL). The organics were combined and dried on $Na_2SO_4$, filtered and filtrate was concentrated in vacuo to give the crude desired product which was used without further purification for next step. LCMS (+ESI) m/z=251.0 and 253.0 $(M+2+H)^+$.

Step 3: N-{1-[3-Fluoro-4-(trifluoromethyl)phenyl]cyclopropyl}-6-methyl-1-(2,2,2-trifluoroethyl)-1H-pyrazolo[3,4-d]pyrimidin-4-amine

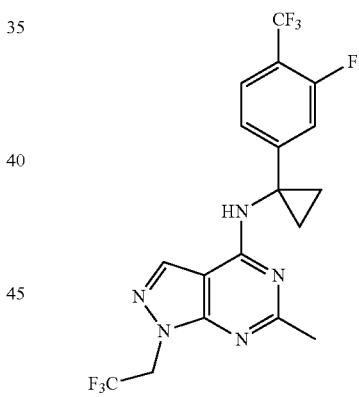

To a solution of 4-chloro-6-methyl-1-(2,2,2-trifluoroethyl)-1H-pyrazolo[3,4-d]pyrimidine (20 mg, 0.82 mmol) and 1-[3-fluoro-4-(trifluoromethyl)phenyl]cyclopropanamine hydrochloride (25 mg, 0.098 mmol) in anhydrous NMP (0.3 mL) in a 2-5 mL microwave vial was added dropwise via syringe DIEA (0.1 mL, 0.573 mmol) and the resulting solution heated via oil bath to 120° C. overnight. The reaction was allowed to cool and was quenched with 1 mL of sat. aq. sodium bicarbonate solution. The solution was diluted with 5 mL ethyl acetate. The organic layer was separated, the aqueous was re-extracted with 2.5 mL of ethyl acetate and the organics then combined. The organics were washed with 1 mL water, dried over sodium sulfate, filtered and the filtrate concentrated to dryness. The residue was taken up into 1.5 mL of acetonitrile/water (4:1) and purified by reverse phase HPLC using a gradient of 10-90% acetonitrile in water with 0.05% TFA as buffer to afford the product as a solid. MS (+ESI) m/z=434.0. ¹H NMR (500 MHz, CD₃OD) δ: 8.28 (s, 1H), 7.78 (s, 1H), 7.66-7.56 (m, 1H), 7.28-7.14 (m, 2H), 5.18-5.02 (m, 2H), 2.66 (s, 3H), 1.72 (br s, 2H), 1.65-1.58 (m, 2H).

Example 29

1-Methyl-4-{1-[4-(trifluoromethyl)phenyl]cyclopropylamino}-1H-pyrazolo[3,4-d]pyrimidine-6-carbonitrile

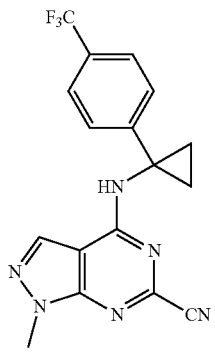 [SMILES: Cn1ncc2c(NC3(c4ccc(C(F)(F)F)cc4)CC3)nc(C#N)nc21]

Step 1: Methyl 2-((4-carbamoyl-1-methyl-1H-pyrazol-5-yl)amino)-2-oxoacetate

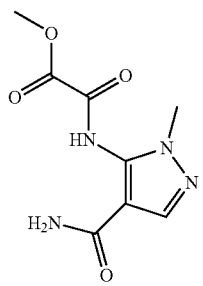 [SMILES: COC(=O)C(=O)Nc1c(C(N)=O)cnn1C]

To a solution of 5-amino-1-methyl-1H-pyrazole-4-carboxamide (0.400 g, 2.9 mmol) in pyridine (3 mL) was added methyl 2-chloro-2-oxoacetate (0.350 g, 2.9 mmol). The reaction solution was stirred at 25° C. for 16 h. The resulting mixture was concentrated under reduced pressure. The residue was diluted with water (50 mL) and extracted with ethyl acetate (3×50 mL). The combined organic layers was washed with water (50 mL), brine (50 mL) and dried over anhydrous sodium sulfate. The solids were filtered out. The filtrate was concentrated under reduced pressure. The residue was purified by column chromatography over silica gel eluting with isocratic 10% of methanol in dichloromethane to provide the title compound as a solid. ¹H NMR (300 MHz, DMSO-d₆) δ: 10.81 (s, 1H), 7.86 (s, 1H), 7.39 (brs, 1H), 7.07 (brs, 1H), 3.86 (s, 3H), 6.63 (s, 3H).

Step 2: Methyl 1-methyl-4-oxo-4,5-dihydro-1H-pyrazolo[3,4-d]pyrimidine-6-carboxylate

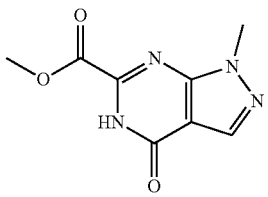

To a solution of methyl 2-((4-carbamoyl-1-methyl-1H-pyrazol-5-yl)amino)-2-oxoacetate (0.240 g, 1.061 mmol) in xylene (6 mL) was added hexamethyldisilazane (0.4 mL, 2.1 mmol). The reaction solution was stirred at 140° C. for 16 h. The resulting solution was cooled to room temperature and concentrated under reduced pressure. The residue was purified by column chromatography over silica gel, eluting with isocratic 10% of methanol in dichloromethane as eluent. The fractions containing desired product were combined and concentrated. The title compound was obtained as a solid. MS (+ESI) m/z=209.0

Step 3: 1-Methyl-4-oxo-4,5-dihydro-1H-pyrazolo[3,4-d]pyrimidine-6-carboxamide

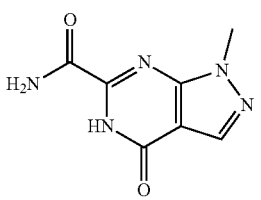

To methyl 1-methyl-4-oxo-4,5-dihydro-1H-pyrazolo[3,4-d]pyrimidine-6-carboxylate (0.145 g, 0.7 mmol) was added sat. ammonia in MeOH (5 mL, 37.0 mmol) at room temperature. The resulting solution was stirred at 80° C. for 16 h. The resulting solution was cooled to room temperature. The resulting solution was concentrated under reduced pressure. The title compound was obtained as a solid and used in the next step directly without further purification. MS (+ESI) m/z=194.0.

Step 4: 4-Chloro-1-methyl-1H-pyrazolo[3,4-d]pyrimidine-6-carbonitrile

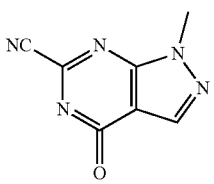

To a solution of 1-methyl-4-oxo-4,5-dihydro-1H-pyrazolo[3,4-d]pyrimidine-6-carboxamide (0.130 g, 0.7 mmol) in POCl₃ (2 mL) was added PCl₅ (0.140 g, 0.7 mmol) at room temperature. The resulting solution was stirred at 100° C. for 16 h, then was cooled to room temperature and concentrated under reduced pressure. The residue was quenched by ice water (50 mL), extracted with ethyl acetate (3×50 mL). The combined organic layers was washed with sat. NaHCO₃ (50 mL), brine (50 mL) and dried over anhydrous sodium sulfate. The solids were filtered out. The filtrate was concentrated under reduced pressure. The residue was purified by column chromatography over silica gel, eluting with isocratic 50% of ethyl acetate in petroleum ether to provide the title compound as a solid. ¹H NMR (300 MHz, CD₃OD) δ: 8.44 (s, 1H), 4.17 (s, 3H).

Step 5: 1-Methyl-4-((1-(4-(trifluoromethyl)phenyl)cyclopropyl)amino)-1H-pyrazolo[3,4-d]pyrimidine-6-carbonitrile

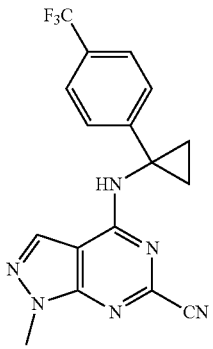

To a solution of 4-chloro-1-methyl-1H-pyrazolo[3,4-d]pyrimidine-6-carbonitrile (40.0 mg, 0.2 mmol) in NMP (1 mL) was added N,N-diisopropylethylamine (0.036 mL, 0.2 mmol) and 1-(4-(trifluoromethyl)phenyl)cyclopropanamine (41.6 mg, 0.2 mmol) at room temperature. The resulting solution was stirred at 120° C. for 16 h. The resulting solution was cooled to room temperature and diluted with water (30 mL) and extracted with ethyl acetate (3×30 mL). The combined organic layers was washed with water (30 mL), brine (30 mL) and dried over anhydrous sodium sulfate. The solids were filtered out. The filtrate was concentrated under reduced pressure. The residue was purified by Pre-HPLC with the following conditions: Column: X Bridge Phenyl 19×150 mm, 5 um; Mobile Phase A: Water (0.05% NH$_4$HCO$_3$), Mobile Phase B: Acetonitrile; Flow rate: 20 mL/min; Gradient: 25% B to 45% B in 30 min; 254 nm. The fractions containing desired product were combined and concentrated to afford the title compound as a solid. MS (+ESI) m/z=359.1. $^1$H NMR (300 MHz, CD$_3$OD) δ: 8.16 (s, 1H), 7.65-7.50 (m, 2H), 7.50-7.31 (m, 2H), 3.93 (s, 3H), 1.41-1.82 (m, 4H).

Example 30

1,6-Dimethyl-4-({1-[4-(trifluoromethyl)phenyl]cyclopropyl}oxy)-1H-pyrazolo[3,4-d]pyrimidine

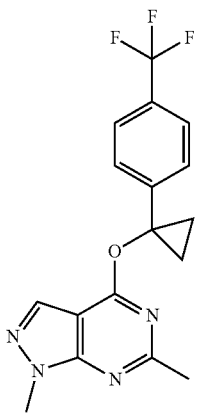 [SMILES: Cc1nc(OC2(c3ccc(C(F)(F)F)cc3)CC2)c2cnn(C)c2n1]

To a solution of 4-chloro-1,6-dimethyl-1H-pyrazolo[3,4-d]pyrimidine (35 mg, 0.192 mmol) in DMSO (1 mL) was added N,N-diisopropylethylamine (100 µl, 0.575 mmol) and 1-(4-(trifluoromethyl)phenyl)cyclopropanol (77.0 mg, 0.383 mmol) at room temperature. The resulting solution was stirred at 120° C. for 16 h and then cooled to room temperature. The resulting mixture was diluted with water (5 mL) and extracted with ethyl acetate (3×5 mL). The combined organic layers were washed with water (10 mL), brine (10 mL) and dried over anhydrous sodium sulfate. The solids were filtered out. The filtrate was concentrated under reduced pressure. The residue was purified by Prep-HPLC with the following conditions: Gilson RP-HPLC using 10-100% CH$_3$CN in water, both contain 0.05% TFA, Sunfire prep C18 OBD 19×100 mm column, 12 min method, rt=8.39 min) to afford the title compound as a solid. MS (+ESI) m/z=348.9. $^1$H NMR (500 MHz, CD$_3$OD) δ: 8.00 (s, 1H), 7.62 (d, J=8.0 Hz, 2H), 7.48 (d, J=8.0 Hz, 2H), 3.99 (s, 3H), 2.55 (s, 3H), 1.68-1.60 (m, 2H), 1.57-1.52 (m, 2H).

Example 31

N-(1-(3-Fluoro-4-(trifluoromethyl)phenyl)cyclopropyl)-7-methylimidazo[1,2-a]pyrimidin-5-amine

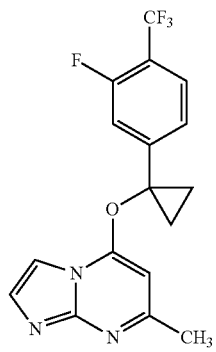 [SMILES: Cc1cc(OC2(c3ccc(C(F)(F)F)c(F)c3)CC2)n2ccnc2n1]

To a solution of commercially available 1-(3-fluoro-4-(trifluoromethyl)phenyl)cyclopropanamine hydrochloride (30.0 mg, 0.117 mmol) in ethanol (1 mL) was added 5-chloro-7-methylimidazo[1,2-a]pyrimidine (19.7 mg, 0.117 mmol). This was followed by the addition of DIEA (76.0 mg, 0.587 mmol). The reaction mixture was stirred at 80° C. for 48 h. The resulting mixture was cooled to room temperature and the solvent was removed under reduced pressure. The residue was purified by Prep-HPLC with the following conditions: Column: X Bridge C$^{18}$, 19×150 mm, 5 um; Mobile Phase A: Water/0.05% NH$_4$HCO$_3$, Mobile Phase B: Acetonitrile; Flow rate: 20 mL/min; Gradient: 30% B to 70% B in 10 min; 254 nm. The fractions containing desired product were combined and concentrated to afford the title compound as a solid. MS (+ESI) m/z=351.1. $^1$H NMR (400 MHz, MeOH-d$_4$) δ: 7.80 (d, J=1.6 Hz, 1H), 7.66-7.62 (m, 1H), 7.56 (d, J=1.6 Hz, 1H), 7.23-7.17 (m, 2H), 6.00 (s, 1H), 2.42 (s, 3H), 1.74-1.56 (m, 4H).

Example 32

(R)—N-(1-(3-Fluoro-4-(trifluoromethyl)phenyl)-2,2-dimethylpropyl)-7-methylimidazo[1,2-a]pyrimidin-5-amine

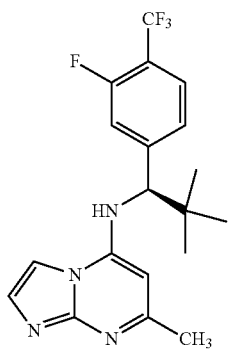 [SMILES: Cc1cc(N[C@@H](c2ccc(C(F)(F)F)c(F)c2)C(C)(C)C)n2ccnc2n1]

The title compound was prepared using similar procedures as in Example 31 using (R)-1-[3-fluoro-4-(trifluoromethyl)phenyl]-2,2-dimethylpropan-1-amine hydrochloride as the appropriate starting material. MS (+ESI) m/z=381.1. $^1$H NMR (400 MHz, MeOH-$d_4$) δ: 8.14 (d, J=1.2 Hz, 1H), 7.73-7.69 (m, 1H), 7.59-7.52 (m, 3H), 6.03 (s, 1H), 4.74 (s, 1H), 2.41 (s, 3H), 1.13 (s, 9H).

Examples 33 and 34

(R or S)-1-[3-Fluoro-4-(trifluoromethyl)phenyl]-2-methyl-1-{[7-(trifluoromethyl)imidazo[1,2-c]pyrimidin-5-yl]amino}propan-2-ol and (S or R)-1-[3-Fluoro-4-(trifluoromethyl)phenyl]-2-methyl-1-{[7-(trifluoromethyl)imidazo[1,2-c]pyrimidin-5-yl]amino}propan-2-ol

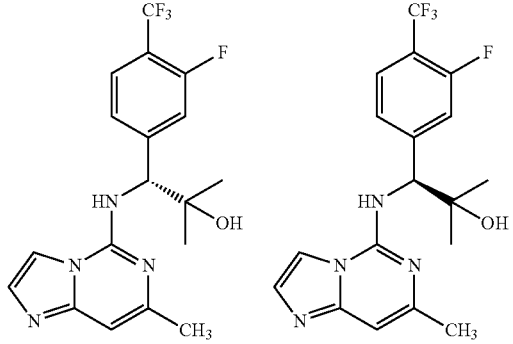 [SMILES: Cc1cc2nccn2c(N[C@H](c2ccc(C(F)(F)F)c(F)c2)C(C)(C)O)n1 ; Cc1cc2nccn2c(N[C@@H](c2ccc(C(F)(F)F)c(F)c2)C(C)(C)O)n1]

Step 1: 1-(3-Fluoro-4-(trifluoromethyl)phenyl)-2-methyl-1-((7-(trifluoromethyl)imidazo[1,2-c]pyrimidin-5-yl)amino)propan-2-ol

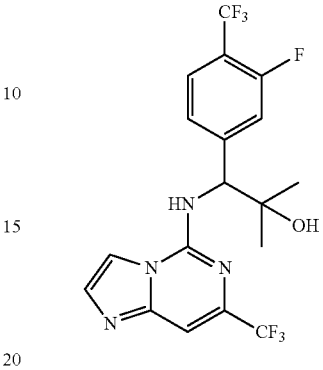

To a solution of 1-amino-1-(3-fluoro-4-(trifluoromethyl)phenyl)-2-methylpropan-2-ol (0.102 g, 0.406 mmol) in iPrOH (3 mL) was added 5-chloro-7-(trifluoromethyl)imidazo[1,2-c]pyrimidine (from Preparatory Example 4, 90.0 mg, 0.406 mmol). This was followed by the addition of DIEA (0.14 mL, 0.812 mmol). The reaction mixture was stirred at 80° C. for 3 h. The resulting mixture was cooled to room temperature and concentrated under reduced pressure. The residue was purified by Prep-HPLC with the following conditions: Column: X Select CSH Prep C$^{18}$, 19×150 mm, 5 um; Mobile Phase A: Water/0.05% NH$_4$HCO$_3$, Mobile Phase B: Acetonitrile; Flow rate: 20 mL/min; Gradient: 49% B to 62% B in 8 min; 254 nm. The fractions containing desired product were combined and concentrated to afford the title compound as a solid. MS (+ESI) m/z=437.2.

Step 5: (R or S)-1-(3-Fluoro-4-(trifluoromethyl)phenyl)-2-methyl-1-((7-(trifluoromethyl) imidazo[1,2-c]pyrimidin-5-yl)amino)propan-2-ol and (S or R)-1-(3-Fluoro-4-(trifluoromethyl)phenyl)-2-methyl-1-((7-(trifluoromethyl) imidazo[1,2-c]pyrimidin-5-yl)amino)propan-2-ol

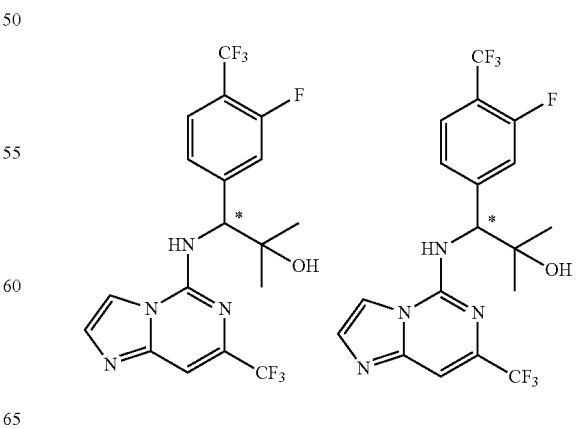

1-(3-Fluoro-4-(trifluoromethyl)phenyl)-2-methyl-1-((7-(trifluoromethyl)imidazo[1,2-c]pyrimidin-5-yl)amino)propan-2-ol (80.0 mg, 0.183 mmol) was purified by Chiral prep-HPLC following the conditions: Column: CHIRAL-CEL OJ-H 2×25 cm, 20 um; Mobile Phase A: Hex-HPLC, Mobile Phase B: EtOH-HPLC; Flow rate: 20 mL/min; Gradient: isocratic 5% B in 20 min; 254/220 nm; The faster-eluting enantiomer of the title compound (Example 33) was obtained at 8.44 min as a solid. MS (+ESI) m/z=436.9. $^1$H NMR (400 MHz, DMSO-$d_6$) δ: 8.60 (s, 1H), 8.01 (d, J=8.4 Hz, 1H), 7.74-7.70 (m, 3H), 7.54 (d, J=8.4 Hz, 1H), 7.37 (s, 1H), 5.27 (d, J=8.4 Hz, 1H), 5.06 (s, 1H), 1.30 (s, 3H), 1.12 (s, 3H). The slower-eluting enantiomer of the title compound (Example 34) was obtained at 15.59 min as a solid. MS (+ESI) m/z=437.2. $^1$H NMR (400 MHz, DMSO-$d_6$) δ: 8.60 (s, 1H), 8.01 (d, J=8.4 Hz, 1H), 7.74-7.70 (m, 3H), 7.54 (d, J=8.4 Hz, 1H), 7.37 (s, 1H), 5.27 (d, J=8.4 Hz, 1H), 5.06 (s, 1H), 1.30 (s, 3H), 1.12 (s, 3H).

Example 35

N-{(1R)-1-[3-Fluoro-4-(trifluoromethyl)phenyl]-2,2-dimethylpropyl}-2,9-dimethyl-9H-purin-6-amine

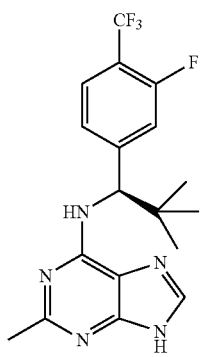 [SMILES: Cc1nc(N[C@@H](c2ccc(C(F)(F)F)c(F)c2)C(C)(C)C)c2nc[nH]c2n1]

To a microwave tube charged with a stir bar was added 6-chloro-2-methyl-9H-purine (0.15 g, 0.89 mmol) [CAS #100859-35-6] followed by (R)-1-(3-fluoro-4-(trifluoromethyl)phenyl)-2,2-dimethylpropan-1-amine hydrochloride (0.38 g, 1.34 mmol). NMP (3 mL) was added followed by dropwise addition of DIEA (0.47 mL, 2.7 mmol). The tube was purged to $N_2$, capped, and was heated to 120° C. The mixture was stirred at 120° C. for 24 h, cooled to RT, and the mixture was diluted with EtOAc (50 mL). The organic layer was washed with water (2×) and brine (1×). The organic layer was dried over $Na_2SO_4$, filtered, and concentrated under reduced pressure. The residue was purified by reverse phase HPLC chromatography (SureFire C18, 20-90% ACN in water (0.05% TFA)) to afford the title compound as a solid. $^1$H NMR (CDCl$_3$, 500 MHz) δ: 8.74 (br s, 1H), 8.37 (br s, 1H), 7.59 (s, 1H), 7.36 (m, 2H), 5.45 (d, J=9.0 Hz, 1H), 2.73 (s, 3H), 1.18 (s, 9H). LC/MS (m/z): 382.1 (M+H)$^+$.

Example 36

N-{1-[3-Fluoro-4-(trifluoromethyl)phenyl]cyclopropyl}-2-methyl-9H-purin-6-amine

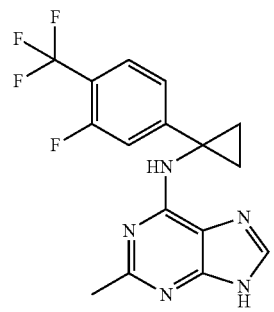 [SMILES: Cc1nc(NC2(c3ccc(C(F)(F)F)c(F)c3)CC2)c2nc[nH]c2n1]

The title compound was prepared using similar procedures as in Example 35 using 1-(3-fluoro-4-(trifluoromethyl)phenyl)cyclopropan-1-amine hydrochloride and other appropriate starting materials. LC/MS (m/z): 352.1 (M+H)$^+$.

Example 37

N-(1-(3-Fluoro-4-(trifluoromethyl)phenyl)cyclopropyl)-2,9-dimethyl-9H-purin-6-amine

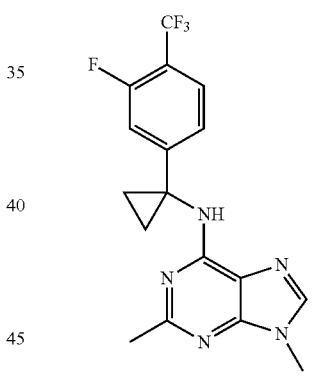

Step 1: 6-Chloro-2,9-dimethyl-9H-purine

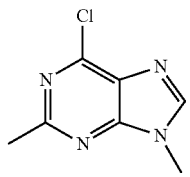

To a solution of 6-chloro-2-methyl-9H-purine (500 mg, 2.97 mmol) in DMF (12 mL) under $N_2$ at RT was added $K_2CO_3$ (1.64 g, 11.86 mmol) followed by dropwise addition of iodomethane (0.30 mL, 4.75 mmol). The mixture was stirred at RT for 12 h whereupon it was diluted with EtOAc (100 mL). The organic layer was washed with water (2×30 mL) and brine (30 mL). The organic layer was dried over Na₂SO₄, filtered, and concentrated under reduced pressure. The residue was purified by silica gel column chromatography (15-30% EtOAc in hexanes) to afford the title compound as a solid. LC/MS (m/z): 183.1 (M+H)⁺.

Step 2: N-(1-(3-Fluoro-4-(trifluoromethyl)phenyl) cyclopropyl)-2,9-dimethyl-9H-purin-6-amine

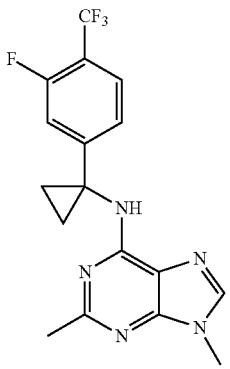 [SMILES: Cc1nc(NC2(c3ccc(C(F)(F)F)c(F)c3)CC2)c2ncn(C)c2n1]

To a solution of 6-chloro-2,9-dimethyl-9H-purine (94 mg, 0.515 mmol) in NMP (2 mL) under N₂ added 1-(3-fluoro-4-(trifluoromethyl)phenyl) cyclopropanamine hydrochloride (145 mg, 0.57 mmol) followed by dropwise addition of DIEA (0.270 mL, 1.544 mmol). The mixture was heated to 120° C., stirred for 12 h, and cooled to RT. The mixture was diluted with EtOAc (50 mL) and the organic layer was washed with water (2×) and brine. The organic layer dried over Na₂SO₄, filtered, and concentrated under reduced pressure. The residue was purified by reverse phase HPLC chromatography (SureFire C18, 10-90% ACN in water (0.05% TFA)) to afford the title compound as a solid. ¹H NMR (CDCl₃, 500 MHz) δ: 12 (br s, 1H), 7.80 (s, 1H), 7.49 (m, 1H), 7.20 (m, 2H), 3.81 (s, 3H), 2.75 (s, 3H), 1.60 (m, 4H). LC/MS (m/z): 366.3 (M+H)⁺.

Example 38

N-{(1R)-1-[3-fluoro-4-(trifluoromethyl)phenyl]-2,2-dimethylpropyl}-2,9-dimethyl-9H-purin-6-amine

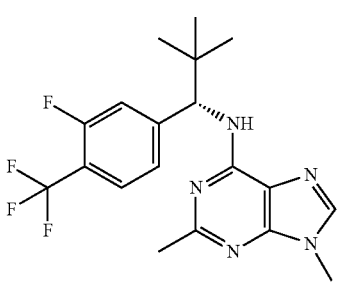 [SMILES: Cc1nc(N[C@H](c2ccc(C(F)(F)F)c(F)c2)C(C)(C)C)c2ncn(C)c2n1]

The title compound was prepared using similar procedures as in Example 37 using (R)-1-(3-fluoro-4-(trifluoromethyl)phenyl)-2,2-dimethylpropan-1-amine and other appropriate starting materials. LC/MS (m/z): 352.1 (M+H)⁺.

Example 39

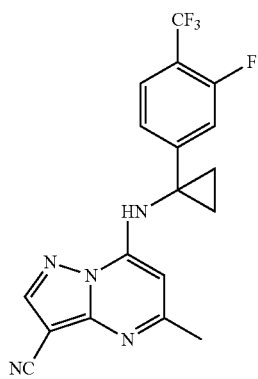 [SMILES: Cc1cc(NC2(c3ccc(C(F)(F)F)c(F)c3)CC2)n2ncc(C#N)c2n1]

Step 1: 7-Chloro-5-methylpyrazolo[1,5-a]pyrimidine-3-carbonitrile

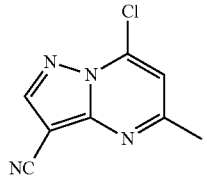

To a solution of 7-hydroxy-5-methylpyrazolo[1,5-a]pyrimidine-3-carbonitrile (1.0 g, 5.74 mmol) [CAS #89939-60-6] in POCl₃ (5 mL) added pyridine (0.23 mL, 2.87 mmol) under N₂. The mixture was stirred at 85° C. for 1 h and then at 120° C. for an additional hour. Chloroform (5 mL) was added to the mixture, which was then refluxed for 1 h. The mixture was cooled to RT and was poured onto ice. The mixture was extracted with CHCl₃ (3×60 mL) and the organic layers were combined. The organic layer was dried over Na₂SO₄, filtered, and concentrated under reduced pressure. The residue was purified by silica gel column chromatography (0-100% EtOAc in hexanes) to afford the title compound as a solid. LC/MS (m/z): 298.0 (M+H)⁺.

Step 2: 7-((1-(3-Fluoro-4-(trifluoromethyl)phenyl) cyclopropyl)amino)-5-methylpyrazolo[1,5-a]pyrimidine-3-carbonitrile

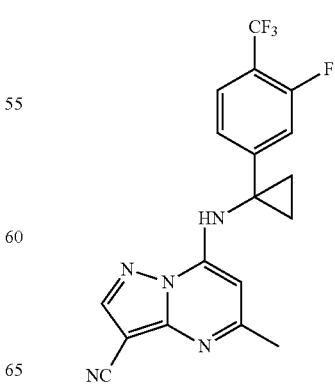

To a solution of 7-chloro-5-methylpyrazolo[1,5-a]pyrimidine-3-carbonitrile (100 mg, 0.52 mmol) in NMP (2 mL) added 1-(3-fluoro-4-(trifluoromethyl)phenyl)cyclopropanamine hydrochloride (146 mg, 0.57 mmol) and DIEA (0.27 mL, 1.56 mmol) under N₂. The mixture was stirred at 100° C. for 3 h and the mixture was cooled to RT. The mixture was diluted with EtOAc (50 mL) and was washed with sat. aq. NH₄Cl (2×) and brine (1×). The organic layer was dried over Na₂SO₄, filtered, and concentrated under reduced pressure. The residue was purified by silica gel column chromatography (0-100% EtOAc in hexanes) to afford the title compound as a solid. $^1$H NMR (CDCl₃, 500 MHz) δ: 8.27 (s, 1H), 7.60 (m, 1H), 7.01 (m, 2H), 6.05 (s, 1H), 2.59 (s, 3H), 1.61 (m, 4H). LC/MS (m/z): 376.1 (M+H)⁺.

Example 40

7-({(1R)-1-[3-Fluoro-4-(trifluoromethyl)phenyl]-2,2-dimethylpropyl}amino)-5-methylpyrazolo[1,5-a]pyrimidine-3-carbonitrile

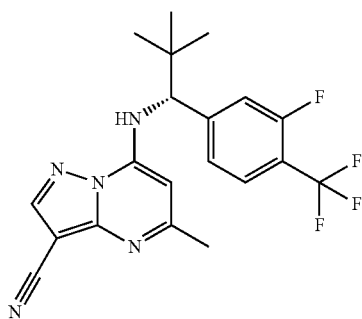 [SMILES: Cc1cc(N[C@@H](c2ccc(C(F)(F)F)c(F)c2)C(C)(C)C)n2ncc(C#N)c2n1]

The title compound was prepared using similar procedures as in Example 39 using (R)-1-(3-fluoro-4-(trifluoromethyl)phenyl)-2,2-dimethylpropan-1-amine and other appropriate starting materials. LC/MS (m/z): 406.1 (M+H)⁺.

Example 41

N⁷-{1-[3-Fluoro-4-(trifluoromethyl)phenyl]cyclopropyl}-5-methylpyrazolo[1,5-a]pyrimidine-3,7-diamine

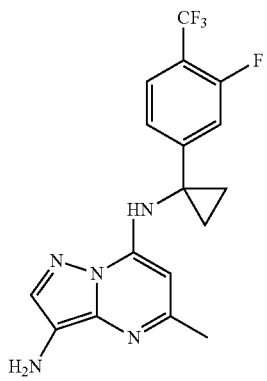

Step 1: 7-Chloro-5-methyl-3-nitropyrazolo[1,5-a]pyrimidine

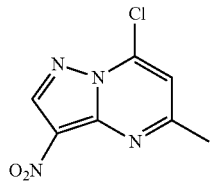

To a solution of 7-chloro-5-methylpyrazolo[1,5-a]pyrimidine (500 mg, 2.98 mmol) in conc. H₂SO₄ (4 mL) was added 70% nitric acid (1.90 mL, 29.8 mmol) dropwise at 0° C. The resulting mixture was stirred at 0° C. for 2 h and then at RT for 2 h. The mixture was poured to ice and stirred for 10 min whereupon the mixture was extracted with DCM (3×50 mL). The organic layers were combined, dried over Na₂SO₄, filtered, and concentrated under reduced pressure. The residue was purified by silica gel column chromatography (0-100% EtOAc in hexanes) to afford the title compound as a solid. $^1$H NMR (CDCl₃, 500 MHz) δ: 8.82 (s, 1H), 7.22 (s, 1H), 2.80 (s, 3H).

Step 2: N-(1-(3-Fluoro-4-(trifluoromethyl)phenyl)cyclopropyl)-5-methyl-3-nitropyrazolo[1,5-a]pyrimidin-7-amine

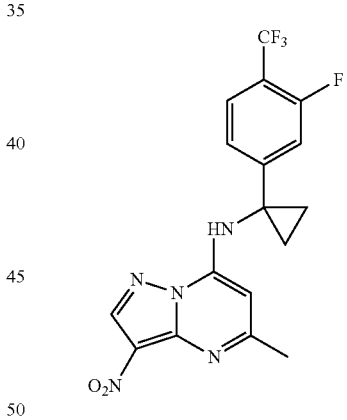

To a solution of 7-chloro-5-methyl-3-nitropyrazolo[1,5-a]pyrimidine (100 mg, 0.47 mmol) in NMP (2 mL) was added 1-(3-fluoro-4-(trifluoromethyl)phenyl)cyclopropanamine hydrochloride (132 mg, 0.52 mmol) and DIEA (0.25 mL, 1.41 mmol) under N₂. The mixture was stirred at 100° C. for 2 h and was cooled to RT. The mixture was diluted with EtOAc (50 mL) and was washed with sat. aq. NaHCO₃ (2×) and brine (1×). The organic layer was dried over Na₂SO₄, filtered, and concentrated under reduced pressure. The residue was purified by silica gel column chromatography (0-100% EtOAc in hexanes) to afford the title compound as a solid. LC/MS (m/z): 396.1 (M+H)⁺.

Step 3: N⁷-{1-[3-Fluoro-4-(trifluoromethyl)phenyl]cyclopropyl}-5-methylpyrazolo[1,5-a]pyrimidine-3,7-diamine

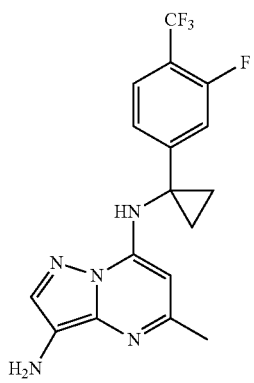 [SMILES: Cc1cc(NC2(c3ccc(C(F)(F)F)c(F)c3)CC2)n2ncc(N)c2n1]

To a solution of N-(1-(3-fluoro-4-(trifluoromethyl)phenyl)cyclopropyl)-5-methyl-3-nitropyrazolo[1,5-a]pyrimidin-7-amine (80 mg, 0.20 mmol) in ethanol (2 mL) added 10% Pd on C (22 mg, 0.020 mmol) under $N_2$. The mixture was then stirred under a $H_2$ balloon for 5 h whereupon the mixture was purged to $N_2$. The mixture was filtered through Celite and the resulting filtrate was concentrated under reduced pressure. The residue was purified by silica gel column chromatography (0-100% EtOAc:EtOH (3:1) in hexanes) to afford the title compound as a solid. ¹H NMR (CDCl₃, 500 MHz) δ: 7.81 (s, 1H), 7.59 (m, 1H), 7.01 (m, 2H), 6.83 (s, 1H), 3.21 (br s, 2H), 2.42 (s, 3H), 1.61 (m, 4H). LC/MS (m/z): 366.1 (M+H)⁺.

Example 42

N⁷-{(1R)-1-[3-Fluoro-4-(trifluoromethyl)phenyl]-2,2-dimethylpropyl}-5-methylpyrazolo[1,5-a]pyrimidine-3,7-diamine

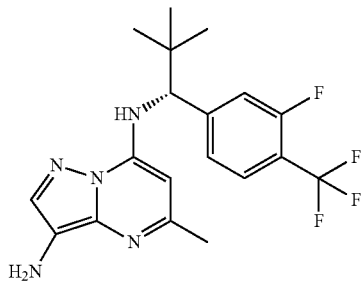 [SMILES: Cc1cc(N[C@@H](c2ccc(C(F)(F)F)c(F)c2)C(C)(C)C)n2ncc(N)c2n1]

The following example was prepared using similar procedures as in Example 41 using (R)-1-(3-fluoro-4-(trifluoromethyl)phenyl)-2,2-dimethylpropan-1-amine and other appropriate starting materials. LC/MS (m/z): 396.1 (M+H)⁺.

Example 43

[7-({1-[3-Fluoro-4-(trifluoromethyl)phenyl]cyclopropyl}amino)-5-methylpyrazolo[1,5-a]pyrimidin-2-yl]methanol

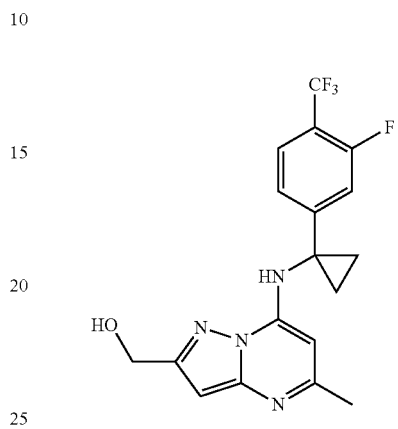

Step 1: Ethyl 7-((1-(3-fluoro-4-(trifluoromethyl)phenyl)cyclopropyl)amino)-5-methylpyrazolo[1,5-a]pyrimidine-2-carboxylate

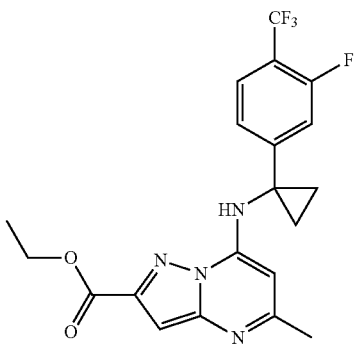 [SMILES: CCOC(=O)c1cc2nc(C)cc(NC3(c4ccc(C(F)(F)F)c(F)c4)CC3)n2n1]

To a solution of ethyl 7-chloro-5-methylpyrazolo[1,5-a]pyrimidine-2-carboxylate (Preparatory Example 2, 150 mg, 0.63 mmol) in NMP (2 mL) at RT under $N_2$ was added 1-(3-fluoro-4-(trifluoromethyl)phenyl) cyclopropanamine hydrochloride (176 mg, 0.69 mmol) followed by dropwise addition of DIEA (0.34 mL, 1.88 mmol). The mixture was heated to 100° C., stirred for 3 h, and was cooled to RT. The mixture was diluted with EtOAc (50 mL) and was washed with sat. aq. NH₄Cl (2×) and brine (1×). The organic layer was dried over Na₂SO₄, filtered, and concentrated under reduced pressure. The residue was purified by silica gel column chromatography (0-100% EtOAc in hexanes) to afford the title compound as a solid. LC/MS (m/z): 423.2 (M+H)⁺.

Step 2: [7-({1-[3-Fluoro-4-(trifluoromethyl)phenyl]cyclopropyl}amino)-5-methylpyrazolo[1,5-a]pyrimidin-2-yl]methanol

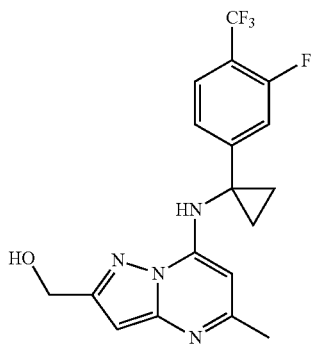 [SMILES: Cc1cc(NC2(c3ccc(C(F)(F)F)c(F)c3)CC2)n2nc(CO)cc2n1]

To a solution of ethyl 7-((1-(3-fluoro-4-(trifluoromethyl)phenyl)cyclopropyl)amino)-5-methylpyrazolo[1,5-a]pyrimidine-2-carboxylate (85 mg, 0.20 mmol) in DCM (2 mL) at RT under $N_2$ was added a solution of DibalH (1.0 M in $CH_2Cl_2$, 0.24 mL, 0.24 mmol) dropwise. The mixture was stirred at RT for 2 h whereupon a saturated solution of Rochelle's salt was added. The mixture was extracted with EtOAc (3×50 mL) and the organic layers were combined. The organic layer was dried over $Na_2SO_4$, filtered, and concentrated under reduced pressure. The residue was purified by silica gel column chromatography (0-100% EtOAc:EtOH (3:1) in hexanes) to afford the title compound as a solid. $^1$H NMR (CDCl$_3$, 500 MHz) δ: 7.59 (m, 1H), 7.01 (m, 2H), 6.41 (s, 1H), 5.81 (s, 1H), 4.98 (s, 2H), 2.42 (s, 3H), 1.62 (m, 4H). LC/MS (m/z): 381.1 (M+H)$^+$.

Example 44

[7-({(1R)-1-[3-Fluoro-4-(trifluoromethyl)phenyl]-2,2-dimethylpropyl}amino)-5-methylpyrazolo[1,5-a]pyrimidin-2-yl]methanol

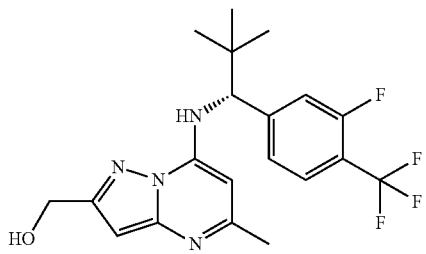 [SMILES: Cc1cc(N[C@@H](c2ccc(C(F)(F)F)c(F)c2)C(C)(C)C)n2nc(CO)cc2n1]

The following example was prepared using similar procedures as in Example 43 using (R)-1-(3-fluoro-4-(trifluoromethyl)phenyl)-2,2-dimethylpropan-1-amine and other appropriate starting materials. LC/MS (m/z): 381.1 (M+H)$^+$.

Example 45

[7-({1-[3-Fluoro-4-(trifluoromethyl)phenyl]cyclopropyl}amino)-5-methylpyrazolo[1,5-a]pyrimidin-3-yl]methanol

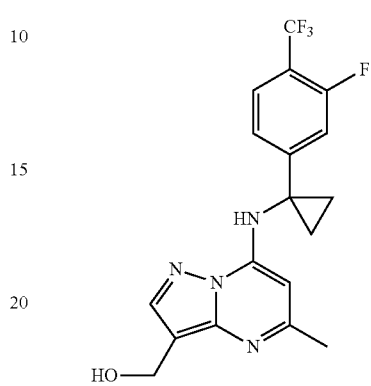

Step 1: Ethyl 7-((1-(3-fluoro-4-(trifluoromethyl)phenyl)cyclopropyl)amino)-5-methylpyrazolo[1,5-a]pyrimidine-3-carboxylate

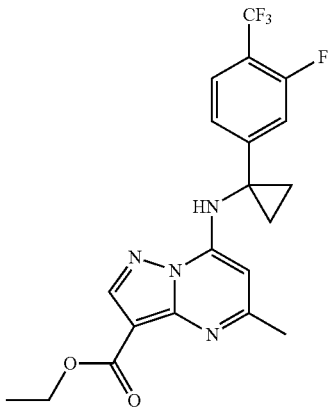 [SMILES: CCOC(=O)c1cnn2c(NC3(c4ccc(C(F)(F)F)c(F)c4)CC3)cc(C)nc12]

To a solution of ethyl 7-chloro-5-methylpyrazolo[1,5-a]pyrimidine-3-carboxylate (100 mg, 0.417 mmol) in NMP (2 mL) at RT under $N_2$ was added 1-(3-fluoro-4-(trifluoromethyl)phenyl) cyclopropanamine hydrochloride (117 mg, 0.459 mmol) followed by dropwise addition of DIEA (0.22 mL, 1.25 mmol). The mixture was heated to 100° C., stirred for 3 h, and was cooled to RT. The mixture was diluted with EtOAc (50 mL) and washed with sat. aq. NH$_4$Cl (2×30 mL) and brine (30 mL). The organic layer was dried over Na$_2$SO$_4$, filtered, and concentrated under reduced pressure. The residue was purified by silica gel column chromatography (0-100% EtOAc in hexanes) to afford the title compound as a solid. LC/MS (m/z): 423.1 (M+H)$^+$.

Step 2: [7-({1-[3-Fluoro-4-(trifluoromethyl)phenyl]cyclopropyl}amino)-5-methylpyrazolo[1,5-a]pyrimidin-3-yl]methanol

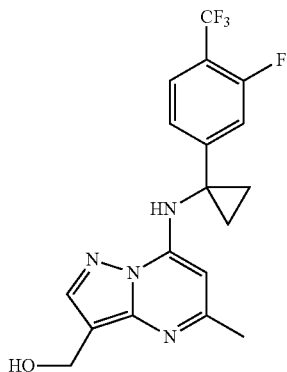 [SMILES: Cc1cc(NC2(c3ccc(C(F)(F)F)c(F)c3)CC2)n2ncc(CO)c2n1]

To a solution of ethyl 7-((1-(3-fluoro-4-(trifluoromethyl)phenyl)cyclopropyl)amino)-5-methylpyrazolo[1,5-a]pyrimidine-3-carboxylate (80 mg, 0.19 mmol) in DCM (2 mL) under $N_2$ at −78° C. was added a solution of DibalH (1M solution in $CH_2Cl_2$, 0.23 mL, 0.23 mmol). The mixture was stirred for 30 min, then was warmed to RT, followed by stirring for 30 min. An additional aliquot of the DibalH solution (1M solution in $CH_2Cl_2$, 0.29 mL, 0.29 mmol) was added, and the mixture was stirred at RT for another 30 min. The mixture was quenched with 1 M aqueous HCl and was concentrated under reduced pressure. The residue was purified by reverse phase HPLC chromatography (SureFire C18, 10-90% ACN in water (0.05% TFA)) to afford the title compound as a solid. $^1$H NMR (CDCl$_3$, 500 MHz) δ: 8.18 (s, 1H), 7.59 (m, 1H), 7.00 (m, 2H), 6.01 (s, 1H), 4.85 (s, 2H), 2.75 (s, 3H), 1.68 (m, 4H), LC/MS (m/z): 381.1 (M+H)$^+$.

Example 46

[7-({1-[3-Fluoro-4-(trifluoromethyl)phenyl]cyclopropyl}amino)-5-methylpyrazolo[1,5-a]pyrimidin-3-yl]methanol

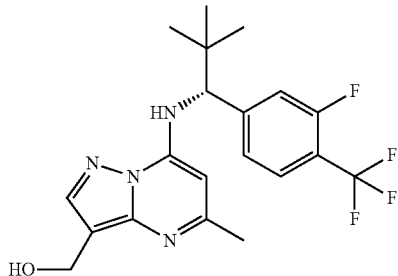 [SMILES: Cc1cc(N[C@@H](c2ccc(C(F)(F)F)c(F)c2)C(C)(C)C)n2ncc(CO)c2n1]

The title compound was prepared using similar procedures as in Example 45 using (R)-1-(3-fluoro-4-(trifluoromethyl)phenyl)-2,2-dimethylpropan-1-amine and other appropriate starting materials. LC/MS (m/z): 411.1 (M+H)$^+$.

Example 47

N-{1-[3-Fluoro-4-(trifluoromethyl)phenyl]cyclopropyl}-5-methylpyrazolo[1,5-a]pyrimidin-7-amine

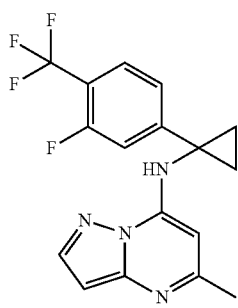 [SMILES: Cc1cc(NC2(c3ccc(C(F)(F)F)c(F)c3)CC2)n2nccc2n1]

To a mixture of 7-chloro-5-methyl-pyrazolo[1,5-a]pyrimidine (75 mg, 0.45 mmol) [CAS #16082-27-2] in NMP (2.2 mL) at RT was added 1-(3-fluoro-4-(trifluoromethyl)phenyl) cyclopropanamine hydrochloride (0.17 g, 0.67 mmol) followed by dropwise addition of DIEA (234 µL, 1.3 mmol). The mixture was affixed with a reflux condenser and was heated to 120° C. and stirred for 12 h. The mixture was cooled to RT and the excess NMP was removed by rotary evaporation with heat to afford a semisolid. The semisolid was partitioned between EtOAc (10 mL) and sat. aq. NaHCO$_3$ (3 mL) and the layers were separated. The aqueous layer was extracted with EtOAc (2×10 mL) and the organic layers were combined. The organic layer was washed with brine (2×5 mL), dried over Na$_2$SO$_4$, filtered, and concentrated under reduced pressure. The residue was purified by silica gel column chromatography (0-90% EtOAc in hexanes) to afford the title compound as a solid. $^1$H NMR (CDCl$_3$, 500 MHz) δ: 8.01 (d, J=2.3 Hz, 1H), 7.56 (t, J=7.8 Hz, 1H), 7.04-6.98 (m, 3H), 6.47 (d, J=2.3 Hz, 1H), 5.82 (s, 1H), 2.48 (s, 3H), 1.66-1.57 (m, 4H). LC/MS (m/z): 351.1 (M+H)$^+$.

Example 48

N-{(1R)-1-[3-Fluoro-4-(trifluoromethyl)phenyl]-2,2-dimethylpropyl}-5-methylpyrazolo[1,5-a]pyrimidin-7-amine

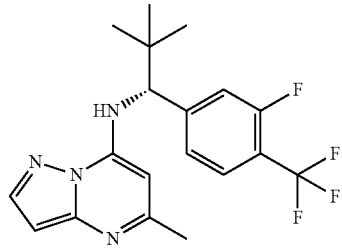 [SMILES: Cc1cc(N[C@@H](c2ccc(C(F)(F)F)c(F)c2)C(C)(C)C)n2nccc2n1]

The title compound was prepared using similar procedures as in Example 47 using (R)-1-(3-fluoro-4-(trifluoromethyl)phenyl)-2,2-dimethylpropan-1-amine and other appropriate starting materials. LC/MS (m/z): 381.1 (M+H)$^+$.

Assay

The activity of the compounds in accordance with the present invention as PDE2 inhibitors may be readily determined using a fluorescence polarization (FP) methodology (Huang, W., et al., J. Biomol Screen, 2002, 7: 215). In particular, the compounds of the following examples had activity in reference assays by exhibiting the ability to inhibit the hydrolysis of the phosphate ester bond of a cyclic nucleotide. Any compound exhibiting a Ki (inhibitory constant) of about 50 µM or below would be considered a PDE2 inhibitor as defined herein.

In a typical experiment the PDE2 inhibitory activity of the compounds of the present invention was determined in accordance with the following experimental method. Rhesus PDE2A3 was amplified from rhesus macaque brain cDNA (Biochain Institute, Hayward, Calif.) using primers based on human PDE2A sequence (accession NM_002599.3) where the forward primer containing a Kozak consensus was 5'-gccaccatgggggcaggcatgtggc-3' and the reverse primer was 5'-tcactcagcatcaaggctgca-3'. Amplification with Easy-A High-Fidelity PCR cloning enzyme (Stratagene, La Jolla, Calif.) was 95° C. for 2 minutes followed by thirty three cycles of 95° C. for 40 seconds, 52° C. for 30 seconds, and 72° C. for 2 minutes 48 seconds. Final extension was 72° C. for 7 minutes. The PCR product was TA cloned into pcDNA3.3-TOPO (Invitrogen, Carlsbad, Calif.) according to standard protocol. A consensus sequence was developed from multiple clones and then deposited into GenBank (EU812167). AD293 cells (Stratagene, La Jolla, Calif.) with 70-80% confluency were transiently transfected with rhesus PDE2A3/pcDNA3.3-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES pH 7.4, 1 mM EDTA and Complete Protease Inhibitor Cocktail Tablets (Roche, Indianapolis, Ind.). Lysate was collected by centrifugation at 75,000×g for 20 minutes at 4° C. and supernatant utilized for evaluation of PDE2 activity. The fluorescence polarization assay for cyclic nucleotide phosphodiesterases was performed using an IMAP® FP kit supplied by Molecular Devices, Sunnyvale, Calif. (product # R8139). IMAP® technology has been applied previously to examine the effects of phosphodiesterase inhibitors (Huang, W., et al., J. Biomol Screen, 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE2 inhibitor, which can be any compound that is present at 5,000 times its Ki value in the assay described below, such as Bay 60-7550 (Ki-~0.2 nM) at 1 µM concentration for 100% inhibition. Bay 60-7550 was obtained from Axxora via Fisher Scientific (cat # ALX-270-421-M025/cat #NC9314773). Put another way, any compound with Ki of ~0.2 to about 2 nM could be used at 1 to 10 µM. 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. Ten microliters of a solution of enzyme (1/2000 final dilution from aliquots; sufficient to produce 20% substrate conversion) was added to the assay plate. Next 10 uL of a separate solution of the substrate FAM-labeled cAMP (50 nM final concentration product # R7506 from Molecular Devices) and the activator cGMP (1 uM final concentration), prepared in the assay buffer (10 mM Tris HCl, pH 7.2, 10 mM $MgCl_2$, 0.05% $NaN_3$ 0.01% Tween-20, and 1 mM DTT) was added to the assay plate and shaken to mix. The reaction is allowed to proceed at room temperature for 60 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 30 seconds. The plate was incubated at room temperature for at least one hour prior to determining the fluorescence polarization (FP). The parallel and perpendicular fluorescence of each well of the plate was measured using a Tecan Genios Pro plate reader (Tecan, Switzerland) or Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation: Polarization (mP)=1000*(S/So−P/Po)/(S/So+P/Po).

Dose-inhibition profiles for each compound were characterized by fitting the mP data to a four-parameter equation given below. The apparent inhibition constant (KI), the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\%\ mP - 100\%\ mP)(I\max - I\min)}{1 + \left[\left(10^{-pK_1}\left(1 + \frac{[Substrate]}{K_M}\right)\right)\right]^{nH}} +$$

$$100\%\ mP + (0\%\ mP - 100\%\ mP)(1 - I\max)$$

The median signal of the "0% inhibition controls" (0% mP) and the median signal of the "100% inhibition controls" (100% mP) are constants determined from the controls located in columns 1-2 and 23-24 of each assay plate. An apparent ($K_M$) for FAM-labeled cAMP of ~10 uM was used.

Selectivity for PDE2, as compared to other PDE families, was assessed using the IMAP® technology. Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat #60010), human PDE2A1 (Cat #60020), PDE3A (Cat #60030), PDE4A1A (Cat #60040), PDE5A1 (Cat #60050), PDE6C (Cat #60060), PDE7A (Cat #60070), PDE8A1 (Cat #60080), PDE9A2 (Cat #60090), PDE11A4 (Cat #60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP # R7508), at a final concentration of 50 nM were made in the assay buffer (10 mM Tris HCl, pH 7.2, 10 mM $MgCl_2$, 0.05% $NaN_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, human PDE2A1 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE2 inhibitory activity of a compound which may be used in accordance with the present invention may be determined by these assays.

The compounds of the following examples had activity in inhibiting the human PDE2 enzyme in the aforementioned assays with a Ki of less than about 50 µM. Many of compounds within the present invention had activity in inhibiting the human PDE2 enzyme in the aforementioned assays, with a Ki of less than about 1 µM, preferably less than or about 0.1 µM. Additional data is provided in the following Examples. Such a result is indicative of the intrinsic activity of the compounds in use as inhibitors of the PDE2 enzyme. In general, one of ordinary skill in the art would appreciate that a substance is considered to be particularly effective for inhibiting PDE2 activity if it has a Ki of less than or about 1 µM, preferably less than or about 0.1 µM. The present invention also includes compounds within the generic scope of the invention which possess activity as inhibitors of other phosphodiesterase enzymes.

In the following tables representative data for the compounds of formula I as PDE2 inhibitors as determined by the foregoing assays and as conducted in laboratory (Lab) A or B are shown. The PDE2 Ki is a measure of the ability of the test compound to inhibit the action of the PDE2 enzyme. Table 5. PDE2 Ki's (NA=Not available)

TABLE 5

| Example No. | Rhesus PDE2 Ki (nM) Lab A | Rhesus PDE2 Ki (nM) Lab B | Human PDE2 Ki (nM) Lab A | Human PDE2 Ki (nM) Lab B |
|---|---|---|---|---|
| 1 | 290 | NA | NA | NA |
| 2 | 237 | NA | 392.2 | NA |
| 3 | 4792 | NA | NA | NA |
| 4 | 2342 | NA | NA | NA |
| 5 | 401 | NA | NA | NA |
| 6 | 468 | NA | NA | NA |
| 7 | 2651 | NA | NA | NA |
| 8 | ~642 | NA | NA | NA |
| 9 | 4.3 | NA | 3.4 | NA |
| 10 | 308 | NA | NA | NA |
| 11 | 1396 | NA | NA | NA |
| 12 | 196 | NA | 141 | NA |
| 13 | 20 | 72 | NA | 55 |
| 14 | 137 | NA | 65 | NA |
| 15 | 997 | NA | NA | NA |
| 16 | 866 | NA | 429 | NA |
| 17 | 1.5 | 6.0 | NA | 3.8 |
| 18 | 1966 | NA | NA | NA |
| 19 | NA | 80 | NA | 67 |
| 20 | 5.5 | NA | 6.1 | 8.4 |
| 21 | 194 | NA | 140 | NA |
| 22 | NA | 55 | NA | 35 |
| 23 | NA | 20 | NA | 16 |
| 24 | NA | NA | NA | 29 |
| 25 | NA | 358 | NA | 430 |
| 26 | NA | NA | NA | 4.9 |
| 27 | NA | NA | NA | 40 |
| 28 | NA | 98 | NA | 76 |
| 29 | NA | 47 | NA | 39 |
| 30 | NA | NA | NA | 32 |
| 31 | NA | NA | NA | 55 |
| 32 | NA | NA | NA | 51 |
| 33 | NA | NA | NA | 1327 |
| 34 | NA | NA | NA | >2955 |
| 35 | NA | NA | NA | 566 |
| 36 | NA | NA | NA | 206 |
| 37 | NA | NA | NA | 115 |
| 38 | NA | NA | NA | ~2061 |
| 39 | NA | NA | NA | 503 |
| 40 | NA | NA | NA | 462 |
| 41 | NA | NA | NA | 337 |
| 42 | NA | NA | NA | 580 |
| 43 | NA | NA | NA | 169 |
| 44 | NA | NA | NA | 259 |
| 45 | NA | NA | NA | 682 |
| 46 | NA | NA | NA | ~2640 |
| 47 | NA | NA | NA | 199 |
| 48 | NA | NA | NA | 174 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound represented by structural formula I:

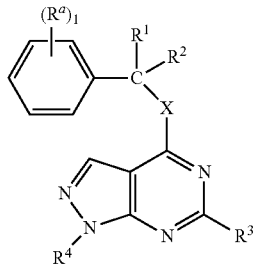

or a pharmaceutically acceptable salt thereof, wherein:

X represents NH, or O;

R is selected from the group consisting of H and $C_{1-6}$alkyl, one of $R^1$ and $R^2$ is hydrogen and the other is $C_{1-6}$alkyl, said alkyl is optionally substituted with 1 to 3 groups of $R^a$;

or $R^1$ and $R^2$ can combine with the carbon to which they are attached to form a $C_{3-10}$cycloalkyl or $C_{3-10}$heterocycloalkyl, said cycloalkyl and heterocycloalkyl are optionally substituted with 1 to 3 groups of $R^a$, wherein when $R^1$ and $R^2$ are combined $R^a$ is selected from the group consisting of $(CH_2)_nCF_3$, $OCF_3$, $C(CH_3)_3$, $OC(CH_3)_3$, $CHF_2$, $SF_5$, $SCF_3$, $OCHF_2$, and $CH(CH_3)_2$;

$R^3$ represents halo, $C_{1-6}$alkyl, $C_{1-4}$haloalkyl, $(CH_2)_nOR$, $C_{3-10}$cycloalkyl, or CN, said alkyl and cycloalkyl are optionally substituted with 1 to 3 groups of $R^a$;

$R^4$ is selected from the group consisting of hydrogen, $(CH_2)_nOR$, $C_{1-6}$alkyl, $(CH_2)_nC_{1-4}$haloalkyl, CN, and $N(R)_2$, said alkyl is optionally substituted with one to three groups of $R^a$;

$R^a$ is selected from the group consisting of halo, CN, $C_{1-6}$alkyl, $(CH_2)_nOR$, $(CH_2)_nCF_3$, $(O)_pC_{1-4}$haloalkyl, $N(R)_2$, $SCF_3$, $SF_5$, $C_{3-10}$cycloalkyl, $C_{6-10}$aryl, and $C_{4-10}$heterocyclyl;

n represents 0, 1, 2, 3, or 4; and provided that when X is NH, then $R^1$ and $R^2$ combine with the carbon to which they are attached to form a $C_{3-10}$cycloalkyl or $C_{3-10}$heterocycloalkyl, said cycloalkyl and heterocycloalkyl are optionally substituted with 1 to 3 groups of $R^a$; and p represents 0 or 1.

2. The compound according to claim 1 or a pharmaceutically acceptable salt thereof wherein X is NH.

3. The compound according to claim 1 or a pharmaceutically acceptable salt thereof wherein $R^4$ is hydrogen.

4. The compound according to claim 1 or a pharmaceutically acceptable salt thereof wherein $R^4$ is selected from the group consisting of H, $CH_3$, $(CH_2)_nOH$, $C(CH_3)_2OH$, $C(CH_3)_3$, $CH(CH_3)_2$, $CH_2C(CH_3)_2OH$, $CH_2CH_3$ $(CH_2)_n$ $CHF_2$, $(CH_2)_nCH_2F$, $(CH_2)_nCF_3$, $NH_2$, $N(CH_3)_2$, $NHCH_3$, $OCH_2CH_3$, $(CH_2)_nOCH_3$, and CN.

5. The compound according to claim 4 or a pharmaceutically acceptable salt thereof wherein $R^4$ is selected from the group consisting of $CH_3$, $CH(CH_3)_2$, $C(CH_3)_2OH$, $C(CH_3)_3$, $CH_2CH_3$, $(CH_2)_nOH$, $CHF_2$, $CH_2F$, $CH_2CF_3$, $CF_3$, and $NH_2$.

6. The compound according to claim 1 or a pharmaceutically acceptable salt thereof wherein X is O, and one of $R^1$ and $R^2$ is hydrogen and the other is selected from the group consisting $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_{1-4}OH$, $C(CH_3)_2NH_2$, $C(CH_2CH_3)_2OH$, and $(CH_2)_{1-4}OCH_3$.

7. The compound according to claim 1 or a pharmaceutically acceptable salt thereof wherein X is NH, and $R^1$ and $R^2$ combine with the carbon to which they are attached to form an optionally substituted $C_{3-10}$cycloalkyl or $C_{3-10}$heterocycloalkyl, selected from the group consisting of cyclopropyl, cyclobutyl, cyclopentyl, cyclohexyl, or oxetanyl, said $C_{3-10}$cycloalkyl or $C_{3-10}$heterocycloalkyl are optionally substituted with 1 to 3 groups selected from $R^a$ where $R^a$ is selected from the group consisting of $(CH_2)_nCF_3$, $OCF_3$, $C(CH_3)_3$, $OC(CH_3)_3$, $CHF_2$, $SF_5$, $SCF_3$, $OCHF_2$, and $CH(CH_3)_2$.

8. The compound according to claim 1 or a pharmaceutically acceptable salt thereof wherein $R^3$ is selected from the group consisting of halo, OH, $(CH_2)_nCH_3$, $CH(CH_3)_2$, $C(CH_3)_3$, $(CH_2)_nOCH_3$, $CH_2F$, $CHF_2$, $(CH_2)_nCF_3$, CN, and cyclopropyl optionally substituted with 1 to 3 groups of $R^a$.

9. A compound which is:
6-Chloro-1-methyl-N-{1-[4-(trifluoromethyl)phenyl]ethyl}-1H-pyrazolo[3,4-d]pyrimidin-4-amine,
6-Chloro-1-methyl-N-{(1R)-1-[4-(trifluoromethyl)phenyl]ethyl}-1H-pyrazolo[3,4-d]pyrimidin-4-amine,
6-Chloro-1-methyl-N-{(1S)-1-[4-(trifluoromethyl)phenyl]ethyl}-1H-pyrazolo[3,4-d]pyrimidin-4-amine,
6-Chloro-1-methyl-N-[4-(trifluoromethyl)benzyl]-1H-pyrazolo[3,4-d]pyrimidin-4-amine,
6-Chloro-1-methyl-N-{1-[4-(1-methylethyl)phenyl]ethyl}-1H-pyrazolo[3,4-d]pyrimidin-4-amine,
6-Chloro-1-methyl-N-{1-(4-[1-methylethyl]phenyl]propyl}-1H-pyrazolo[3,4-d]pyrimidin-4-amine,
6-Chloro-1-methyl-N-{1-[4-(1H-pyrazol-1-yl)phenyl]ethyl}-1H-pyrazolo[3,4-d]pyrimidin-4-amine,
6-Chloro-1-methyl-N-{1-methyl-1-[4-(trifluoromethyl)phenyl]ethyl}-1H-pyrazolo[3,4-d]pyrimidin-4-amine,
6-Chloro-1-methyl-N-{1-[4-(trifluoromethyl)phenyl]cyclopropyl}-1H-pyrazolo[3,4-d]pyrimidin-amine,
6-Chloro-N-{(1R)-1-[4-(trifluoromethyl)phenyl]ethyl}-1H-pyrazolo[3,4-d]pyrimidin-4-amine,
6-Chloro-N-{(1S)-1-[4-(trifluoromethyl)phenyl]ethyl}-1H-pyrazolo[3,4-d]pyrimidin-4-amine,
1-Methyl-4-({1-[4-(trifluoromethyl)phenyl]cyclopropyl}amino)-1H-pyrazolo[3,4-d]pyrimidin-6-ol,
6-Cyclopropyl-1-methyl-N-{1-[4-(trifluoromethyl)phenyl]cyclopropyl}-1H-pyrazolo[3,4-d]pyrimidin-4-amine,
6-Chloro-N,1-dimethyl-N-{(1R)-1-[4-(trifluoromethyl)phenyl]ethyl}-1H-pyrazolo[3,4-d]pyrimidin-4-amine,
6-Chloro-N,1-dimethyl-N-[4-(trifluoromethyl)benzyl]-1H-pyrazolo[3,4-d]pyrimidin-4-amine,
6-Chloro-N-ethyl-1-methyl-N-[4-(trifluoromethyl)benzyl]-1H-pyrazolo[3,4-d]pyrimidin-4-amine,
6-Chloro-N,1-dimethyl-N-{1-[4-(trifluoromethyl)phenyl]cyclopropyl}-1H-pyrazolo[3,4-d]pyrimidin-4-amine,
6-Chloro-1-(1-methylethyl)-N-{1-[4-(trifluoromethyl)phenyl]ethyl}1-1H-pyrazolo[3,4-d]pyrimidin-4-amine,
1-Methyl-6-(trifluoromethyl)-N-{1-[4-(trifluoromethyl)phenyl]cyclopropyl}-1H-pyrazolo[3,4-d]pyrimidin-4-amine,
1,6-Dimethyl-N-{1-[4-(trifluoromethyl)phenyl]cyclopropyl}-1H-pyrazolo[3,4-d]pyrimidin-4-amine,
1,6-Dimethyl-N-{(1R)-1-[4-(trifluoromethyl)phenyl]ethyl}-1H-pyrazolo[3,4-d]pyrimidin-4-amine, N-{1-[3-Fluoro-4-(trifluoromethoxy)phenyl]cyclopropyl}-1,6-dimethyl-1H-pyrazolo[3,4-d]pyrimidin-4-amine,
1,6-Dimethyl-N-(1-{4-[(trifluoromethyl)sulfanyl]phenyl}cyclopropyl)-1H-pyrazolo[3,4-d]pyrimidin-4-amine,
N-{1-[2-Fluoro-4-(trifluoromethyl)phenyl]cyclopropyl}-1,6-dimethyl-1H-pyrazolo[3,4-d]pyrimidin-4-amine,
1,6-Dimethyl-N-{1-[4-(trifluoromethyl)phenyl]cyclobutyl}-1H-pyrazolo[3,4-d]pyrimidin-4-amine,
N,1,6-Trimethyl-N-{1-[4-(trifluoromethyl)phenyl]cyclopropyl}-1H-pyrazolo[3,4-d]pyrimidin-4-amine,
N,1,6-Trimethyl-N-(1-{4-[(trifluoromethyl)sulfanyl]phenyl}cyclopropyl)-1H-pyrazolo[3,4-d]pyrimidin-4-amine,
N-{1-[3-Fluoro-4-(trifluoromethyl)phenyl]cyclopropyl}-6-methyl-1-(2,2,2-trifluoroethyl)-1H-pyrazolo[3,4-d]pyrimidin-4-amine,
1-Methyl-4-({1-[4-(trifluoromethyl)phenyl]cyclopropyl}amino)-1H-pyrazolo[3,4-d]pyrimidine-6-carbonitrile, or
1,6-Dimethyl-4-({1-[4-(trifluoromethyl)phenyl]cyclopropyl}oxy)-1H-pyrazolo[3,4-d]pyrimidine,
or a pharmaceutically acceptable salt thereof.

10. A pharmaceutical composition which comprises a pharmaceutically acceptable carrier and a compound of claim 1 or a pharmaceutically acceptable salt thereof.

11. The compound of claim 1 or a pharmaceutically acceptable salt thereof wherein
when X is O, $R^a$ is selected from the group consisting of $(CH_2)_nCF_3$, $OCF_3$, $C(CH_3)_3$, $OC(CH_3)_3$, $CHF_2$, $SF_5$, $SCF_3$, $OCHF_2$, and $CH(CH_3)_2$; $R^3$ is selected from the group consisting of halo, OH, $(CH_2)_nCH_3$, $CH(CH_3)_2$, $C(CH_3)_3$, $(CH_2)_nOCH_3$, $CH_2F$, $CHF_2$, $(CH_2)_{1-3}CF_3$, CN, and cyclopropyl optionally substituted with 1 to 3 groups of $R^a$; $R^4$ is selected from the group consisting of $(CH_2)_nOH$, $CH(CH_3)_2$, $CH_3$, and $CH_2CF_3$; and one of $R^1$ and $R^2$ is hydrogen and the other is selected from the group consisting of $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, and $(CH_2)_n\ OCH_3$.

12. The compound of claim 1 or a pharmaceutically acceptable salt thereof wherein
when X is NH, $R^3$ is selected from the group consisting of halo, OH, $(CH_2)_nCH_3$, $CH(CH_3)_2$, $C(CH_3)_3$, $(CH_2)_n OCH_3$, $CH_2F$, $CHF_2$, $(CH_2)_{1-3}CF_3$, CN, and cyclopropyl optionally substituted with 1 to 3 groups of $R^a$; $R^4$ is selected from the group consisting of $(CH_2)_nOH$, $CH(CH_3)_2$, $CH_3$, and $CH_2CF_3$, and $R^1$ and $R^2$ combine with the carbon to which they are attached to form an optionally substituted $C_{3-10}$cycloalkyl or $C_{3-10}$heterocycloalkyl, selected from the group consisting of cyclopropyl, cyclobutyl, cyclopentyl, cyclohexyl, or oxetanyl, said $C_{3-10}$cycloalkyl or $C_{3-10}$heterocycloalkyl are optionally substituted with 1 to 3 groups selected from $R^a$, where $R^a$ is selected from the group consisting of $(CH_2)_nCF_3$, $OCF_3$, $C(CH_3)_3$, $OC(CH_3)_3$, $CHF_2$, $SF_5$, $SCF_3$, $OCHF_2$, and $CH(CH_3)_2$.

* * * * *

UNITED STATES PATENT AND TRADEMARK OFFICE
CERTIFICATE OF CORRECTION

PATENT NO. : 10,647,727 B2  
APPLICATION NO. : 15/579115  
DATED : May 12, 2020  
INVENTOR(S) : Gregori J. Morriello et al.

Page 1 of 1

It is certified that error appears in the above-identified patent and that said Letters Patent is hereby corrected as shown below:

On the Title Page

(71) Delete:
"Gregori J. Morriello
Michael P. Dwyer
Lehua Chang
Yili Chen
Ming Wang
Ashley Forster
Richard Berger
Kausik K. Nanda
Jamie L. Bunda
William D. Shipe"

And insert:
--Merck Sharp & Dohme Corp.--

Signed and Sealed this  
Ninth Day of February, 2021

Drew Hirshfeld  
*Performing the Functions and Duties of the*  
*Under Secretary of Commerce for Intellectual Property and*  
*Director of the United States Patent and Trademark Office*